US011116832B2

(12) United States Patent
Strugnell et al.

(10) Patent No.: US 11,116,832 B2
(45) Date of Patent: Sep. 14, 2021

(54) MODIFICATION OF ENGINEERED INFLUENZA HEMAGGLUTININ POLYPEPTIDES

(71) Applicant: Sanofi Pasteur Inc., Swiftwater, PA (US)

(72) Inventors: Tod Strugnell, Cambridge, MA (US); Eliud Oloo, Cambridge, MA (US); Raymond Oomen, Cambridge, MA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 123 days.

(21) Appl. No.: 16/306,325

(22) PCT Filed: Jun. 2, 2017

(86) PCT No.: PCT/US2017/035738
§ 371 (c)(1),
(2) Date: Nov. 30, 2018

(87) PCT Pub. No.: WO2017/210592
PCT Pub. Date: Dec. 7, 2017

(65) Prior Publication Data
US 2020/0215182 A1    Jul. 9, 2020

Related U.S. Application Data

(60) Provisional application No. 62/345,502, filed on Jun. 3, 2016.

(51) Int. Cl.
| | |
|---|---|
| *A61K 39/395* | (2006.01) |
| *A61K 39/00* | (2006.01) |
| *C07K 16/18* | (2006.01) |
| *C07K 16/28* | (2006.01) |
| *A61K 45/06* | (2006.01) |
| *A61K 39/145* | (2006.01) |
| *A61P 31/16* | (2006.01) |
| *C07K 14/005* | (2006.01) |
| *C12N 7/00* | (2006.01) |

(52) U.S. Cl.
CPC .......... *A61K 39/145* (2013.01); *A61P 31/16* (2018.01); *C07K 14/005* (2013.01); *C12N 7/00* (2013.01); *A61K 2039/5258* (2013.01); *C12N 2760/16122* (2013.01); *C12N 2760/16123* (2013.01); *C12N 2760/16134* (2013.01)

(58) Field of Classification Search
CPC .......... A61K 2039/505; A61K 2300/00; C07K 2317/565; C07K 2317/76; C07K 2317/56
See application file for complete search history.

(56) References Cited

FOREIGN PATENT DOCUMENTS

WO    2011/044152 A1    4/2011

OTHER PUBLICATIONS

Carteret al., "Design and Characterization of a computationally optimized broadlyreactive hemagglutinin vaccine for H1N1 influenza viruses", Journal of Virology, 2016:4720-4734.*
Carter et al., "Design and Characterization of a computationally optimized broadly reactive hemagglutinin vaccine for H1N1 influenza viruses", Journal of Virology, 2016, 90(9)4720-4734.*
Carter et al., "Design and Characterization of a Computationally Optimized Broadly Reactive Hemagglutinin Vaccine for H1N1 Influenza Viruses", Journal of Virology (Online), American Society for Microbiology, US, 90(9): 4720-4734 (2016).
Sun et al., "N-Linked Glycosylation of the Hemagglutinin Protein Influences Virulence and Antigenicity of the 1918 Pandemic and Seasonal H1N1 Influenza A Viruses", Journal of Virology, 87(15): 8756-8766 (2013).

* cited by examiner

*Primary Examiner* — Barry A Chestnut
(74) *Attorney, Agent, or Firm* — MH2 Technology Law Group, LLP

(57) ABSTRACT

The present invention provides, among other things, modified recombinant HA polypeptides with broadened immunogenic profile that extends coverage to antigenically distinct influenza strains and methods of making and using the same.

14 Claims, 12 Drawing Sheets

Specification includes a Sequence Listing.

FIG. 3

|  | mAb | SMARDO2a | DO2a_tr5 | DO2a_tr6 | DO2a_tr7 | DO2a_tr8 |
|---|---|---|---|---|---|---|
| STEM | AS2 | 582 | 558 | 386 | 612 | 643 |
|  | AS3 | 757 | 664 | 393 | 654 | 620 |
|  | AH4 | 814 | 1266 | 928 | 1774 | 1431 |
|  | AH5 | 945 | 1371 | 1100 | 2030 | 1654 |
|  | CH65 | 613 | 952 | 865 | 1955 | 1301 |
|  | 5J8 | 373 | 681 | 670 | 1321 | 1086 |
| HEAD | 4K8 | 120 | 128 | 82 | 108 | 96 |

A/CAL/09 LUNG TITERS
DAY 4

FIG. 14

MODIFICATION OF ENGINEERED INFLUENZA HEMAGGLUTININ POLYPEPTIDES

CROSS REFERENCE TO RELATED APPLICATIONS

This application is a 35 U.S.C. § 371 National Stage Application of International Application No. PCT/US17/35738, filed Jun. 2, 2017, which claims priority to U.S. Provisional Patent Application 62/345,502 filed Jun. 3, 2016, the entirety of which is hereby incorporated by reference.

INCORPORATION-BY-REFERENCE OF SEQUENCE LISTING

The content of the text file named "SPR-003US_SL.txt", which was created on Nov. 30, 2018 and is 118 KB in size, is hereby incorporated by reference in its entirety.

BACKGROUND

Influenza has a long standing history of pandemics, epidemics, resurgences and outbreaks. Vaccines have been the most effective defense against influenza. However, the effort to design and manufacture vaccines that induce strain-specific immunity year-over-year has been difficult as influenza continues to cause significant health problems across the globe. Indeed, currently marketed influenza vaccines must be updated annually based on predicted strains that will be present in human populations in the impending season.

Current influenza vaccines are based on inducing immunity to the hemagglutinin antigen present on the surface of influenza viruses. Hemagglutinin (HA) is a glycoprotein responsible for the binding of the influenza virus to cells through interaction with sialic acid-containing structures on their membranes. It is highly variable across influenza virus strains due to on-going mutation of the virus and immune pressure by the host. Variability (also known as antigenic drift) in the HA molecule results in a HA polypeptide-based vaccine generally reactive only to a small subset of related circulating viruses. Over time, the number of cross-reactive strains decreases as the virus continues to mutate. Consequently, the HA compositions of influenza vaccines are modified on regular basis when the variation in the HA molecule is such that the existing vaccine is no longer effective. Among the current strategies for vaccination against influenza, the development of a universal vaccine holds the promise to increase the breadth of current strain-specific vaccines and tolerance to antigenic drift. Universal influenza vaccines have the potential to protect humans and animals against a broad range of influenza types, subtypes and strains, including pandemic and/or seasonal strains. Several approaches to designing universal influenza antigens are known in the art. However, the existing approaches often result in an HA polypeptide that remains biased towards seasonal or pandemic strains.

SUMMARY

The present invention provides improved modified recombinant HA polypeptides with broadened immunogenic profile that extends coverage (i.e., the capability of eliciting a immunogenic response against the HA polypeptide) to antigenically distinct influenza strains, for example to new or additional pandemic and/or seasonal influenza strains.

The present invention is, in part, based on modifications deduced from in silico analysis of sequence variation among circulating influenza strains, mapping of the antigenic region of HA, and/or epitope patterns and structural analyses of the HA peptide. Targeted modifications can be subsequently introduced at various amino acid residue locations and/or specific regions of an HA polypeptide with a known immune profile to yield novel HA polypeptides with improved and more balanced immune profiles. As described in detail below including the Examples section, the present inventors have developed—among other things—various distinct strategies for engineering HA polypeptides to extend a seasonal response profile to cover pandemic strains, or vice versa. These strategies extend the immune profile across clusters of sequences (or clades) of antigenically distinct strains; they can be applied to an engineered recombinant HA molecule over time so that it continues to elicit an immune response against antigenically drifted circulating seasonal strains. In all cases, the strategy is designed to generally preserve specific residues of the receptor binding site (RBS) of a host HA polypeptide with modifications engineered in the region near the RBS. Similar strategies may be used to extend a pandemic response profile to cover seasonal strains. The compositions and methods of the present invention are applicable to a wide variety of recombinant HA polypeptides, including those engineered by a variety of methods and those comprising substantially wild-type sequences.

Thus, in one aspect, the present invention provides a recombinant hemagglutinin (HA) polypeptide comprising an engineered head region or segment thereof derived from an engineered HA polypeptide with a predominantly seasonal immune profile and a stem region derived from a pandemic strain. In some embodiments, the engineered head region or segment thereof comprises a sequence at least 95%, 96%, 97%, 98%, 99% or more identical to amino acids corresponding to positions 135-269, 125-277, or 63-278 of SEQ ID NO:1. In some embodiments, the engineered head region or segment thereof comprises a sequence identical to amino acids corresponding to positions 135-269, 125-277, or 63-278 of SEQ ID NO:1 (SMARt_DO2a sequence).

In some embodiments, the stem region is derived from a naturally-occurring or wild-type pandemic strain. In some embodiments, a suitable naturally-occurring pandemic strain is selected from A/California/07/2009, A/New Jersey/10/1976, or A/South Carolina/1/1918. In some embodiments, the stem region is derived from an engineered HA polypeptide that has a pandemic immune profile.

In some embodiments, the engineered HA polypeptide that has a pandemic immune profile is engineered by a computationally optimized broadly reactive antigens (COBRA) technology, a mosaic technology, consensus-based combinations of influenza strains, deletion and/or rearrangement of structural domains, domain swapping, or combinations of neutralizing or cross-reactive epitopes among multiple influenza strains.

In another aspect, the present invention provides a recombinant influenza hemagglutinin (HA) polypeptide comprising an engineered head region derived from an HA polypeptide with a predominantly seasonal immune profile and comprising one or more amino acid substitutions, deletions or insertions at one or more putative N-linked glycosylation sites defined by a consensus sequence of NxS/Ty, wherein x and y are not Proline (P), such that the one or more putative N-linked glycosylation sites are disrupted. In particular embodiments, each of the one or more amino acid substitutions, deletions or insertions is derived from a corresponding sequence in a pandemic strain.

In yet another aspect, the present invention provides a recombinant influenza hemagglutinin (HA) polypeptide comprising an engineered head region derived from an HA polypeptide with a predominantly pandemic immune profile into which has been inserted one or more engineered putative N-linked glycosylation sites defined by a consensus sequence of NxS/Ty, wherein x and y are not P. In particular embodiments, each of the one or more engineered putative N-linked glycosylation sites is engineered by amino acid substitutions, deletions or insertions based on a corresponding sequence in a seasonal strain.

In some embodiments, the hemagglutinin corresponds to type A influenza. In some embodiments, the type A influenza is subtype H1N1.

In some embodiments, the one or more putative N-linked glycosylation sites correspond to positions 142-145 and/or 177-179 (normalized sequence alignment to A/California/07/2009 HA (SEQ ID NO: 2); "CA09 Numbering"). In some embodiments, the one or more putative N-linked glycosylation sites are within 15 angstroms of the Receptor Binding Site (RBS), wherein the RBS is defined as all amino acid residues within 15 angstroms of a position corresponding to W167 (CA09 Numbering) in a three-dimensional (3-D) structure. Alternatively, the RBS may be defined as the epitope bound by the paratope of monoclonal antibody CH65, and the one more amino acid substitutions occur adjacent to (e.g., within 100 amino acid residues, within 75 amino acid residues, within 50 amino acid residues, within 40 amino acid residues, within 30 amino acid residues, within 25 amino acid residues, within 20 amino acid residues, within 15 amino acid residues, within 10 amino acid residues, within 5 amino acid residues, etc.) the epitope of CH65. In some embodiments, the one or more amino acid substitutions, deletions or insertions are selected from lists or tables provided herein, e.g., Table 4, or Table 5. In some embodiments, the one or more amino acid substitutions, deletions or insertions comprise modifying the consensus sequence NxS/Ty to $z^1z^2z^3z^4$ wherein $z^1$ is N, D, K or S; $z^2$ is Y or is unchanged; $z^3$ is E, D or N; and $z^4$ is I, L, P, S or T, or is unchanged.

In some embodiments, the pandemic or seasonal strain from which one or more amino acid substitutions, deletions or insertions are derived is a circulating influenza strain. In some embodiments, the circulating influenza strain is selected from the group consisting of A/California/07/2009 and A/South Carolina/1/1918. In some embodiments, the amino acid substitutions, deletions or insertions comprise insertion of a Lysine (K) or Arginine (R) residue within 1-5 amino acids (e.g., within 1-4, 1-3, 1-2 amino acids) of the NxS/Ty consensus sequence. In some embodiments, the Lysine (K) or Arginine (R) residue is within 1-5 amino acids (e.g., within 1-4, 1-3, 1-2 amino acids) 3' of the NxS/Ty consensus sequence. In some embodiments, the one or more amino acid substitutions, deletions or insertions comprise an insertion at a position corresponding to residue 147 (CA09 Numbering). In some embodiments, the insertion at the position corresponding to residue 147 comprises an insertion of Lysine (K) or Arginine (R).

In a further aspect, the present invention provides a recombinant influenza HA polypeptide comprising an engineered head region derived from an HA polypeptide with a predominantly seasonal immune profile and comprising one or more amino acid substitutions between positions corresponding to 60 and 291 of (CA09 Numbering), wherein each of the one or more amino acid substitutions is derived from a corresponding sequence in a pandemic strain. In some embodiments, the one or more amino acid substitutions are selected from lists or tables provided herein, e.g., Table 6. In some embodiments, the one or more amino acid substitutions are between positions corresponding to 137 and 262 (CA09 Numbering), and wherein the one or more amino acid substitutions are selected from Table 7. In some embodiments, the one or more amino acid substitutions comprise two, three, four, five, six, seven, eight, nine, ten or more amino acid substitutions selected from Table 3 or Table 4. In some embodiments, the one or more amino acid substitutions comprise at least 2, 3, 4, 5, 6, 7, 8, 9, or 10 consecutive substitutions selected from Table 6 or Table 7. In some embodiments, the one or more amino acid substitutions occur at positions corresponding to 137, 144, 145, 154, 155, 156, 157, 158, 159, 177, 210, 211, 212, 213, 214, 244, 245, and/or 262 (CA09 Numbering).

In a related aspect, the present invention provides a recombinant influenza HA polypeptide comprising an engineered head region derived from an HA polypeptide with a predominantly seasonal immune profile and comprising one or more amino acid substitutions within 15 angstroms of the Receptor Binding Site (RBS), wherein the RBS is defined as all amino acid residues within 15 angstroms of a position corresponding to W167 (CA09 Numbering) in a three-dimensional (3-D) structure, wherein each of the one or more amino acid substitutions is derived from a corresponding sequence in a pandemic strain. Alternatively, the RBS may be defined as the epitope bound by the paratope of monoclonal antibody CH65, and the one more amino acid substitutions occur adjacent to (e.g., within 100 amino acid residues, within 75 amino acid residues, within 50 amino acid residues, within 40 amino acid residues, within 30 amino acid residues, within 25 amino acid residues, within 20 amino acid residues, within 15 amino acid residues, within 10 amino acid residues, within 5 amino acid residues, etc.) the epitope of CH65.

In some embodiments, the pandemic strain is a circulating influenza virus. In some embodiments, the one or more amino acid substitutions are within 10 (e.g., within 9, 8, 7, 6, 5, etc.) angstroms of Receptor Binding Site (RBS). In some embodiments, the one or more amino acid substitutions comprise two, three, four, five, six, seven, eight, nine, ten or more amino acid substitutions selected from Table 8. In some embodiments, the one or more amino acid substitutions comprise at least 2, 3, 4, 5, 6, 7, 8, 9, or 10 consecutive substitutions selected from Table 8. In some embodiments, the one or more amino acid substitutions occur at positions corresponding to 137, 144, 145, 154, 155, 156, 157, 158, 159, 177, 210, 211, 212, 213, and/or 214 (CA09 Numbering).

In still another aspect, the present invention provides a recombinant influenza HA polypeptide comprising an engineered head region derived from an HA polypeptide with a predominantly seasonal immune profile and comprising one or more amino acid modifications selected from Table 9 (e.g., two or more, three or more, four or more, five or more modifications selected from Table 9).

In some embodiments, the HA polypeptide with a predominantly seasonal immune profile or the HA polypeptide with a predominantly pandemic immune profile suitable for the present invention is engineered by a computationally optimized broadly reactive antigens (COBRA) technology, a mosaic technology, influenza consensus sequences based combinations of influenza strains, deletion and/or rearrangement of structural domains, domain swapping, or combinations of neutralizing or cross-reactive epitopes among multiple influenza strains.

In some embodiments, the recombinant HA polypeptide elicits neutralizing antibodies against both seasonal and pandemic strains of influenza virus. In particular embodiments, the recombinant HA polypeptide elicits neutralizing antibodies against one or more seasonal strains and one more pandemic strains of influenza virus. In some embodiments, the recombinant HA polypeptide is characterized by a more balanced immunogenic profile against both seasonal and pandemic strains of influenza virus.

Among other things, the present invention provides an isolated nucleic acid encoding a recombinant HA polypeptide described herein and a vector comprising such a nucleic acid. In some embodiments, the present invention provides a cell containing such a vector or a nucleic acid. In some embodiments, a suitable cell is a human cell. In particular embodiments, the human cell is a HEK-293 cell. In some embodiments, a suitable cell is a monkey cell. In particular embodiments, the monkey cell is a Vero cell.

In various additional aspects, the present invention provides virus-like particles (VLP)s comprising a recombinant HA polypeptide as described herein. In some embodiments, a VLP according to the invention further comprises an influenza neuraminidase (NA) protein, a human immunodeficiency virus (HIV) gag protein, or both. The present invention also provides pharmaceutical compositions comprising a recombinant HA polypeptide or a VLP as described herein. Furthermore, the present invention provides methods of generating an immune response (e.g., immunizing or vaccinating) against seasonal and pandemic influenza virus in a subject by administration of a pharmaceutical composition described herein.

In another aspect, the present invention provides methods of altering the immunogenic profile of an engineered HA polypeptide. In some embodiments, a method of altering the immunogenic profile of an engineered HA polypeptide comprises: selecting a head region of the engineered HA polypeptide and substituting the selected head region of the engineered HA polypeptide for a corresponding head region of an HA polypeptide with a distinct immunogenic profile, thereby generating a re-engineered HA polypeptide with altered immunogenic profile. In some embodiments, the engineered HA polypeptide has a predominantly seasonal immune profile, and the HA polypeptide with a distinct immunogenic profile has a predominantly pandemic immune profile.

In some embodiments, the selected head region of the engineered HA polypeptide with a predominantly seasonal immune profile correspond to residues 63-278, 125-277 or 135-269 (CA09 Numbering). In some embodiments, the corresponding head region of the HA polypeptide with a distinct immunogenic profile, which is predominantly pandemic, comprises an amino acid sequence selected from: residues of 63-277 of SEQ ID NO:2 [full-length wt CA09 (A/California/07/2009 HA sequence) sequence], residues of 63-277 of SEQ ID NO: 3 [full-length wt SC1918 sequence], residues 63-277 of SEQ ID NO: 4 [full-length wt NJ1976 sequence], residues 125-277 of SEQ ID NO: 2 [full-length wt CA09 sequence], residues 125-277 of SEQ ID NO:3 [full-length wt SC1918 sequence], residues 125-277 of SEQ ID NO: 4[full-length wt NJ1976 sequence], residues 135-269 of SEQ ID NO: 2 [full-length wt CA09 sequence], residues 135-269 of SEQ ID NO: 3 [full-length wt SC1918 sequence], or residues 135-269 of SEQ ID NO: 4 [full-length wt NJ1976 sequence].

In some embodiments, the HA polypeptide with a distinct immunogenic profile, which is predominantly pandemic, is an HA polypeptide from a wild-type influenza virus. In some embodiments, the HA polypeptide with a distinct immunogenic profile, which is predominantly pandemic is an engineered HA polypeptide. In some embodiments, the HA polypeptide with a distinct immunogenic profile, which is predominantly pandemic, comprises SEQ ID NO: 5 (full-length sequence for DO1A).

In some embodiments, the engineered HA polypeptide has a predominantly pandemic immune profile, and the HA polypeptide with a distinct immunogenic profile has a predominantly seasonal immune profile. In some embodiments, the selected head region of the engineered HA polypeptide with a predominantly pandemic immune profile is selected from the group consisting of: residues of 63-277 of SEQ ID NO:2 [full-length wt CA09 (A/California/07/2009 HA sequence) sequence]; residues of 63-277 of SEQ ID NO: 3 [full-length wt SC1918 sequence]; residues of 63-277 of SEQ ID NO: 4 [full-length wt NJ1976 sequence]; residues of 125-277 of SEQ ID NO: 2 [full-length wt CA09 sequence]; residues of 125-277 of SEQ ID NO: 3 [full-length wt SC1918 sequence]; residues of 125-277 of SEQ ID NO: 4 [full-length wt NJ1976 sequence]; residues of 135-269 of SEQ ID NO: 2 [full-length wt CA09 sequence]; residues of 135-269 of SEQ ID NO: 3 [full-length wt SC1918 sequence]; and residues of 135-269 of SEQ ID NO: 4 [full-length wt NJ1976 sequence]. In some embodiments, the corresponding head region of the HA polypeptide with a distinct immunogenic profile, which is predominantly seasonal, comprises residues 63-278, 125-277 or 135-269 of SEQ ID NO: 2 (full-length sequence for SMARt_DO2A).

In some embodiments, the present invention provides methods of altering the immunogenic profile of an engineered HA polypeptide comprising steps of: identifying the presence or absence of one or more putative N-linked glycosylation sites in a head region of the engineered HA polypeptide as compared to the corresponding head region of an HA polypeptide with a distinct immunogenic profile; introducing into the head region of the engineered HA polypeptide one or more amino acid substitutions, deletions or insertions to disrupt the one or more putative N-linked glycosylation sites or insert additional N-linked glycosylation sites based on the corresponding sequence of the HA polypeptide with a distinct immunogenic profile, thereby generating a re-engineered HA polypeptide with altered immunogenic profile. In some embodiments, the one or more putative or additional N-linked glycosylation sites are defined by a consensus sequence of NxS/Ty, wherein x and y are not P. In some embodiments, the engineered HA polypeptide has a predominantly seasonal immune profile, and the HA polypeptide with a distinct immunogenic profile has a predominantly pandemic immune profile, wherein the one or more amino acid substitutions, deletions or insertions are introduced into the engineered HA polypeptide to disrupt the one or more putative N-linked glycosylation sites, and wherein the re-engineered HA polypeptide is altered to be more pandemic. In some embodiments, the engineered HA polypeptide has a predominantly pandemic immune profile, and the HA polypeptide with a distinct immunogenic profile has a predominantly seasonal immune profile, wherein the one or more amino acid substitutions, deletions or insertions are introduced into the engineered HA polypeptide to insert one or more putative additional N-linked glycosylation sites, and wherein the re-engineered HA polypeptide is altered to be more seasonal.

In some embodiments, the present invention provides methods of altering the immunogenic profile of an engineered HA polypeptide comprising introducing one or more amino acid substitutions within 15 (e.g., within 10, 9, 8, 7, 6, 5, etc.) angstroms of the Receptor Binding Site (RBS), wherein the RBS is defined as all amino acids residues within 15 (e.g., within 10, 9, 8, 7, 6, or 5) angstroms of a position corresponding to residue W167 (CA09 Numbering) in a three-dimensional (3-D) structure; wherein each of the one or more amino acid substitutions comprises replacing an amino acid residue at a specific position with an amino acid residue observed at the corresponding position in an HA polypeptide with a distinct immunogenic profile, thereby generating an re-engineered HA polypeptide with altered immunogenic profile. Alternatively, the RBS may be defined as the epitope bound by the paratope of monoclonal antibody CH65, and the one more amino acid substitutions occur adjacent to (e.g., within 100 amino acid residues, within 75 amino acid residues, within 50 amino acid residues, within 40 amino acid residues, within 30 amino acid residues, within 25 amino acid residues, within 20 amino acid residues, within 15 amino acid residues, within 10 amino acid residues, within 5 amino acid residues, etc.) the epitope of CH65. In some embodiments, the HA polypeptide with a distinct immunogenic profile is derived from a circulating seasonal or pandemic influenza strain. In some embodiments, the engineered HA polypeptide has a predominantly seasonal immune profile, and the HA polypeptide with a distinct immunogenic profile has a predominantly pandemic immune profile, and wherein the re-engineered HA polypeptide is altered to be more pandemic. In some embodiments, the engineered HA polypeptide has a predominantly pandemic immune profile, and the HA polypeptide with a distinct immunogenic profile has a predominantly seasonal immune profile, and wherein the re-engineered HA polypeptide is altered to be more seasonal.

In some embodiments, the present invention provides methods of altering the immunogenic profile of an engineered HA polypeptide comprising introducing one or more modifications selected from those shown in Table 4, Table 5, Table 6, Table 7, Table 8, or Table 9, into one or more corresponding positions of the engineered HA polypeptide, thereby generating a re-engineered HA polypeptide with altered immunogenic profile. In some embodiments, the one or more modifications occur at positions corresponding to 137, 144, 145, 154, 155, 156, 157, 158, 159, 177, 210, 211, 212, 213, 214, 244, 245, and/or 262 of the engineered HA polypeptide (CA09 numbering). In some embodiments, the one or more modifications occur at positions corresponding to 137, 144, 145, 154, 155, 156, 157, 158, 159, 177, 210, 211, 212, 213, and/or 214 of the engineered HA polypeptide (CA09 numbering). In some embodiments, the one or more modifications comprise two or more, three or more, four or more, five or more, six or more, seven or more, eight or more, nine or more, or ten or more modifications selected from those shown in Table 4, Table 5, Table 6, Table 7, Table 8, or Table 9. In some embodiments, the one or more modifications comprise at least 2, 3, 4, 5, or 10 consecutive substitutions selected from Table 4, Table 5, Table 6, Table 7, Table 8, or Table 9.

In some embodiments, the present invention provides methods of altering the immunogenic profile of an engineered HA polypeptide comprising selecting two or more modifications selected from the group consisting of:

(i) selecting a head region of the engineered HA polypeptide, and substituting the selected head region of the engineered HA polypeptide for a corresponding head region of an HA polypeptide with a distinct immunogenic profile, (ii) identifying the presence or absence of one or more putative N-linked glycosylation sites in a head region of the engineered HA polypeptide as compared to the corresponding head region of an HA polypeptide with a distinct immunogenic profile, and introducing into the head region of the engineered HA polypeptide one or more amino acid substitutions, deletions or insertions to disrupt the one or more putative N-linked glycosylation sites or insert additional N-linked glycosylation sites in the engineered HA polypeptide based on the corresponding sequence of the HA polypeptide with a distinct immunogenic profile, (iii) introducing one or more amino acid substitutions within 15 (e.g., within 10, 9, 8, 7, 6, or 5) angstroms of the Receptor Binding Site (RBS), wherein the RBS is defined as all amino acids residues within 15 angstroms of a position corresponding to W167 (CA09 Numbering) in a three-dimensional (3-D) structure, wherein each of the one or more amino acid substitutions comprises replacing an amino acid residue at a specific position with an amino acid residue observed at the corresponding position in an HA polypeptide with a distinct immunogenic profile. Alternatively, the RBS may be defined as the epitope bound by the paratope of monoclonal antibody CH65, and the one more amino acid substitutions occur adjacent to (e.g., within 100 amino acid residues, within 75 amino acid residues, within 50 amino acid residues, within 40 amino acid residues, within 30 amino acid residues, within 25 amino acid residues, within 20 amino acid residues, within 15 amino acid residues, within 10 amino acid residues, within 5 amino acid residues, etc.) the epitope of CH65, and (iv) introducing one or more modifications selected from those shown Table 4, Table 5, Table 6, Table 7, Table 8, or Table 9, into one or more corresponding positions of the engineered HA polypeptide;

thereby generating a re-engineered HA polypeptide with altered immunogenic profile.

In various embodiments, a method according to the present invention further includes assessing expression and conformation of the re-engineered HA polypeptide.

In various embodiments, a method according to the present invention further includes a step of determining if the re-engineered HA polypeptide elicits neutralizing antibodies against seasonal and/or pandemic strains of influenza virus.

In some embodiments, generating a re-engineered HA polypeptide with altered immunogenic profile comprises increasing the binding of one or more anti-head monoclonal antibodies against seasonal and/or pandemic influenza strains. In some embodiments, generating a re-engineered HA polypeptide with altered immunogenic profile comprises increasing the breadth of binding of anti-head monoclonal antibodies against pandemic influenza strains. In some embodiments, generating a re-engineered HA polypeptide with altered immunogenic profile comprises increasing the breadth of binding of anti-stem monoclonal antibodies. In such embodiments, modifications in the head region induce an increase in binding to anti-stem monoclonal antibodies, demonstrating that substitutions at one place may exert long-range allosteric effects on a distant location. In some embodiments, increases in binding are determined by flow cytometry detection of the monoclonal antibodies bound to re-engineered HA polypeptides expressed on the surface of mammalian cells. In some embodiments, the level of monoclonal antibody bound to re-engineered HA polypeptides expressed on the surface of mammalian cells is quantified.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

FIG. 3 shows flow cytometry assay results demonstrating the proper folding and expression of recombinant HA polypeptides generated by grafting globular head regions of the influenza RBS onto recipient HA stems.

FIG. 9 shows a graphical representation of amino acid residues in the globular head region that can be modified to alter the immunological breadth of a recombinant HA polypeptide.

FIG. 10 shows flow cytometry assay results demonstrating the increased immunological breadth of recombinant HA polypeptides demonstrated by a gain of 4K8 binding to de-glycosylated constructs.

FIG. 12 shows a representative Kaplan-Meier survival curve of animals immunized with next generation DO2a modifications compared to original SMARtDO2a.

FIG. 13 shows representative weight loss curves of animals immunized with next generation DO2a modifications compared to original SMARtDO2a.

FIG. 14 shows representative viral lung titers of animals immunized with SMARtDO2a constructs compared to PBS on day 4 post viral challenge.

DEFINITIONS

Figure 1:
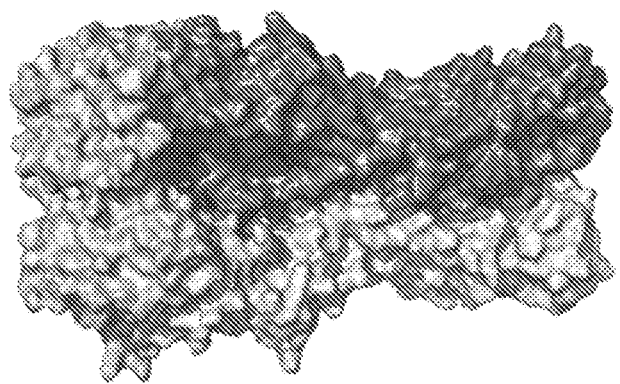
FIG. 1 shows three different regions differing in the specific residue sites at which the globular head was truncated.
Figure 1:
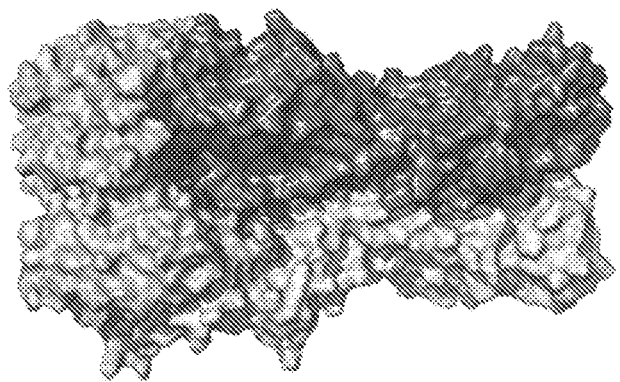
Figure 1:
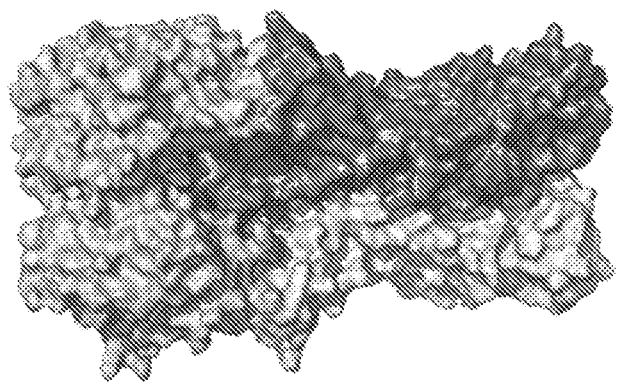

In order for the present invention to be more readily understood, certain terms are first defined below. Additional definitions for the following terms and other terms are set forth through the specification.

Adjuvant: As used herein, the term "adjuvant" refers to a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, MF59®), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules for TLR ligands. Exemplary biological adjuvants include IL-2, RANTES, GM-CSF, TNF-α, IFN-γ, G-CSF, LFA-3, CD72, B7-1, B7-2, OX-40L and 41 BBL.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to an immunoglobulin molecule produced by B lymphoid cells with a specific amino acid sequence. In some embodiments, antibodies are evoked in humans or other animals by a specific antigen (immunogen). Antibodies are characterized by reacting specifically with the antigen in some demonstrable way, antibody and antigen each being defined in terms of the other. The terms "eliciting an antibody response", "eliciting neutralizing antibody", "eliciting immunogenic response", or grammatical equivalents, refer to the ability of an antigen or other molecule to induce the production of antibodies. In some embodiments, the term "antibodies" refers to any recombinant antibodies used in in vitro assays, such as in HA screening assays, including one or more polypeptides substantially encoded by immunoglobulin genes or fragments of immunoglobulin genes. Such antibodies may exist as intact immunoglobulins or as fragments of the immunoglobulin classes, IgG, IgM, IgA, IgD and IgE, respectively. Exemplary antibody fragments include, but are not limited to, F(ab)'2, Fab', and single chain Fv (scFv).

Antigen: As used herein, the term "antigen", refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, an influenza HA polypeptide or immunogenic fragment thereof is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological activity: As used herein, the phrase "biological activity" refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest. In some embodiments, the biological activity of an HA polypeptide refers to the ability of the HA polypeptide to elicit neutralizing antibody. In these cases, the term "biological activity" is used inter-changeably with "immunogenic activity".

California 09 Numbering: As used herein, the phrase "California 09 Numbering" or "CA09 Numbering" refers to a normalized biological sequence alignment that allows the comparison of a query sequence (e.g., an engineered HA polypeptide sequence to which one or more of the modifications described herein has been or will be applied) to a subject sequence (e.g., the polypeptide sequence of A/California/07/2009 (H1N1)), thereby identifying amino acid residues in the target sequence that correspond to the same position A/California/07/2009 (H1N1) and, therefore, every other biological sequence similarly normalized to A/California/07/2009 (H1N1). In general, the target sequence and the query sequence share characteristic portions or features but differ slightly in length and/or sequence identity. For example, the numbering of residues in specific target sequence or for targeted modification can be identified and described based on the A/California/07/2009 (H1N1) protein sequence. Sequences are aligned to the full-length (including signal peptide, transmembrane and cytoplasmic tail domains) protein sequence of A/California/07/2009 (NCBI accession number: ACP44189, NCBI gi number: 227977172, 566 amino acids). The N-terminal methionine of the signal peptide is residue 1.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Characteristic Portion or Feature: As used herein, the term "characteristic portion" or "characteristic feature" is used, in the broadest sense, to refer to a portion of a substance whose presence (or absence) correlates with presence (or absence) of a particular feature, attribute, or activity of the substance. In some embodiments, a characteristic portion or feature of a substance is a portion or feature that is found in the substance and in related substances that share the particular feature, attribute or activity, but not in those that do not share the particular feature, attribute or activity. For example, the term "characteristic pandemic feature" is one that is found in at least one reference pandemic strain and not in at least one non-pandemic strain. In some embodiments, a characteristic pandemic feature is one that is commonly found in pandemic strains and rarely found in non-pandemic strains. Similarly, the term "characteristic seasonal feature" is one that is found in at least one reference seasonal strain and not in at least one non-seasonal strain. In some embodiments, a characteristic seasonal feature is one that is commonly found in seasonal strains and rarely found in non-seasonal strains. In some embodiments, a characteristic portion or feature is a "characteristic sequence element", which refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers (e.g., pandemic or seasonal). A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of continuous monomers spaced apart by one or more spacer regions whose length may or may not vary across polymers that share the sequence element. In some embodiments, a characteristic sequence element includes the presence or absence of one or more putative glycosylation sites.

Computationally Optimized Broadly Reactive Antigens (COBRA) Technology: As used herein, the terms "Computationally Optimized Broadly Reactive Antigens" or "COBRA" technology refers to the methodology and methods of designing, and resulting compounds thereof, engineered recombinant influenza HA antigens as described in, for example, pre-grant patent publications WO2012/036993, U.S. 2015/0030628, WO2013/119683, WO2013/148164, WO2014/085616, and WO2013/122827. These applications are incorporated herein by reference in their entirety.

Corresponding to: As used herein, the term "corresponding to" is often used to designate the position/identity of an amino acid residue in a polypeptide of interest (e.g., an HA polypeptide). Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190th amino acid in a particular amino acid chain but rather corresponds to the residue found at 190 in the reference polypeptide; those of ordinary skill in the art readily appreciate how to identify "corresponding" amino acids using, for example, various sequence alignment tools.

Engineered: The term "engineered", as used herein, describes a polypeptide whose amino acid sequence has been designed by person of skill in the art and/or whose existence and production require action of a person of skill in the art (i.e., "the hand of man"). For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

Epitope: As used herein, the term "epitope" includes any moiety that is specifically recognized by an immunoglobulin (e.g., antibody or receptor) binding component in whole or in part. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Head Region: As used herein, the term "head region" refers to segment encompassed by amino acid residues 59-292 (CA09 Numbering) of an engineered or wild-type HA polypeptide. Morphologically, the head region may be defined as the globular shaped domain of HA.

Hemagglutinin (HA) polypeptide: As used herein, the term "hemagglutinin polypeptide" (or "HA polypeptide') refers to a polypeptide whose amino acid sequence includes at least one characteristic sequence of HA.

A wide variety of HA sequences from influenza isolates are known in the art; indeed, the National Center for Biotechnology Information (NCBI) maintains a database (ncbi.nlm.nih.gov/genomes/FLU/) that, as of the filing of the present application included at least 15491 complete HA polypeptides from Influenza A (subtype H1N1) in the database (6974 of which are unique). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc.). For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus.

H1N1 HA polypeptide: An "H1N1 HA polypeptide", as that term is used herein, is an HA polypeptide whose amino acid sequence includes at least one sequence element that is characteristic of H1N1 and distinguishes H1N1 from other HA subtypes. Representative such sequence elements can be determined by alignments as will be understood by those skilled in the art.

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the engineered influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is a composition comprising an immunogen (such as an HA polypeptide). As used herein, "immunize" means to render a subject protected from an infectious disease, such as by vaccination.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza virus: As used herein, the term "influenza virus" refers to a segmented negative-strand RNA virus that belongs to the Orthomyxoviridae family.

Influenza vaccine: As used herein, the term "influenza vaccine" refers to an immunogenic composition capable of stimulating an immune response, administered for the prevention, amelioration, or treatment of influenza virus infection. An influenza vaccine may include, for example, attenuated or killed (e.g., split) influenza virus, virus-like particles (VLPs) and/or antigenic polypeptides (e.g., the engineered hemagglutinins described herein) or DNA derived from them, or any recombinant versions of such immunogenic materials.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Outbreak: As used herein, an influenza virus "outbreak" refers to a collection of virus isolates from within a single country in a given year.

Pandemic or seasonal strain: A "pandemic" influenza strain is one that has caused or has capacity to cause pandemic infection of human populations. In some cases, pandemic is a global outbreak of disease that occurs when a new virus appears or "emerges" in the human population, causes serious illness, and then spreads easily from person to person worldwide. In general, pandemic strains span from 2009-present and form a single cluster of antigenically similar genetic sequences to A/California/07/2009. More generally, pandemic influenza strains include those arising from reassortment (antigenic shift occurring approximately every 20-30 years) between human and avian or swine influenza viruses that result in a virus with a novel HA of avian or swine origin, against which humans lack immunity. In other words, the human population is considered to be naïve, having no or little resistance either as a result of prior vaccination or prior exposure. Pandemic and seasonal strains are antigenically distinct and by sequence quite different. In general, seasonal influenza strains may be defined as circulating strains from 1986 through to 2009 (including 2009 sequences that are not pandemic) and other strains that are substantially similar genetic sequences encoding antigenic regions (i.e., similar in antigenic sequence space). Exemplary pandemic strains include A/California/07/2009, A/California/04/2009, A/Belgium/145/2009, A/South Carolina/01/1918 and A/New Jersey/1976. Pandemic subtypes include, in particular, the H5N1, H2N2, H9N2, H7N7, H7N3, H7N9 and H10N7 subtypes. Exemplary seasonal strains include A/Texas/36/1991, A/Singapore/1986, A/New Caledonia/20/1999, A/Solomon Islands/03/2006, and A/Brisbane/59/2007 and A/Wisconsin/67/2005.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Receptor-Binding Site (RBS): As used herein, the term "receptor-binding site" or "RBS" comprises contiguous or non-contiguous amino acid residues of the head region of an influenza HA polypeptide, which include amino acids involved in direct binding of sialic acids on the target cell receptor proteins. The region of HA responsible for receptor binding resides at the membrane-distal tip of each monomer of the HA trimer, and it has several main structural features. For example, the binding site is flanked by the "220 and 130 loops", which contain amino acids that interact with sialic acid or internal sugars of the glycan chain. The membrane-distal region of the site is formed by the 190 helix, which also includes residues with the potential to contact the receptor at either the sialic acid (residue 194) or internal glycans on the receptor (approximately residues 190 and 193). The base of the site contains several highly conserved residues that form an extensive hydrogen bond network. Amino acid residues that make up a "receptor-binding site" or "RBS" of an influenza HA polypeptide may be described from a three-dimensional crystal structures of HA polypeptides complexed with sialic acid analogs and identifying amino acid residues within a certain proximity to the analog or may be described in reference to an HA polypeptide sequence from a particular viral strain (e.g., A/New Caledonia/20/99 or A/California/07/2009). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdb|1RVZ. In some embodiments, the RBS may be defined as the epitope bound by the broadly neutralizing monoclonal antibody CH65 (see, e.g., Whittle J R, et al. *Broadly neutralizing human antibody that recognizes the receptor-binding pocket of influenza virus hemagglutinin.* Proc Natl Acad Sci USA. 2011; 108:14216-21). Alternatively or additionally, the RBS may be defined as an area including all amino acid residues within 15 Angstroms of a universally conserved tryptophan corresponding to position 167 in (CA09 09 Numbering) (e.g. see Xu, R et al. Nat Struct Mol Biol. 2013 March; 20(3):363-70).

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same polypeptide (e.g., two epitopes from two separate HA polypeptides).

Recombinant influenza vaccine: As used herein, the term "recombinant influenza vaccine" refers to influenza-specific immunogenic composition comprising the engineered influenza hemagglutinins described herein, including but not limited to, influenza virus, subunit preparations thereof, virus-like particles, recombinant protein (i.e., preparations composed of recombinant HA purified to varying degree), and DNA- and viral vector-based vaccines. Recombinant influenza vaccines as described herein may optionally contain one or more adjuvants.

Recombinant hemagglutinin polypeptide: As used herein, the term "recombinant hemagglutinin (HA) polypeptide refers to any modified hemagglutinin polypeptide. In particular, the term refers to further modified or engineered hemagglutinin polypeptides.

Specificity: As is known in the art, "specificity" is a measure of the ability of a particular ligand (e.g., an antibody, an HA polypeptide, etc.) to distinguish its binding partner (e.g., an antigen, a human HA receptor, and particularly a human upper respiratory tract HA receptor) from other potential binding partners (e.g., an avian HA receptor).

Stem Region: As used herein, the term "stem region" or "stalk region" may refer to a discontinuous region of an engineered or wild-type HA polypeptide, the region comprising approximately amino acid residues 18-58 and 293-519 (CA09 Numbering). Morphologically, the stem region may be defined as the elongated domain that emerges from the globular head.

Subject: As used herein, the term "subject" means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially Similar: As used herein, the term "substantially similar" refers to a comparison between two entities. In general, entities are considered to be "substantially similar" to one another when they share sufficient structural similarity (e.g., a characteristic structural feature) that they have a comparable likelihood of sharing one or more additional attributes or features. To give but one example, a characteristic, for example, glycosylation site pattern, being either the same or similar enough between two influenza strains, that the human pandemic risk of each strain is the same.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | nonpolar | neutral | 1.8 |
|---|---|---|---|---|---|
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |

TABLE 1-continued

| Proline | Pro | P | nonpolar | neutral | -1.6 |
| Serine | Ser | S | polar | neutral | -0.8 |
| Threonine | Thr | T | polar | neutral | -0.7 |
| Tryptophan | Trp | W | nonpolar | neutral | -0.9 |
| Tyrosine | Tyr | Y | polar | neutral | -1.3 |
| Valine | Val | V | nonpolar | neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: The phrase "substantial identity" or "substantially identical" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of an HA polypeptide, reference to "substantial identity" typically refers to a HA polypeptide (or HA epitope) having an amino acid sequence at least 90%, preferably at least 91%, at least 92%, at least 93%, at least 94%, at least 95%, at least 96%, at least 97%, at least 98%, or at least 99% identical to that of a reference HA polypeptide (or HA epitope).

Vaccination: As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, an influenza VLP as described herein comprises hemagglutinin (HA) polypeptides and neuraminidase (NA) polypeptides. In some embodiments, an influenza VLP as described herein comprises HA polypeptides, NA polypeptides and/or viral structural polypeptides (e.g., an influenza structural protein such as influenza M1). In some certain embodiments, an influenza VLP as described herein comprises HA polypeptides, NA polypeptides and/or M1 polypeptides. In some embodiments, an influenza VLP as described herein comprises HA polypeptides, NA polypeptides and/or HIVgag polypeptides. As persons of skill are aware, other viral structural proteins may be used as alternatives to those exemplified herein. Influenza VLPs can be produced by transfection of host cells (e.g., mammalian cells) with plasmids encoding HA and NA proteins, and optionally HIV gag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemagglutinin content quantitation by protein staining. Other assays will be readily apparent to persons of skill upon reviewing the present disclosure.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the World Wide Web at ncbi.nlm.nih.gov/genomes/FLU/FLU.

DETAILED DESCRIPTION OF CERTAIN EMBODIMENTS

The present invention provides, among other things, methods of modifying engineered HA polypeptides to alter immune profiles and increase cross-reactivity to diverse influenza strains. Embodiments of the present invention provide various strategies for engineering HA polypeptides to extend a seasonal response profile to cover pandemic strains. In some embodiments, the strategy is designed to introduce modifications near the receptor binding site (RBS) of a host HA polypeptide based on sequences derived from an HA polypeptide with a distinct immunogenic profile. Similar strategies may be used to extend a pandemic response profile to cover seasonal strains.

HA polypeptides may be engineered to elicit a particular immunogenic response profile. In other words, the various design strategies used to generate engineered HA polypeptides can be selected or happen to result in HA polypeptides that elicit a significant immune response (e.g., a neutralizing antibody response) against predominantly circulating seasonal (i.e., endemic) influenza strains and/or historical or pandemic influenza strains. Thus, the term "seasonal response profile" may be used to describe a recombinant HA polypeptide that generates cross-neutralizing antibodies against more seasonal influenza strains than pandemic influenza strains. In general, seasonal influenza strains may be defined as circulating strains from 1986 through to 2009 (including 2009 sequences that are not pandemic) and other strains that are substantially similar genetic sequences encoding antigenic regions (i.e., similar in antigenic sequence space). Specific examples include A/New Caledonia/20/1999, and A/Wisconsin/67/2005. Thus, a "seasonal response profile" may be used to describe a recombinant HA polypeptide that generates cross-neutralizing antibodies against one or more seasonal influenza strains but not the standard pandemic strain A/California/07/2009. Likewise, the term "pandemic response profile" may be used to describe a recombinant HA polypeptide that generates cross-neutralizing antibodies against more pandemic influenza strains than seasonal influenza strains; a "pandemic response profile" may also be used to describe a recombinant HA polypeptide that generates cross-neutralizing antibodies against one or more pandemic influenza strains but not the standard seasonal strain A/New Caledonia/20/1999. In general, pandemic strains span from 2009-present and form a single cluster of antigenically similar sequences to A/California/07/2009. More generally, pandemic influenza strains include those arising from reassortment (antigenic shift occurring approximately every 20-30 years) between human and avian or swine influenza viruses that result in a virus with a novel HA of avian or swine origin, against which humans lack immunity. In other words, the human population is considered to be naïve, having no or little resistance either as a result of prior vaccination or prior exposure. Thus, pandemic strains include A/South Carolina/01/1918 and A/New Jersey/1976, which by sequence and by antigenic distance are distinct from the California 2009 cluster of sequences. Pandemic subtypes include, in particular, the H5N1, H2N2, H9N2, H7N7, H7N3, H7N9 and H10N7 subtypes.

The modifications described herein can be used to further tailor or optimize the immunogenic profile so that an engineered HA polypeptide is re-engineered to elicit antibodies against more or less seasonal strains (or demonstrate an improved or more anti-seasonal antibody response) or more or less pandemic strains (or demonstrate an improved or more anti-pandemic antibody response). Thus, these modifications extend the immune profile across clusters of sequences (or clades) of antigenically distinct strains. They can be applied to an engineered recombinant HA molecule so that it elicits an immune response against new pandemic strains arising from antigenic shift (i.e., so that they cover antigenically distinct strains that are distantly separated in genetic sequence space across extended timelines). They can also be applied to address genetic changes that occur over relatively shorter time periods so that the engineered HA polypeptide continues to be effective by eliciting an immune response against antigenically drifted circulating seasonal strains (e.g., an improved seasonal response). In particular embodiments, the modifications described herein may be used: (1) to extend coverage (i.e., capability of eliciting a neutralizing immune response) of a pandemic-like engineered HA polypeptide (i.e., a pandemic response profile) to one or more seasonal strains (i.e., a more seasonal immune profile); (2) to extend coverage of a seasonal-like engineered HA polypeptide to any pandemic strain (to address antigenic drift); and (3) to extend coverage of a seasonal-like HA polypeptide to any other antigenically distinct seasonal strains (i.e., an improved seasonal immune profile that addresses antigenic shift).

Various aspects of the invention are described in further detail in the following subsections. The use of subsections is not meant to limit the invention. Each subsection may apply to any aspect of the invention. In this application, the use of "or" means "and/or" unless stated otherwise.

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art. Although any methods and materials similar or equivalent to those described herein can be used in the practice or testing of the present invention, the preferred methods and materials are now described. All publications mentioned herein are incorporated herein by reference.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Engineered HA Polypeptides

The present invention may be used to modify any engineered hemagglutinin (HA) polypeptides including any HA polypeptides generated using various recombinant techniques. Embodiments of the present invention may be applied to the products of any method used by those of skill in the art to generate HA polypeptides with improved properties for vaccine purposes. Applicable methods to generate engineered HA polypeptides for use in embodiments of the invention include generation of HA engineered polypeptides by a computationally optimized broadly reactive antigens (COBRA) technology, mosaic technology, reverse genetics, protein engineering, influenza consensus sequences based combinations of influenza strains, deletion and/or rearrangement of structural domains, domain swapping, or combinations of neutralizing or cross-reactive epitopes among multiple influenza strains. These previous endeavors include those described in 62/005,670, WO2012/177760, WO2013/148164, US 20140147459, WO2013/043729, US 20140286981, US 2014-0050759, U.S. Pat. No. 8,685,410, WO2015/028478, US 2010-0074915, each of which is incorporated herein by reference.

However, these technologies often result in HA polypeptides that, intentionally or otherwise, have an immunogenic profile biased towards either seasonal or pandemic strains. The immunogenic profile of an HA polypeptide can be defined as the spectrum of neutralizing antibodies induced by immunization with the HA polypeptide. Typically, an HA polypeptide can have a seasonal or predominantly seasonal immune profile, a pandemic or predominantly pandemic immune profile, or a balanced immune profile. Among other things, the present invention may be used to improve the immunogenic profile of an engineered HA polypeptide such that it is capable of eliciting neutralizing antibodies against both seasonal and pandemic strains of influenza virus, or to improve the quality or quantity of neutralizing antibodies against seasonal and/or pandemic strains. In some embodiments, the present invention may be used to improve an engineered HA polypeptide such that it has a balanced immunogenic profile. Likewise, embodiments of the invention may be used alter the immune profile of an HA polypeptide with a balanced immune profile so that it become more or less seasonal, or more or less pandemic.

As used herein, the term neutralizing antibodies refers to immunoglobulin molecules produced by B lymphoid cells in humans or other animals in response to stimulation by a specific antigen (immunogen). For example, neutralizing antibodies may be induced by an influenza HA polypeptide. Neutralizing antibodies induced by a specific HA polypeptide are typically capable of neutralizing (e.g., blocking infectivity) influenza viruses containing that specific influenza HA polypeptide or influenza viruses containing related HA polypeptides that share certain common immunogenic features.

As used herein, an HA polypeptide with a seasonal or predominantly seasonal immune profile is an HA polypeptide that elicits an immune response (e.g., elicits neutralizing antibodies) against one or more seasonal strains of influenza. In some embodiments, an HA polypeptide with a seasonal or predominantly seasonal immune profile elicits antibodies that are capable of neutralizing at least 1, 2, 3, 4, 5, 6, 7, 8, 9, or 10 seasonal influenza strains. In some embodiments, an HA polypeptide with a seasonal or predominantly seasonal immune profile elicits antibodies that are capable of neutralizing 2 or more seasonal circulating influenza strains. In some embodiments, an HA polypeptide with a predominantly seasonal immune profile is an HA polypeptide that elicits antibodies that do not neutralize pandemic strains of influenza. In some embodiments, an HA polypeptide with a seasonal or predominantly seasonal immune profile elicits antibodies that do not neutralize A/California/07/2009. In some embodiments, an HA polypeptide with a seasonal or predominantly seasonal immune profile elicits antibodies that are capable of neutralizing more or substantially more seasonal influenza strains as compared to pandemic influenza strains. In some embodiments, an HA polypeptide with a seasonal or predominantly seasonal immune profile elicits antibodies that are capable of neutralizing at least 2, 3, 4, 5, etc. 6, 7, 8, 9, or 10 more seasonal influenza strains than pandemic influenza strains. In some embodiments, an HA polypeptide with a seasonal or predominantly seasonal immune profile is an HA polypeptide that elicits antibodies that are capable of neutralizing at two or more seasonal circulating strains than pandemic strains.

As used herein, an HA polypeptide with a pandemic or predominantly pandemic immune profile is an HA polypeptide that elicits an immune response (e.g., elicits neutralizing antibodies against) one or more pandemic strains of influenza. In particular, an HA polypeptide with a pandemic or predominantly pandemic immune profile is an HA polypeptide that elicits antibodies that are capable of neutralizing A/California/07/2009. In some embodiments, an HA polypeptide with a pandemic or predominantly pandemic immune profile is an HA polypeptide that elicits antibodies that are capable of neutralizing one or more of A/California/07/2009, A/South Carolina/01/1918, A/New Jersey/1976, or any other of the pandemic influenza strains as defined herein. In some embodiments, an HA polypeptide with a pandemic or predominantly pandemic immune profile elicits antibodies that are capable of neutralizing at least 1, 2, 3, 4, 5, etc. pandemic influenza strains. In some embodiments, an HA polypeptide with a pandemic or predominantly pandemic immune profile elicits antibodies that are capable of neutralizing two or more pandemic influenza strains. In some embodiments, an HA polypeptide with a pandemic or predominantly pandemic immune profile is an HA polypeptide that elicits antibodies that do not neutralize seasonal strains of influenza. In some embodiments, an HA polypeptide with a pandemic or predominantly pandemic immune profile elicits antibodies that do not neutralize A/New Caledonia/20/1999. In some embodiments, an HA polypeptide with a pandemic or predominantly pandemic immune profile elicits antibodies that are capable of neutralizing more pandemic influenza strains as compared to seasonal influenza strains. In some embodiments, an HA polypeptide with a pandemic or predominantly pandemic immune profile elicits antibodies that are capable of neutralizing at least 2, 3, 4, 5, etc. more pandemic influenza strains than seasonal influenza strains. In some embodiments, an HA polypeptide with a pandemic or predominantly pandemic immune profile is an HA polypeptide that elicits antibodies that are capable of two or more pandemic strains than seasonal strains.

As used herein, an HA polypeptide with a balanced immune profile is an HA polypeptide that elicits antibodies that are capable of neutralizing both seasonal and pandemic strains. In some embodiments, an HA polypeptide with a balanced immune profile is an HA polypeptide that elicits antibodies that are capable of neutralizing at least 1, 2, 3, 4, or 5 seasonal strains (e.g., A/New Caledonia/20/1999) as well as one or more of A/California/07/2009, A/South Carolina/01/1918, A/New Jersey/1976, or any of the other pandemic strains described herein. In some embodiments, an HA polypeptide with a balanced immune profile is an HA polypeptide that elicits antibodies that are capable of neutralizing at least 1, 2, 3, 4, or 5 seasonal strains as well as A/California/07/2009. In some embodiments, an HA polypeptide with a balanced immune profile is an HA polypeptide that elicits antibodies that are capable of neutralizing A/New Caledonia/20/1999 and A/California/07/2009. In some embodiments, an HA polypeptide with a balanced immune profile is an HA polypeptide that elicits antibodies that are capable of neutralizing substantially the same numbers of seasonal and pandemic strains. For example, the difference in the numbers of seasonal and pandemic strains neutralized by antibodies elicited by an HA polypeptide with a balanced immune profile is no greater than 1, 2, 3, 4, or 5.

As used herein, the phrases "improve an immunogenic profile", "increase the breath of an immune profile", "more balanced immune profile", "less biased immune profile", "more seasonal", "less seasonal", "more pandemic", "less pandemic", or grammatical equivalents, indicate the spectrum of neutralizing antibodies generated by an modified HA polypeptide relative to the spectrum of a reference HA polypeptide, such as the parent HA polypeptide before modifications described herein.

Modifying Engineered HA to Alter Immunogenic Profile

Embodiments of the invention may be used to modify or alter the immunogenic profile of engineered HA polypeptides, in particular, to broaden the diversity of influenza strains against which an engineered HA polypeptide is capable of eliciting an immune response (e.g., a neutralizing antibody response). In some embodiments, a method according to the present invention is based on modifications deduced from in silico analysis of sequence variation among circulating influenza strains, mapping of antigenic region(s), and/or epitope patterns and structural analyses of the HA peptide relative to HA polypeptides with different or distinct immune profiles. Targeted modifications can be introduced at various amino acid residue locations and/or specific regions of an HA polypeptide with known immune profile, based on corresponding sequences derived from an HA polypeptide with distinct immune profile, to yield novel HA polypeptides with improved and more balanced immune profile. The location, type and number of modifications can be selected and combined to generate a re-engineered HA polypeptide with an immunogenic profile that has been tailored to elicit a particular immune response (e.g., a balanced immune profile, an improved "more pandemic" response against pandemic strains, etc.). In some embodiments, a modification strategy is designed to generally preserve specific residues of the receptor binding site (RBS) of a host HA polypeptide with modifications engineered in the region near the RBS. Exemplary modification strategies are described below.

Unless stated otherwise, specific positions for modifications (e.g., amino acid substitutions, deletions or insertions) in a target HA polypeptide are determined by reference to the A/California/07/2009 (H1N1) HA polypeptide sequence provided below (CA09 Numbering):

```
                                          (SEQ ID NO: 2)
MKAILVVLLYTFATANADTLCIGYHANNSTDTVDTVLEKNVTVTHSVNLLE

DKHNGKLCKLRGVAPLHLGKCNIAGWILGNPECESLSTASSWSYIVETPSS

DNGTCYPGDFIDYEELREQLSSVSSFERFEIFPKTSSWPNHDSNKGVTAAC
```

-continued
```
PHAGAKSFYKNLIWLVKKGNSYPKLSKSYINDKGKEVLVLWGIHHPSTSAD

QQSLYQNADAYVFVGSSRYSKKFKPEIAIRPKVRXXEGRMNYYWTLVEPGD

KITFEATGNLVVPRYAFAMERNAGSGIIISDTPVHDCNTTCQTPKGAINTS

LPFQNIHPITIGKCPKYVKSTKLRLATGLRNIPSIQSRGLFGAIAGFIEGG

WTGMVDGWYGYHHQNEQGSGYAADLKSTQNAIDEITNKVNSVIEKMNTQFT

AVGKEFNHLEKRIENLNKKVDDGFLDIWTYNAELLVLLENERTLDYHDSNV

KNLYEKVRSQLKNNAKEIGNGCFEFYHKCDNTCMESVKNGTYDYPKYSEEA

KLNREEIDGVKLESTRIYQILAIYSTVASSLVLVVSLGAISFWMCSNGSLQ

CRICI
```

Grafting Engineered Head Region

In some embodiments, a method of altering the immunogenic profile of an engineered HA polypeptide is based on grafting structurally-defined regions of the globular head of an HA polypeptide with a known immune profile onto the stem regions of HA polypeptides with distinct immune profiles. For example, a method according to the invention may involve selecting a head region of an engineered HA polypeptide with a known immune profile and substituting the selected head region of the engineered HA polypeptide for a corresponding head region of an HA polypeptide with a distinct immunogenic profile. In some embodiments, a selected head region of an engineered HA polypeptide with a predominantly seasonal immune profile may be grafted onto the stem regions of the HA polypeptide with a predominantly pandemic immune profile. Conversely, in some embodiments, a selected head region of an engineered HA polypeptide with a predominantly pandemic immune profile may be grafted onto the stem regions of the HA polypeptide with a predominantly seasonal immune profile.

In some embodiments, the structurally-defined regions of the globular head of the HA polypeptide with a known immune profile are grafted onto a region of an HA polypeptide with a distinct immune profile, wherein the region comprises the stem region plus a fraction of the head region of the HA polypeptide with a distinct immune profile. In other embodiments, the entire globular domain of the HA with a known immune profile is grafted onto the stem region of an HA molecule with distinct immunological profile. In general, the head region suitable for grafting is selected to ensure the preservation of the structural integrity of the resulting full-length hybrid molecule. Typically, a suitable head region is selected to preserve the Receptor-binding Site (RBS) of an HA polypeptide. The RBS of an HA polypeptide can generally be defined as the epitope recognized by the CH65 antibody (see e.g. Whittle J R, et al. Proc Natl Acad Sci USA. 2011; 108:14216-21). Alternatively, the RBS may be defined as an area including all amino acid residues within 15 angstroms of a universally conserved tryptophan corresponding to position 167 (CA09 Numbering) (e.g. see Xu, R et al. Nat Struct Mol Biol. 2013 March; 20(3):363-70.) A suitable head region comprising or consisting of the RBS can be selected for grafting onto stem recipients based on the preservation of secondary structure, the compact globular configuration of the detached RBS, and preservation of interface contacts upon integration of the donor RBS in the recipient stem molecule. Non-limiting examples of head regions selected from an engineered HA polypeptide with a predominantly seasonal immune profile suitable for grafting are described in Example 1. In some embodiments, an HA polypeptide with predominantly seasonal immune profile has an amino acid sequence substantially identical to that shown in SEQ ID NO: 1.

(SEQ ID NO: 1)
MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

In some embodiments, a suitable head region is selected to contain an amino acid sequence corresponding to residues 63-278, 125-277 or 135-269 of SEQ ID NO:1. As used herein, the term "corresponding to" is used to designate the position/identity of an amino acid residue in an HA polypeptide of interest. Those of ordinary skill will appreciate that, for purposes of simplicity, residues in an HA polypeptide are designated using a canonical numbering system based on a reference related polypeptide, so that an amino acid "corresponding to" a residue at position 63, for example, need not actually be the 63th amino acid in a particular amino acid chain but rather corresponds to the residue found at 63 in the reference polypeptide; those of ordinary skill in the art readily appreciate how to identify "corresponding" amino acids using, for example, various sequence alignment tools. In some embodiments, a suitable head region may contain an amino acid sequence at least 90%, 91%, 92%, 93%, 94%, 95%, 96%, 97%, 98%, or 99% identical to amino acid residues 63-278, 125-277 or 135-269 of SEQ ID NO:1.

A selected head region may then be used to substitute or replace a corresponding head region of an HA polypeptide with distinct immune profile, i.e., pandemic or predominantly pandemic. Such a suitable HA polypeptide with distinct immune profile (i.e., pandemic or predominantly pandemic) may be naturally-occurring or engineered including, but not limited to, those engineered by a computationally optimized broadly reactive antigens (COBRA) technology, mosaic technology, reverse genetics, protein engineering, influenza consensus sequences based combinations of influenza strains, deletion and/or rearrangement of structural domains, domain swapping, or combinations of neutralizing or cross-reactive epitopes among multiple influenza strains.

For example, a selected head region may be used to substitute or replace a corresponding head region of a naturally-occurring pandemic strain selected from: residues of 63-277 of SEQ ID NO:2 [full-length wt CA09 (A/California/07/2009 HA sequence) sequence], residues of 63-277 of SEQ ID NO: 3 [full-length wt SC1918 sequence], residues 63-277 of SEQ ID NO: 4 [full-length wt NJ1976 sequence], residues 125-277 of SEQ ID NO: 2 [full-length wt CA09 sequence], residues 125-277 of SEQ ID NO: 3 [full-length wt SC1918 sequence], residues 125-277 of SEQ ID NO: 4 [full-length wt NJ1976 sequence], residues 135-269 of SEQ ID NO: 2 [full-length wt CA09 sequence], residues 135-269 of SEQ ID NO: 3 [full-length wt SC1918 sequence], or residues 135-269 of SEQ ID NO: 4 [full-length wt NJ1976 sequence].

In some embodiments, a selected head region may be used to substitute or replace a corresponding head region of an engineered HA polypeptide with a distinct immunogenic profile, which is predominantly pandemic. As a non-limiting example, an engineered HA polypeptide with a predominantly pandemic immune profile has amino acid sequence substantially identical to SEQ ID NO: 6

MKAKLLVLLCTFTATYADTICIGYHANNSTDTVDTVLEKNVTVTHSVNLLE

DSHNGKLCKLKGIAPLQLGKCSVAGWILGNPECESLSTASSWSYIVETSSP

DNGTCYPGYFADYEELREQLSSVSSFERFEIFPKTSSWPNHDSNGVTASCP

HAGAKSFYRNLLWLVKKGNSYPKLSKSYINDKGKEVLVLWGVHHPSTSADQ

QSLYQNANAYVSVVTSRYSRRFTPEIAIRPKVRDQEGRMNYYWTLVEPGDT

IIFEATGNLIAPWYAFALSRGFGSGIITSDTPVHDCNTTCQTPQGAINSSL

PFQNVHPVTIGECPKYVRSAKLRMATGLRNIPSIQSRGLFGAIAGFIEGGW

TGMVDGWYGYHHQNEQGSGYAADLKSTQNAIDGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNNTCMESVKNGTYDYPKYSEESK

LNREKIDGVKLESMGVYQILAIYSTVASSLVLLVSLGAISFWMCSNGSLQC

RICI.

A suitable head region is selected to contain an amino acid sequence corresponding to residues 63-278, 125-277 or 135-269 of SEQ ID NO: 6.

Modifications to Remove or Engineer Putative N-Linked Glycosylation Sites

In some embodiments, a method of altering the immunogenic profile of an engineered HA polypeptide is based on modifications to residues associated with predicted or putative N-linked glycosylation sites in the globular head region of an HA polypeptide. Typically, putative or predicted N-linked glycosylation sites are defined by a consensus sequence of NxS/Ty, wherein x and y are not P. Seasonal HA polypeptides typically contain additional N-linked glycosylation sites in the region of the receptor-binding site (RBS) relative to pandemic or pandemic-like HA polypeptides. Specific amino acid residues in a target seasonal or seasonal-like engineered HA polypeptide may be mutated to ablate glycosylation sites and give the engineered HA polypeptide a more pandemic glycosylation profile. In specific embodiments, specific amino acid residues in the target seasonal or season-like engineered HA polypeptide may be mutated or substituted to those observed at corresponding positions in pandemic or pandemic-like HA polypeptides (e.g., California/07/2009) in order to alter the glycosylation and immunogenic profiles of the target HA polypeptide to be more pandemic.

Thus, in some embodiments, a method according to the present invention involves identifying the presence or absence of one or more putative N-linked glycosylation sites in a head region of an engineered HA polypeptide with a known immune profile as compared to the corresponding head region of an HA polypeptide with a distinct immunogenic profile; introducing into the head region of the engineered HA polypeptide one or more amino acid substitutions, deletions or insertions to disrupt the one or more putative N-linked glycosylation sites or insert additional N-linked glycosylation sites based on the corresponding sequence of the HA polypeptide with a distinct immunogenic profile.

In some embodiments, one or more amino acid substitutions, deletions or insertions are introduced into an engineered HA polypeptide with a predominantly seasonal immune profile to disrupt one or more putative N-linked glycosylation sites such that re-engineered HA polypeptide is altered to be more pandemic. Conversely, in some embodiments, one or more amino acid substitutions, deletions or insertions are introduced into an engineered HA polypeptide with a predominantly pandemic immune profile to insert one or more putative N-linked glycosylation sites such that the re-engineered HA polypeptide is altered to be more seasonal.

In some embodiments, putative N-linked glycosylation sites are removed or added at or near the Receptor Binding Site (RBS) region. In some embodiments, the putative N-linked glycosylation sites may be found within 15 (e.g., within 10, 9, 8, 7, 6, or 5) angstroms of the Receptor Binding Site (RBS), wherein the RBS is defined as all amino acid residues within 15 (e.g., within 10, 9, 8, 7, 6, or 5) angstroms of a position corresponding to W167 (CA09 Numbering) in a three-dimensional (3-D) structure. In specific embodiments, the predicted N-Linked glycosylation sites may correspond to positions 142-145 and/or 177-179 (CA09 Numbering).

Thus, a recombinant HA polypeptide which elicits a balanced immune profile can be generated through amino acid substitution, disruption or deletion to disrupt or remove an N-linked glycosylation site in an HA polypeptide with a predominantly seasonal immune profile. Alternatively, a recombinant HA polypeptide which elicits a balanced immune profile can be generated through amino acid substitutions, disruption or deletion to introduce an N-linked glycosylation site into an HA polypeptide with a predominantly pandemic immune profile. Examples of amino acid substitutions, disruption or deletions that can be performed to generate a recombinant HA polypeptide which elicits a balanced immune profile can be found in Table 4 or Table 5. The amino acid substitutions, disruption or deletions can be derived from corresponding regions of a circulating influenza strain.

Targeted substitutions or deletions in N-linked glycosylation sites can be combined with one or more additional modifications. For example, positively charged amino acid residues can be inserted near the RBS to create a re-engineered HA polypeptide with a more pandemic immune profile. In specific embodiments, an engineered HA polypeptide with a seasonal or predominantly seasonal immune profile can be made to have more pandemic (e.g., more balanced) immune profile through insertions of one or more positively charged amino acids near or adjacent to one or more putative N-linked glycosylation sites of, or into the conformational loop structures bounding the RBS (e.g., into the "220 and 130 loops"; see, e.g., Bradley, K. C. et al., J. Virol., 2011, 85(23), 12387-12398). In some embodiments, a Lysine or Arginine residue is inserted into a loop or loops bounding the RBS ("lysine loop insertion"). In some embodiments, loop insertions may comprise an insertion of Lysine (K) or Arginine (R) at or near positions corresponding to residue 147 (CA09 Numbering) of the target engineered HA polypeptide. For example, loop insertions may comprise insertion of a Lysine (K) or Arginine (R) residue within 1-5 (e.g., within 1-4, 1-3, 1-2 amino acids) amino acids of the NxS/Ty consensus sequence. In some embodiments, the Lysine (K) or Arginine (R) residue is within 1-5 amino acids (e.g., within 1-4, 1-3, 1-2 amino acids) 5' or 3' of the NxS/Ty consensus sequence.

Targeted Modifications to Residues in the RBS Region

In some embodiments, altering the immunogenic profile of an engineered HA polypeptide may be accomplished by introducing one or more amino acid substitutions in the region of or adjacent to the RBS region. For example, one or more amino acid substitutions may be introduced at amino acid positions within a region encompassing residues corresponding to 60 and 291 of (CA09 Numbering) of the target engineered HA polypeptide. One or more amino acid substitutions may also be introduced within 15 (e.g., within 10, 9, 8, 7, 6, 5, etc.) angstroms of the Receptor Binding Site (RBS), wherein the RBS is defined as all amino acids residues within 15 (e.g., within 10, 9, 8, 7, 6, 5, etc.) angstroms of a position corresponding to conserved residue W167 (CA09 Numbering) in a three-dimensional (3-D) structure. For example, in embodiments where the modifications occur within 10 angstroms of the RBS, they occur between 15-25 angstroms from the conserved W167. In some embodiments, the RBS may be defined by epitope bound by broadly neutralizing monoclonal antibody CH65 (see, e.g., Whittle J R, et al. *Broadly neutralizing human antibody that recognizes the receptor-binding pocket of influenza virus hemagglutinin*. Proc Natl Acad Sci USA. 2011; 108:14216-21). In such embodiments, the one more amino acid substitutions occur adjacent to (e.g., within 100 amino acid residues, within 75 amino acid residues, within 50 amino acid residues, within 40 amino acid residues, within 30 amino acid residues, within 25 amino acid residues, within 20 amino acid residues, within 15 amino acid residues, within 10 amino acid residues, within 5 amino acid residues, etc.) the epitope of CH65, or within 15 angstroms of the epitope of CH65. In some embodiments, each amino acid substitution comprises replacing an amino acid residue at a specific position with an amino acid residue observed at the corresponding position in an HA polypeptide with a distinct immunogenic profile (e.g., a circulating seasonal or pandemic influenza strain). For example, an engineered HA polypeptide with a predominantly seasonal immune profile may be altered to be more pandemic by substituting amino acids at specific positions based on amino acid residues that occur at the corresponding positions of an HA polypeptide with a predominantly pandemic immune profile. Conversely, an engineered HA polypeptide with a predominantly pandemic immune profile may be altered to be more seasonal by substituting amino acids at specific positions based on amino acid residues that occur at the corresponding positions of an HA polypeptide with a predominantly seasonal immune profile.

Exemplary amino acid substitutions are shown in Table 4, Table 5, Table 6, Table 7, Table 8, or Table 9. As non-limiting examples, one or more amino acid substitutions may occur at positions in the target HA polypeptide corresponding to 137, 144, 145, 154, 155, 156, 157, 158, 159, 177, 210, 211, 212, 213, 214, 244, 245, and/or 262 (CA09 Numbering). In particular embodiments, one or more amino acid substitutions may occur at positions corresponding to 137, 144, 145, 154, 155, 156, 157, 158, 159, 177, 210, 211, 212, 213, and/or 214 (CA09 Numbering). In some embodiments, one or more modifications comprise two or more, three or more, four or more, five or more, six or more, seven or more, eight or more, nine or more, or ten or more modifications selected from those shown Table 4, Table 5, Table 6, Table 7, Table 8, or Table 9. In some embodiments, one or more modifications may include at least 2, 3, 4, 5, 6, 7, 8, 9, or 10 consecutive substitutions selected from Table 4, Table 5, Table 6, Table 7, Table 8, or Table 9.

A combination of various methods described herein may be used to alter the immunogenic profile of an engineered HA polypeptide. For example, targeted modifications to residues in the region of the RBS can be used in combination with modifications to putative N-linked glycosylation sites and loop insertion(s). Head region grafting may also be used in combination with targeted modifications to residues around the RBS, and/or modifications to putative N-linked glycosylation sites and loop insertion(s).

Evaluation of Re-Engineered HA Polypeptides

In some embodiments, modified recombinant HA polypeptides generated according to various methods described herein may be assessed for desired expression and conformation. Screening methods are well known to the art and include cell-free, cell-based, and animal assays. In vitro assays can be either solid state or soluble target molecule detection may be achieved in a number of ways known to the art, including the use of a label or detectable group capable of identifying an engineered HA polypeptide which is bound to a target molecule (e.g., immunoglobulin). Detectable labels may be used in conjunction with assays using engineered HA polypeptides of the present invention. For example, recombinant HA polypeptide as described herein may be selected based on expression and conformational characteristics as determined by assays described in International Patent Application PCT/US2015/033205 entitled "Expression and Conformational Analysis of Engineered Influenza Hemagglutinin" filed on May 29, 2015.

The present invention provides methods for testing recombinant HA polypeptides in accordance with the invention in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In some embodiments, an animal host used for the invention is a ferret. In particular, in some embodiments, an animal host is naïve to viral exposure or infection prior to administration of a binding agent in accordance with the invention (optionally in a composition in accordance with the invention). In some embodiments, the animal host is inoculated with, infected with, or otherwise exposed to virus prior to or concurrent with administration of a recombinant HA polypeptide in accordance with the invention. An animal host used in the practice of the present invention can be inoculated with, infected with, or otherwise exposed to virus by any method known in the art. In some embodiments, an animal host may be inoculated with, infected with, or exposed to virus intranasally.

Modified recombinant HA polypeptides of the present invention may also be assessed in screening assays to identify and/or select those that can elicit a protective (i.e., neutralizing) immune response antibodies against both seasonal and pandemic strains of influenza virus in an animal (e.g., a mouse, ferret or human). In particular embodiments, elicitation of a protective immune response can be ascertained, for example, by using the generally known hemagglutination inhibition assay (HAI) as a surrogate measure of influenza vaccine efficacy. HAI assays may use chicken, turkey or horse erythrocytes for the detection of antibodies specific for H1N1. In particular embodiments, protective immune responses are demonstrated by eliciting an average HAI titer of greater than 1:40, which has been correlated with prevention and reduction of influenza illness. HAI antibody titers of approximately 1:32 to 1:40 will generally protect about 50% of subjects from infection after immunization with inactivated human influenza virus vaccine. See Treanor, J. & Wright, P. F. *Immune correlates of protection against influenza in the human challenge model*. Dev. Biol. (Basel), 2003, 115:97-104; incorporated by reference herein). In some embodiments, elicitation of a protective immune response can by identified by seroconversion rates. A protective level of seroconversion may be defined as at least a 4-fold rise in HAI titer, for example, a pre-administration or vaccination HAI titer of less than 1:10 and a post vaccinate titer of greater than or equal to 1:40. In other words, successful rates of seroconversion may be defined as the percentage of subjects with either a pre-vaccination HAI titer less than about 1:10 and a post-vaccination HAI titer of greater than about 1:40 or a pre-vaccination HAI titer greater than about 1:10 and a minimum four-fold rise in post-vaccination HAI antibody titer.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey et al., 2007, Science 315; 655-59; incorporated herein by reference). Virus transmission studies may be used to test recombinant HA polypeptides in accordance with the invention. For example, recombinant HA polypeptides in accordance with the invention may be administered to a suitable animal host in order to determine the efficacy of said engineered HA polypeptide in eliciting a broad immune response in the animal host. Using information gathered from studies in an animal host, one may predict the efficacy of a recombinant HA polypeptide to elicit broadly protective in a human host.

Nucleic Acid Construction and Expression

Recombinant influenza HA polypeptides as described herein may be produced from nucleic acid molecules using molecular biological methods known to the art. Nucleic acid molecules are inserted into a vector that is able to express the HA polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

In some embodiments, the present invention provides nucleic acids which encode an HA polypeptide or a characteristic or biologically active portion of an HA polypeptide. In some embodiments, the invention provides nucleic acids which are complementary to nucleic acids which encode an HA polypeptide or a characteristic or biologically active portion of an HA polypeptide.

In some embodiments, the invention provides nucleic acid molecules which hybridize to nucleic acids encoding an HA polypeptide or a characteristic or biologically active portion of an HA polypeptide. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In some embodiments, nucleic acids can be DNA or RNA, and can be single stranded or double-stranded. In some embodiments, nucleic acids in accordance with the invention may include one or more non-natural nucleotides; in some embodiments, nucleic acids in accordance with the invention include only natural nucleotides.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS, 293 or CHO cell). Host cells transformed with an expression vector are grown under conditions permitting production of an engineered HA polypeptide the present invention followed by recovery of an engineered HA polypeptide.

Recombinant HA polypeptides of the present invention may be purified by any technique known in the art. For example, not wishing to be bound by theory, engineered HA polypeptides may be recovered from cells either as soluble polypeptides or as inclusion bodies, from which they may be extracted quantitatively by 8M guanidinium hydrochloride and dialysis. In order to further purify recombinant HA polypeptides of the present invention, conventional ion exchange chromatography, hydrophobic interaction chromatography, reverse phase chromatography or gel filtration may be used. Recombinant HA polypeptides of the present invention may also be recovered from conditioned media following secretion from eukaryotic or prokaryotic cells.

Influenza Virus-Like Particles (VLPs)

In some embodiments, the present invention provides for influenza virus-like particles (VLPs) including a modified recombinant HA polypeptide as described herein. The influenza VLPs are, in some embodiments, generally made up of HA, NA and virus structural (e.g., HIV gag) proteins. Production of influenza VLPs is known in the art and will be readily apparent to persons of skill upon reading the present disclosure. For example, influenza VLPs may be produced by transfection of host cells with plasmids encoding the HA, NA and HIV gag proteins. To give but one example, a suitable host cell includes a human cell (e.g., HEK293T). After incubation of the transfected cells for an appropriate time to allow for protein expression (such as for approximately 72 hours), VLPs may be isolated from cell culture supernatants. In some embodiments, influenza VLPs as disclosed herein may be used as influenza vaccines to elicit a broadly neutralizing immune response against H1N1 influenza viruses.

Pharmaceutical Compositions

In some embodiments, the present invention provides for pharmaceutical compositions including a modified recombinant HA polypeptide as described herein and/or related entities. For example, in some embodiments, modified recombinant HA polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions in accordance with the invention.

In some embodiments, the present invention provides methods of preventing or treating influenza infections by administration of such pharmaceutical compositions in accordance with the invention. In some embodiments, pharmaceutical compositions in accordance with the invention are administered to a subject suffering from or susceptible to an influenza infection. In some embodiments, a subject is an animal, including but not limited to birds (e.g., chickens, ducks, turkeys, etc.), dogs, horses and pigs. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to modified recombinant HA polypeptides in accordance with the invention prior to, during, or after administration of pharmaceutical compositions in accordance with the invention. In some embodiments, subjects having such antibodies are not administered pharmaceutical compositions comprising modified recombinant HA polypeptides in accordance with the invention. In some embodiments, an appropriate dose of pharmaceutical composition and/or modified recombinant HA polypeptide is selected based on detection (or lack thereof) of such antibodies.

In some embodiments, selection of a particular subject for treatment, particular modified recombinant HA polypeptide or composition for administration, and/or particular dose or regimen for administration, is memorialized, for example in a written, printed, or electronic storage form.

Compositions comprising a modified recombinant HA polypeptide as described may be administered prior to or after development of one or more symptoms of influenza infection. In some embodiments, influenza VLPs comprising a modified recombinant HA polypeptide as described herein (or a modified recombinant HA polypeptide itself) may be administered prior to or after development of one or more symptoms of influenza infection.

In some embodiments, the present invention provides for treatment of influenza infections by administration of modified recombinant HA polypeptides described herein. In some embodiments, treatment of influenza infections according to the present invention is accomplished by administration of an influenza VLP comprising a modified recombinant HA polypeptide as described herein. In some embodiments, treatment of influenza infections according to the present invention is accomplished by administration of a vaccine. To date, although significant accomplishments have been made in the development of influenza vaccines, there is room for further improvement. The present invention provides vaccines comprising modified recombinant HA polypeptides in accordance with the invention, and particularly comprising engineered HA polypeptides that elicit broadly protective immune responses to multiple neutralizing antigenic determinants (e.g., epitope) of the modified recombinant HA polypeptides.

In some embodiments, the present invention provides an influenza VLP, an influenza vaccine, a fusion protein and/or a modified recombinant HA polypeptide as described herein for influenza prophylactics.

In some embodiments, the present invention provides for immunogenic compositions (e.g., vaccines) and the administration of these immunogenic compositions to a human subject. In particular embodiments, a human subject is 6 months of age or older, is 6 months through 35 months of age, is 36 months through 8 years of age, or 9 years of age or older. In some embodiments, the immunogenic compositions are pharmaceutical compositions comprising one or more of the following: (1) inactivated virus, (2) live attenuated influenza virus, for example, replication-defective virus, (3) virus-like particles (VLPs), (4) modified recombinant HA polypeptide, (5) nucleic acid encoding a modified recombinant HA polypeptide or characteristic or biologically active portion thereof, (6) DNA vector that encodes a modified recombinant HA polypeptide in accordance with the invention or characteristic or biologically active portion thereof, and/or (7) expression system, for example, cells expressing one or more influenza proteins to be used as antigens.

Whole influenza viruses comprising the engineered and re-engineered HA polypeptides described herein can be produced by plasmid-based reverse genetics (see, e.g., Neumann, G. et la., *Reverse Genetics of Influenza Viruses*, Methods Mol Biol., 2012, 865:193-206; incorporated by reference herein) and egg-based technologies; e.g. a recombinant virus comprising a computationally optimized H1 HA polypeptide as described herein, a wild-type NA polypeptide from an H1N1 influenza strain and a backbone of internal protein genes from a donor virus (e.g., influenza A/Puerto Rico/8/34 (PR8)) that confers a high yield in eggs. For example, six plasmids encoding the internal proteins of the high-growth influenza A/Puerto Rico/8/34 (PR8) donor virus can be co-transfected with two plasmids encoding a computationally optimized H1N1 HA polypeptide as described herein and a wild-type neuraminidase (NA) glycoprotein into qualified mammalian cells (e.g., Vero cells), followed by isolation of the recombinant virus. Those of skill in the art will appreciate the 12-plasmid reverse genetics systems may also be used (see, e.g., Pekosz, A. et al. *Reverse genetics of negative-strand RNA viruses: Closing the circle.* Proc. Natl. Acad. Sci., 1999, 96, 884-8806). Recombinant viruses containing internal protein genes from the PR8 virus may be used to prepare inactivated influenza virus vaccines (see, e.g., Fodor, E. et al. *Rescue of influenza A virus from Recombinant DNA. J. Virol.,* 1999, 73, 9679-9682; incorporated by reference herein). Whole influenza viruses can be administered as components of a live-attenuated or split-inactivated vaccine.

Thus, in some embodiments, the present invention provides inactivated flu vaccines. In some embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate). Inactivation can occur after or prior to clarification of allantoic fluid (from virus produced in eggs); the virions are isolated and purified by centrifugation (Nicholson et al., eds., 1998, Textbook of Influenza, Blackwell Science, Malden, Mass.; incorporated herein by reference). To assess the potency of the vaccine, the single radial immunodiffusion (SRD) test can be used (Schild et al., 1975, Bull. World Health Organ., 52:43-50 & 223-31; Mostow et al., 1975, J. Clin. Microbiol., 2:531; both of which are incorporated herein by reference).

In some embodiments, engineered or re-engineered HA polypeptides of the present invention are used as a component of seasonal and/or pandemic influenza vaccines or as part of an influenza vaccination regimen intended to confer long-lasting (multi-season) protection.

In some embodiments, influenza virus for use in vaccines is grown in eggs, for example, in embryonated hen eggs, in which case the harvested material is allantoic fluid. Alternatively or additionally, influenza virus or engineered/re-engineered hemagglutinin polypeptides may be produced from any method using tissue culture to grow the virus. Suitable cell substrates for growing the virus or otherwise recombinantly producing the engineered or re-engineered hemagglutinin polypeptides include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Engineered or re-engineered hemagglutinin polypeptides may also be expressed/produced in diverse eukaryotic-based expression systems, including microalgae (e.g. Schizochytrium sp.; see, e.g., Bayne, A-C.V. et al., PLOS ONE, 8(4):e61790, April 2013), plant-based systems (e.g., tobacco plants; see, e.g., Jul-Larsen, A., et al., Hum Vaccin Immunother., 8(5):653-61, 2012), yeast (see, e.g., Athmaram, T. N. et al., Virol J., 8:524, 2011), and fungi (see, e.g., Allgaier, S. et al., Biologicals, 37:128-32, 2009). Bacterial based expression systems are also encompassed by the present invention (see, e.g., Davis, A. R. et al., Gene, 21:273-284, 1983).

In some embodiments, vaccines in accordance with the invention further comprise one or more adjuvants. For example, aluminum salts (Baylor et al., 2002, Vaccine, 20:S18; incorporated herein by reference) and monophosphoryl lipid A (MPL; Ribi et al., 1986, Immunology and Immunopharmacology of Bacterial Endotoxins, Plenum Publ. Corp., N.Y., p. 407; incorporated herein by reference) can be used as adjuvants in human vaccines.

Alternatively or additionally, new compounds are currently being tested as adjuvants in human vaccines, such as MF59 (Chiron Corp., chiron.com/investors/pressreleases/2005/051028), CPG 7909 (Cooper et al., 2004, Vaccine, 22:3136; incorporated herein by reference), and saponins, such as QS21 (Ghochikyan et al., 2006, Vaccine, 24:2275; incorporated herein by reference).

Additionally, some adjuvants are known in the art to enhance the immunogenicity of influenza vaccines, such as poly[di(carboxylatophenoxy)phosphazene] (PCCP; Payne et al., 1998, Vaccine, 16:92; incorporated herein by reference), interferon-γ (Cao et al., 1992, Vaccine, 10:238; incorporated herein by reference), block copolymer P1205 (CRL1005; Katz et al., 2000, Vaccine, 18:2177; incorporated herein by reference), interleukin-2 (IL-2; Mbwuike et al., 1990, Vaccine, 8:347; incorporated herein by reference), and polymethyl methacrylate (PMMA; Kreuter et al., 1981, J. Pharm. Sci., 70:367; incorporated herein by reference).

In addition to immunogenic compositions (e.g., vaccines comprising VLPs with the engineered or re-engineered influenza hemagglutin polypeptides described herein), the present invention provides other therapeutic compositions useful in the treatment of viral infections. Therapeutic compositions include, for example, influenza VLPs, fusions proteins, and an engineered or re-engineered HA polypeptide itself as described herein. In some embodiments, treatment is accomplished by administration of an agent that interferes with expression or activity of an HA polypeptide.

In some embodiments, immunogenic compositions (e.g., influenza VLPs or engineered/re-engineered HA polypeptides themselves) as described herein are administered alone or in combination with one or more therapeutic agents to enhance an immune response. For example, in some embodiments, influenza VLPs as described herein may be administered with an adjuvant, such as Freund incomplete adjuvant or Freund's complete adjuvant. In some embodiments, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, may be used as biological adjuvants (e.g., Salgaller et ah, 1998, J. Surg. Oncol. 68(2): 122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90).

In some embodiments, the present invention provides pharmaceutical compositions comprising antibodies or other agents related to provided HA polypeptides. For example, the invention provides compositions containing antibodies that recognize virus particles containing a particular engineered or re-engineered HA polypeptide, nucleic acids (such as nucleic acid sequences complementary to HA sequences, which can be used for RNAi), glycans that compete for binding to HA receptors, small molecules or glycomimetics that compete the glycan-HA polypeptide interaction, or any combination thereof. In some embodiments, collections of different agents, having diverse structures are utilized. In some embodiments, therapeutic compositions comprise one or more multivalent agents. In some embodiments, treatment comprises urgent administration shortly after exposure or suspicion of exposure.

In some embodiments, any of the immunogenic compositions (e.g., vaccines) described herein offer broad cross-protection against different varieties of influenza viruses. For example, in some embodiments, immunogenic compositions described herein offer cross-protection against avian, swine and/or human-adapted influenza A viruses. In some embodiments, any of the immunogenic compositions described herein offer cross-protection against one or more influenza A subtypes. In some embodiments, the immunogenic compositions described herein provide cross-protection against multiple strains of influenza A H1-subtype viruses (see, e.g., FIGS. 4 and 5).

In general, immunogenic and/or pharmaceutical composition will include a therapeutic agent in addition to one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc.), or preservatives.

In some embodiments, pharmaceutical compositions as described herein include a therapeutically effective amount of an influenza VLP (comprising an engineered or re-engineered HA polypeptide as described herein) alone or in combination with a pharmaceutically acceptable carrier. Pharmaceutically acceptable carriers include, but are not limited to, saline, buffered saline, dextrose, water, glycerol, ethanol, and combinations thereof. In some embodiments, the carrier and composition are sterile, and the formulation suits the mode of administration. In some embodiments, a pharmaceutical composition contains minor amounts of wetting or emulsifying agents, or pH buffering agents. In some embodiments, a pharmaceutical composition is a liquid solution, suspension, emulsion, tablet, pill, capsule, sustained release formulation, or powder. In some embodiments, a pharmaceutical composition is formulated for intradermal injection, intranasal administration or intramuscular injection. Any of common pharmaceutical carriers, such as sterile saline solution or sesame oil, may be used. In some embodiments, a medium can also contain conventional pharmaceutical adjunct materials such as, for example, pharmaceutically acceptable salts to adjust the osmotic pressure, buffers, preservatives and the like. In some embodiments, other media that may be used with the compositions and methods provided herein are normal saline and sesame oil.

In some embodiments, the therapeutic agent present in a pharmaceutical composition in accordance with the invention will consist of one or more engineered or re-engineered HA polypeptide as described herein.

In some embodiments, a pharmaceutical composition will include a therapeutic agent that is encapsulated, trapped, or bound within a lipid vesicle, a bioavailable and/or biocompatible and/or biodegradable matrix, or other microparticle. In some embodiments, an immunogenic or pharmaceutical composition comprises nanoparticles displaying the engineered or re-engineered hemagglutinin polypeptides described herein. In some embodiments, the nanoparticles are ferritin nanoparticles (see, e.g., U.S. pre-grant publication 2014/0072958).

Pharmaceutical compositions of the present invention may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the purview of the present invention. In general, each agent will be administered at a dose and on a time schedule determined for that agent. Additionally, the invention encompasses the delivery of pharmaceutical compositions in accordance with the invention in combination with agents that may improve their bioavailability, reduce or modify their metabolism, inhibit their excretion, or modify their distribution within the body. Although the pharmaceutical compositions of the present invention can be used for treatment (e.g., vaccination) of any subject (e.g., any animal) in need thereof, they are most preferably used in the treatment of humans. In some embodiments, pharmaceutical compositions in accordance with the invention and/or engineered or re-engineered HA polypeptides as described herein are administered in combination with one or more of an anti-viral agent (e.g., Oseltamivir [TAMIFLU®], Zanamavir [RELEZA®], etc.) and/or a sialidase.

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc.

In some embodiments parenteral administration, such as subcutaneous, intravenous or intramuscular administration, is achieved by injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and. In some embodiments, administration of influenza VLPs as described herein is systemic or local.

In some embodiments, influenza VLPs, or compositions thereof, are administered in any suitable manner, such as with pharmaceutically acceptable carriers. As persons of skill are aware, pharmaceutically acceptable carriers are determined in part by the particular composition being administered, as well as by the particular method used to administer the composition. Accordingly, there is a wide variety of suitable formulations of pharmaceutical compositions as described herein.

In some embodiments, preparations for parenteral administration include sterile aqueous or nonaqueous solutions, suspensions, and emulsions. Exemplary non-aqueous solvents include propylene glycol, polyethylene glycol, vegetable oils such as olive oil, and injectable organic esters such as ethyl oleate. Exemplary aqueous carriers include water, alcoholic/aqueous solutions, emulsions or suspensions, including saline and buffered media. In some embodiments, parenteral vehicles include sodium chloride solution, Ringer's dextrose, dextrose and sodium chloride, lactated Ringer's, or fixed oils. In some embodiments, intravenous vehicles include fluid and nutrient replenishers, electrolyte replenishers (such as those based on Ringer's dextrose), and the like. In some embodiments, preservatives and/or other additives may also be present. Exemplary preservatives and/or other additives include antimicrobials, anti-oxidants, chelating agents, and inert gases and the like.

In some embodiments, compositions (influenza VLPs or otherwise comprising an HA polypeptide as described herein) are administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

At present the oral or nasal spray or aerosol route (e.g., by inhalation) is most commonly used to deliver therapeutic agents directly to the lungs and respiratory system. However, the invention encompasses the delivery of the pharmaceutical composition in accordance with the invention by any appropriate route taking into consideration likely advances in the sciences of drug delivery.

In some embodiments, preparations for inhaled or aerosol delivery comprise a plurality of particles. In some embodiments, such preparations have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, compositions in accordance with the invention are administered as drops to the nasal or buccal cavity. In some embodiments, a dose may comprise a plurality of drops (e.g., 1-100, 1-50, 1-20, 1-10, 1-5, etc.)

In some embodiments, compositions in accordance with the invention are administered using a device that delivers a metered dosage of composition (e.g., of engineered or re-engineered HA polypeptide).

Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference). Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

General considerations in the formulation and manufacture of pharmaceutical agents may be found, for example, in *Remington's Pharmaceutical Sciences,* $19^{th}$ ed., Mack Publishing Co., Easton, Pa., 1995; incorporated herein by reference.

Pharmaceutical compositions in accordance with the invention may be administered in any dose appropriate to achieve a desired outcome. In some embodiments, the desired outcome is induction of a lasting adaptive immune response against multiple influenza strains. In some embodiments, the desired outcome is reduction in intensity, severity, and/or frequency, and/or delay of onset of one or more symptoms of influenza infection.

In some embodiments, pharmaceutical compositions in accordance with the invention are administered in single or multiple doses. In some embodiments, pharmaceutical compositions in accordance with the invention are administered in multiple doses administered on different days (e.g., prime-boost vaccination strategies). In some embodiments, pharmaceutical compositions in accordance with the invention are administered according to a continuous dosing regimen, such that the subject does not undergo periods of less than therapeutic dosing interposed between periods of therapeutic dosing. In some embodiments, pharmaceutical compositions in accordance with the invention are administered according to an intermittent dosing regimen, such that the subject undergoes at least one period of less than therapeutic dosing interposed between two periods of therapeutic dosing.

In some embodiments, a dose administered to a subject should be sufficient to induce a beneficial therapeutic response in a subject over time, or to inhibit or prevent H1N1 influenza virus infection. The dose required will vary from subject to subject depending on the species, age, weight and general condition of the subject, the severity of the infection being treated, the particular composition being used and its mode of administration.

The present invention will be more fully understood by reference to the following Examples. All literature citations are incorporated by reference.

EXAMPLES

Example 1. Receptor Binding Site Grafting Improves Seasonal Immune Profile (Strength of Binding) of an Engineered HA Polypeptide The present Example describes the design and testing of engineered HA polypeptides that have increased breadth with respect to immunological profile by grafting a globular head region of the influenza HA protein, including the RBS, onto recipient HA stems. Structurally-defined regions of the globular head of an HA polypeptide exhibiting a seasonal immune profile were grafted onto the stem regions of HA molecules from pandemic-like strains (New Jersey/1976, South Carolina/1918, California/07/2009 and an novel, engineered pandemic HA). Three different regions of the HA globular head (defined as RBS 00, RBS 01 and RBS 02, FIG. 1) were tested for grafting.

For the purposes of the present example the three RBS-containing regions used for grafting were defined as G63-G277 (CA09 Numbering), V125-G277 (CA09 Numbering), and P135-P269 (CA09 Numbering). These RBS regions selected for grafting were chosen based on the criteria that they would cause minimal disruption to the overall protein fold upon detachment of the RBS from the rest of the HA molecule. More specifically, the RBS regions were selected in such a way that (i) the start and end positions are located in the loop regions bounding the RBS, which would help preserve local secondary structure, (ii) the compact globular structure of the resulting detached RBS is retained, and (iii) interface contacts are preserved upon integration of the donor RBS into the recipient molecule.

Figure 2:
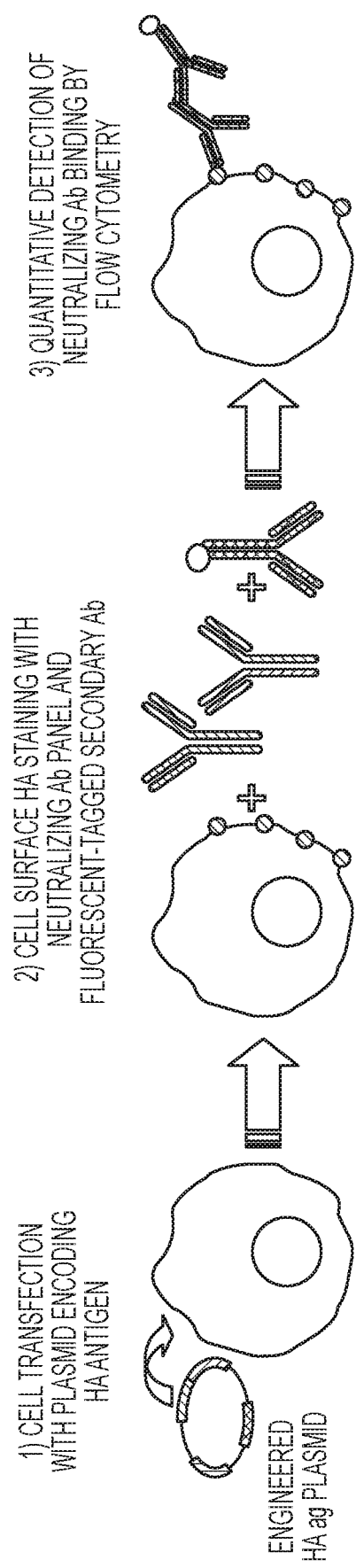
FIG. 2 shows a schematic of the flow cytometry assay used to demonstrate proper folding, expression, and antibody binding capabilities of influenza HA polypeptides.

Twelve individual combinations of donor RBS regions from an engineered HA with a predominantly seasonal immune profile paired with a recipient stem from a pandemic strain were synthesized (Table 3) and in vitro tested for cell surface expression and proper antigenic conformation using a flow cytometry based assay as described in International Application No. PCT/US2015/033205 which is incorporated herein by reference and depicted in FIG. 2. The assay provides a robust and rapid screening assay to identify designs that produce functional influenza hemagglutinin (HA) antigens for universal vaccines. It utilizes a panel of neutralizing antibodies to analyze expression and conformation of surface displayed engineered HA antigens. It not only identifies and validates engineered HA antigens that are properly expressed and structurally sound, but also predicts the breadth and/or specificity of immunogenicity of engineered HA antigens. Antibodies known to bind to conformational epitopes (e.g., epitopes close to the receptor-binding site) of the HA head and conserved conformational epitopes (e.g., A Helix) of the HA stem may be used in an antibody panel. As non-limiting examples, suitable anti-head neutralizing antibodies may include: CH65 (contemporary seasonal strains prior to the 2009 pandemic) (Whittle, J R R, et al. PNAS 2011), 5J8 (contemporary seasonal and historical strains) (Krause, J C, et al. J. Virology 2011), 4K8 (pandemic strains only) (Krause, J C, et al., J. Immunology 2011), AH4, and AH5. Suitable anti-stem neutralizing antibodies may include: C179 (group 1 HAs) (Okuno, Y et al., J. Virology 1993), AS2 (group 1 HAs), AS3 (group 1 and group 2 HAs), and AS4 (group 1 HAs).

TABLE 3

| SEQ ID NO. | Design ID | RBS Donor (engineered HA with a predominantly seasonal immune profile) | RBS Start | RBS End | RBS Recipient (pandemic strain) |
| --- | --- | --- | --- | --- | --- |
| SEQ ID NO: 7 | DO2a_tr1 | SMARt_DO2a | G63 | G277 | SMARt_DO1a* |
| SEQ ID NO: 8 | DO2a_tr2 | SMARt_DO2a | G63 | G277 | Cal2009 |
| SEQ ID NO: 9 | DO2a_tr3 | SMARt_DO2a | G63 | G277 | SC1918 |
| SEQ ID NO: 10 | DO2a_tr4 | SMARt_DO2a | G63 | G277 | NJ1976 |
| SEQ ID NO: 11 | DO2a_tr5 | SMARt_DO2a | V125 | G277 | SMARt_DO1a* |
| SEQ ID NO: 12 | DO2a_tr6 | SMARt_DO2a | V125 | G277 | Cal2009 |
| SEQ ID NO: 13 | DO2a_tr7 | SMARt_DO2a | V125 | G277 | SC1918 |
| SEQ ID NO: 14 | DO2a_tr8 | SMARt_DO2a | V125 | G277 | NJ1976 |
| SEQ ID NO: 15 | DO2a_tr9* | SMARt_DO2a | P135 | P269 | SMARt_DO1a* |
| SEQ ID NO: 16 | DO2a_tr10 | SMARt_DO2a | P135 | P269 | Cal2009 |
| SEQ ID NO: 17 | DO2a_tr11 | SMARt_DO2a | P135 | P269 | SC1918 |
| SEQ ID NO: 18 | DO2a_tr12 | SMARt_DO2a | P135 | P269 | NJ1976 |

*An engineered HA with predominantly pandemic immune profile

The assay consists of transfecting HEK293FT with a plasmid DNA using Lipofectamine. 24 hours post-transfection cells were labeled with LIVE/DEAD® Fixable Far Red Dead Cell Stain Kit to determine viability of the cells prior to surface staining. Subsequently cells re-suspended in staining buffer (0.1% BSA in PBS) were stained with 0.4 micrograms of indicated unlabeled neutralizing anti-hemagglutinin monoclonal antibody (e.g. e.g., CH65, 5J8, 4K8, AS3, C179, AS2, or AS4).

Stained cells were washed and re-suspended in 100 microliters of staining buffer containing 0.2 micrograms of Alexa Fluor® 488 Anti-Human or Anti-Mouse IgG secondary antibody (depending on primary antibody) and stained with secondary antibody for 20 min at 4° C. Finally, stained cells were re-suspended in fixation solution (1.75% formaldehyde in PBS) and stored for <1 week at 4° C.

Flow Cytometry Analysis

Fixed cells were washed and re-suspended in 200 microliters of PBS, and then transferred to deep-well 96-well plate for sample acquisition using a BD High-Throughput Sampler. Sample analysis was performed using a BD FACS Calibur flow cytometer equipped with a 488 nm laser (for Alexa Fluor® 488 excitation) and a 635 nm laser (for LIVE/DEAD far red dye excitation). A mock-transfected cell sample stained with Alexa Fluor® 488 secondary antibody but no primary antibody was used to determine optimal acquisition settings. In particular forward-scatter (FSC) amplification gain, side-scatter (SSC) voltage and FSC threshold were adjusted to display the HEK293FT cell population on scale and to exclude unwanted debris. Cell population was gated in the FSC vs SSC plot to further exclude debris. Fluorescence detector settings were also adjusted using mock-transfected cells stained only with secondary antibody. In particular FL1 detector (for detection of Alexa Fluor® 488 fluorescence) and FL4 detector (for detection of LIVE/DEAD far red dye fluorescence) voltages were adjusted to place fluorescence emission of the gated cell population in first log decade. Compensation adjustments were not required for this fluorophore combination as there is no spectral overlap between Alexa Fluor® 488 and LIVE/DEAD far red dye. All samples were acquired using same acquisition settings as the mock control. At least 10,000 cells within FSC vs SSC gate were counted for each sample and data was saved as FCS data files.

Data analysis was performed using FlowJo software. FCS data file corresponding to mock-transfected cells stained only with secondary antibody was used to create analysis gates. In particular, a gate including intact cell population was first drawn in the FSC vs SSC plot. This gated cell subset was then analyzed in separate plot displaying FL4 fluorescence intensity (LIVE/DEAD far red dye fluorescence) vs FSC. A new gate encompassing the cell population with low FL4 fluorescence intensity was created. This new cell subset corresponding to intact live cells was further analyzed in separate plot displaying FL1 fluorescence intensity (Alexa Fluor® 488 fluorescence) vs FSC. A new gate encompassing cells with positive FL1 fluorescence as defined by fluorescence values that leave 95% of the mock-transfected cells in the negative FL1 fraction was generated. All FCS files were analyzed using the same analysis gates. Median fluorescence intensity (MFI) of positive FL1 cell subset for each cell sample and staining was exported to excel file and used to calculate antibody binding ratio.

MFI of positive FL1 cell subset for each cell sample and staining was first corrected by subtracting background fluorescence corresponding to same cell sample stained with secondary antibody only. Specificity of the staining with each of the neutralizing anti-hemagglutinin monoclonal antibodies was confirmed by examining the background corrected MFI of mock-transfected cells (negative control) and the background corrected MFI of cells transfected with wild-type HA plasmid DNA (positive control). If MFI for controls fell within expected range of values, then antibody binding ratio for each engineered HA plasmid and neutralizing anti-HA monoclonal antibody was determined as follows:

$$\text{Antibody binding ratio } (ABR) = \frac{MFI\,(HA\ x,\ \text{primary } ab\ y) - MFI\,(HA\ x,\ \text{secondary } ab\ \text{only})}{MFI\,(\text{wild-type } HA,\ \text{primary } ab\ y) - MFI\,(\text{wild-type } HA,\ \text{secondary } ab\ \text{only})}$$

Figure 3:
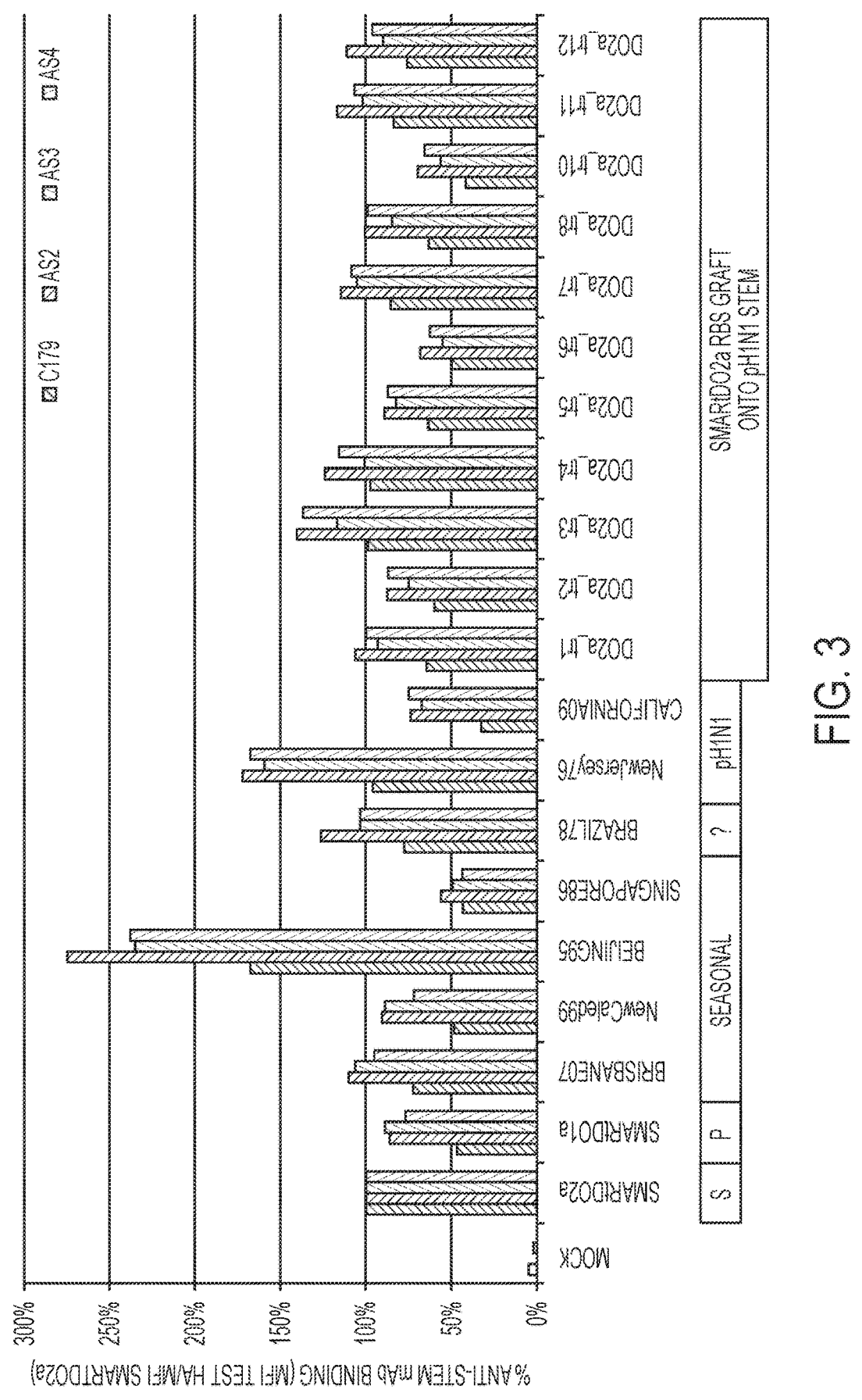
Figure 4:
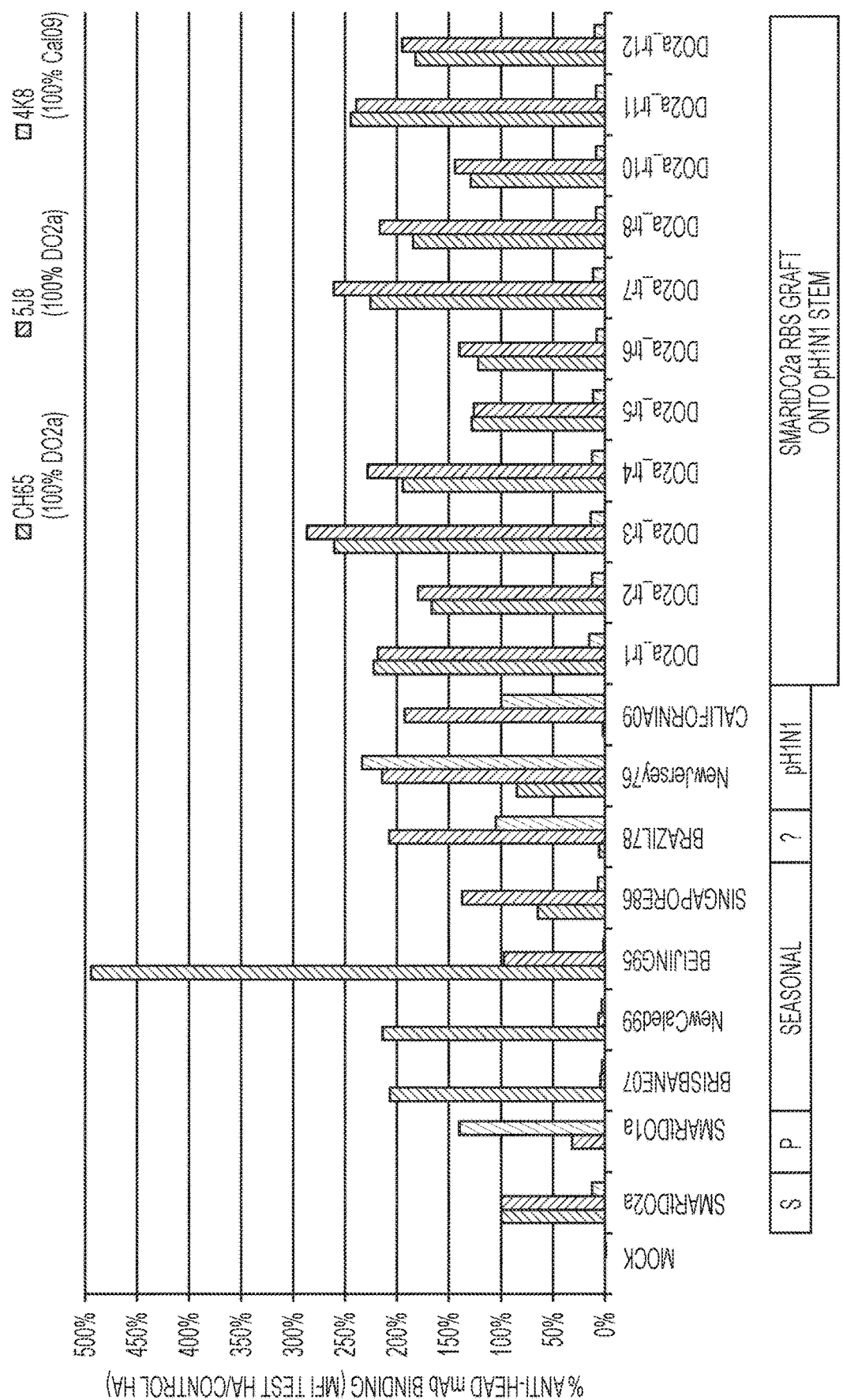
FIG. 4 shows flow cytometry assay results demonstrating an improved seasonal immune profile (as demonstrated by increased mAb binding) of recombinant HA polypeptides generated by grafting globular head regions of the influenza RBS onto recipient HA stems.

Each of the recombinant HA polypeptides was surface expressed (i.e., capable of intercellular processing similar to wild-type influenza antigens produced in an infected cell) and retained stem folding (comparable to or better than wild-type strain controls) as determined by binding of a panel of anti-stem antibodies in the flow cytometry assay (FIG. 3). This experiment also demonstrates that, in some cases, modifications in the head region induced a modest increase in binding to anti-stem mAbs. Thus, substitutions at one place may exert long-range allosteric effects on a distant location. Likewise, the new recombinant HA polypeptides generated by seasonal RBS-region stem grafting onto pandemic stems surprisingly demonstrated improved seasonal immune profiles. These re-engineered recombinant HA polypeptides demonstrated increased binding of seasonal strain neutralizing antibodies relative to the initial engineered HA parent molecule (SMARt_DO2a). (FIG. 4). In these assays, "increased mAb binding" is a measure of the mean fluorescent intensity of the antibody bound to a re-engineered HA relative to a control: an unmodified parent engineered HA (SMARt_DO2a) for CH65 and 5J8 antibodies, and a wild-type pandemic strain, A/California/7/2009 H1N1, for 4K8. "Increased mAb binding", therefore, is an approximate measure of antibody affinity. In some cases, the seasonal immune profile (as measured by mAb binding) was improved by 2-3 fold over the parent seasonal engineered HA molecule. (FIG. 5; compare seasonal head antibody binding (e.g., CH65 and 5J8) of column 2 to the re-engineered constructs in columns 5 and 6).

Since the RBS part of the grafted antigens is identical to that of the engineered HA with a predominantly seasonal immune profile, expansion of breadth relative to the recipient pandemic strain comes from the non-RBS part of the re-engineered HA. Increases in breadth are more evident in vivo experiments rather than in HAI assays or binding assays to antibodies that target the RBS.

Example 2. Disruption of N-Linked Glycosylation Sites and/or Loop Insertion Increases Immunological Breadth of an Engineered HA Polypeptide The present Example describes a second strategy for increasing immunological breadth of engineered HA polypeptides by modifying residues associated with predicted N-linked glycosylation sites and introducing a lysine into a loop bounding the RBS. Seasonal influenza strains contain additional putative N-linked glycosylation sites compared to pandemic strains. Glycosylation has the potential to block antigenic sites within HA altering the immune response. Such glycosylation sites are identified by the sequence motif NxS/Ty, wherein x and y are not proline (P). The asparagine in this N-Linked glycosylation pattern can be found in HA polypeptides near or at residues corresponding to 142 and 177 (CA09 Numbering) in the receptor binding site (FIG. 6; left panel demonstrating the relevant sequences in a wild-type pandemic H1N1 strain and the corresponding glycosylated sequences in an exemplary engineered HA polypeptide, "DO2").

A lysine insertion into a loop within or near the HA RBS region predicted N-linked glycosylation sites is a feature of pandemic influenza A viruses. Insertion into a loop (e.g., insertion of a lysine or arginine residue) near the N-linked glycosylation sites provides a pandemic strain feature into an engineered HA polypeptide (FIG. 6; center panel).

Figures 5, 6:
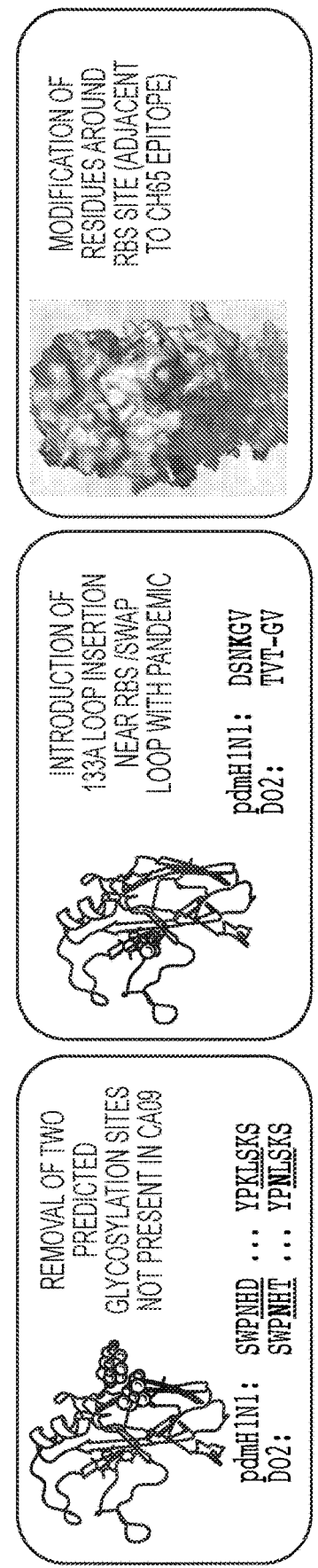
FIG. 5 shows a numerical representation of the increased immunological breadth of recombinant HA polypeptides generated by grafting globular head regions of the influenza RBS onto recipient HA stems.
FIG. 6 shows a graphical representation of the putative N-Linked glycosylation sites, lysine loop insertion sites and modification of residues around the RBS site.

Modification of residues around the RBS site adjacent to the CH65 epitope further incorporates features of pandemic influenza A viruses (FIG. 6; right panel).

To demonstrate the increased immunological breadth imparted to an engineered HA polypeptide by modifications to the predicted N-Linked glycosylation site and/or lysine loop insertion, specific amino acid residues in an exemplary engineered HA polypeptide ("SMARt_DO2a") were modified to reflect those observed in pandemic-like HA polypeptides. Table 4 demonstrates the potential amino acid substitutions that can be made at these sites as determined from observed residues at each position in circulating influenza A viruses.

TABLE 4

| N-linked site (CA09 numbering) | Engineered HA residue index | Exemplary Residues | AA Substitutions to disrupt NxS/T pattern |
| --- | --- | --- | --- |
| 142 | 142 | N | D, K, S |
|  | 143 | H | Y |
|  | 144 | T | E, D, N |
|  | 145 | V | I, L, P, S, T |
|  | 146 | T | D, L, N, S |
|  | 147 (loop insertion) | — (gap) | K, R |
| 177 | 177 | N | K, R, T |
|  | 178 | L | I |
|  | 179 | S | I, K, N, R |

Figure 7:
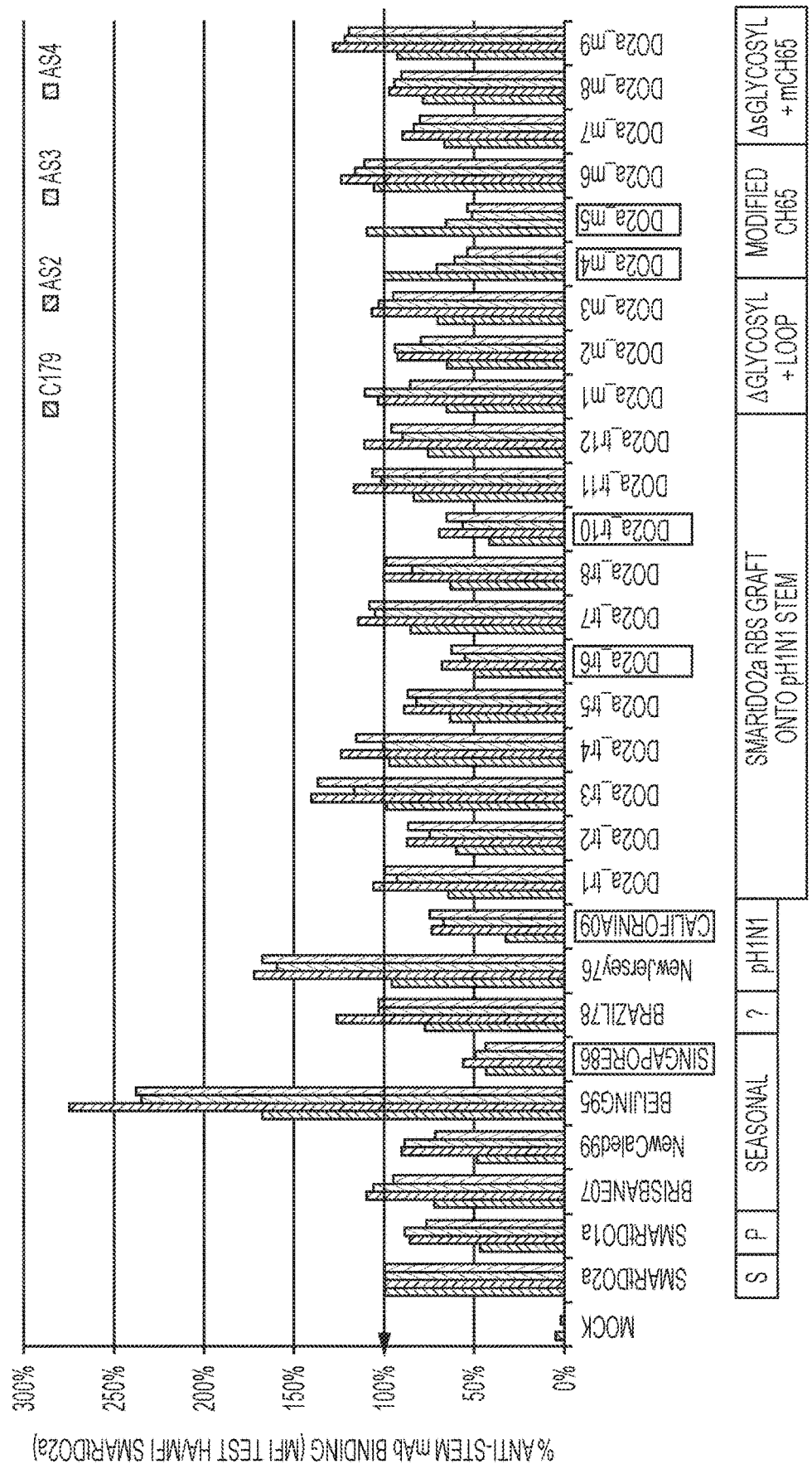
FIG. 7 shows flow cytometry assay results demonstrating the proper folding and expression of recombinant HA polypeptides generated by modifications to putative N-linked glycosylation sites, lysine loop insertions, or amino acid residues in the globular head region.
Figure 8:
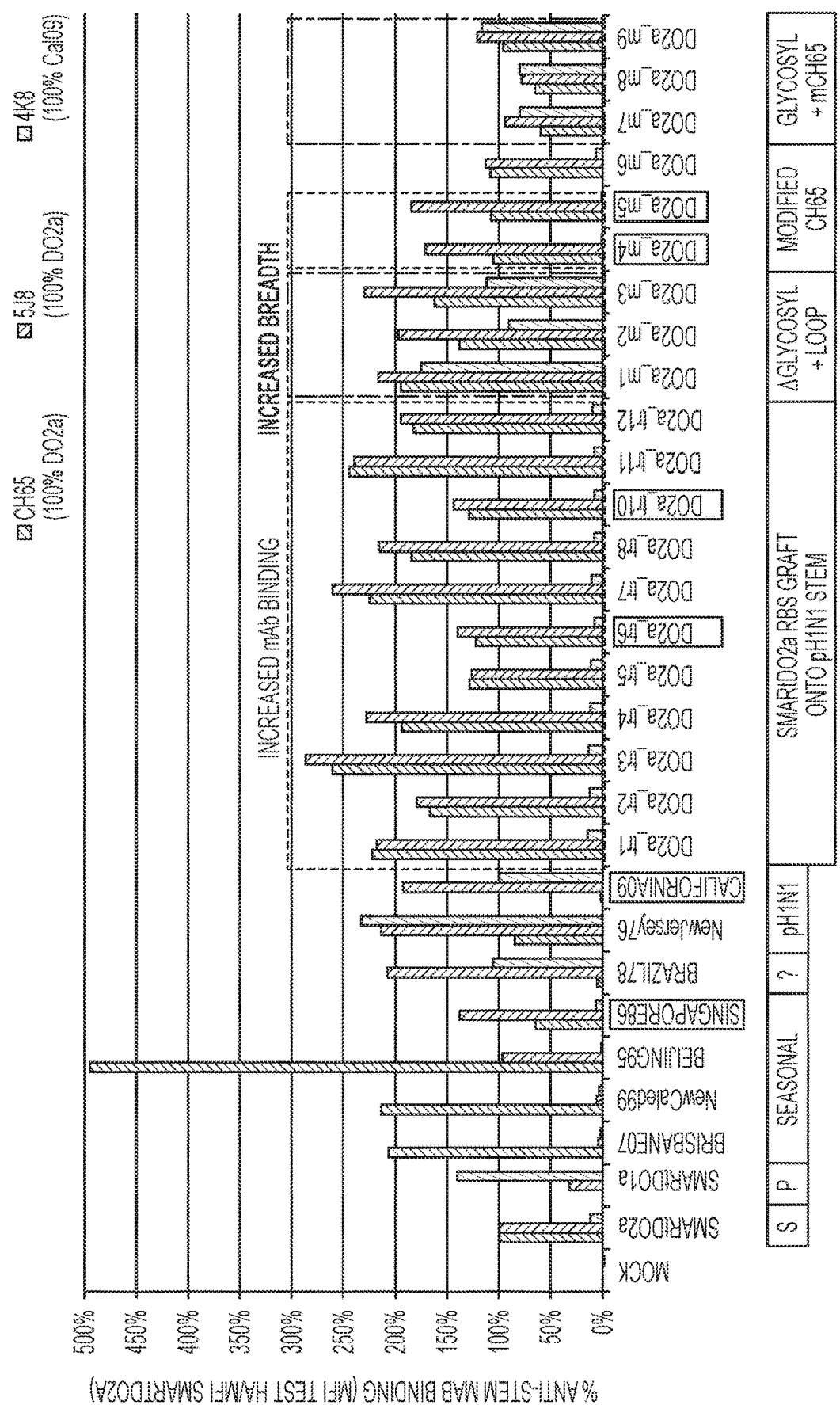
FIG. 8 shows flow cytometry assay results demonstrating the increased immunological breadth of recombinant HA polypeptides generated by modifications to putative N-linked glycosylation sites, lysine loop insertions or amino acid residues in the globular head region.

To demonstrate the effect of disruption of N-linked glycosylation sites on the immunological breadth of HA polypeptides, engineered HA molecules were produced with disruption of two N-Linked glycosylation motif sites. Additionally, two engineered HA polypeptides were generated in which the N-Linked glycosylation motif sites were disrupted and a lysine was inserted into a loop bounding the RBS (Table 5). Disruption of the glycosylation motif alone as well as in combination with a lysine loop insertion produced recombinant HA polypeptides that were surface expressed and retained stem folding as determined by the flow cytometry assay (FIG. 7). Once again, it was observed that modifications in the head region induced a modest increase in binding to anti-stem mAbs; demonstrating that substitutions at one place may exert long-range allosteric effects on a distant location. These modifications also contributed to an increased immunological breadth based on the recognition by a panel of antibodies (FIG. 8). More specifically, several of the re-engineered antigens demonstrated both improved seasonal properties (increased mAb binding of anti-seasonal head antibodies CH65 and 5J8) and an increased breadth demonstrated by a 50-150% increase in binding of the anti-pandemic head antibody 4K8 (see constructs DO2a_m1 to m3 in FIG. 8).

TABLE 5

| construct | Residue indices (CA09 numbering) | Original sequence (Engineered HA, e.g., DO2a) | Modified sequences |
| --- | --- | --- | --- |
| 1 | 144, 145, 146 | TVT | DSN |
|  | 177 | N | K |
| 2 | 144, 145, 146 | TVT | DSN |
|  | 177 | N | K |
|  | 147 | — (gap) | K |
| 3 | 144, 145, 146 | TVT | ETT |
|  | 177 | N | K |
|  | 147 | — (gap) | K |

Example 3. Modifications to Amino Acid Residues in the Region of the RBS and N-Linked Glycosylation Increase Immunological Breadth of an Engineered HA Polypeptide The present Example describes modifications to an engineered HA polypeptide in the region of or adjacent to the RBS of HA by introduction of amino acid substitutions. Amino acid substitutions are position specific and derived from residues identified from analysis of the head region of HA in circulating influenza A viruses. Table 6 describes a pool of residues in specific positions encompassing residues 60 to 291 (based on CA/09 Numbering) from which specific amino acid substitutions were selected for targeted modification of the globular head of HA. A smaller pool of residues in specific positions encompassing residues 137 to 262 (based on CA/09 Numbering) from which specific amino acid substitutions was selected for targeted modification of the globular head of HA as described in Table 7. Table 8 describes the pool of residues used for targeted modification of the immunological profile of HA for residues within 10 Angstroms of the RBS. These residues are indicated by shading in FIG. 9.

TABLE 6

| Engineered HA residue index | AA Substitutions |
| --- | --- |
| 60 | K, L, N, Q, S, R |
| 61 | I, L |
| 62 | G, K, M, N, R |
| 63 | E, G |
| 64 | A, E, I, K, M, T, V |
| 65 | A, I, P, S, T, V |
| 68 | H, N, Q |
| 70 | D, G |
| 71 | E, K, N, S, R |
| 73 | D, N, S, T |
| 74 | I, V |
| 77 | R, W |
| 78 | I, L, V |
| 83 | E, D, G, K |
| 85 | E, D, G |
| 86 | F, L, P, S, T |
| 87 | F, I, L, P |
| 88 | F, I, L, P, S, T, V, Y |
| 89 | A, I, K, P, S, T |
| 90 | A, E, I, K, N, S, R, T, V |
| 91 | E, D, G, I, K, N, S, R |
| 92 | S, T |
| 94 | P, S |
| 97 | A, I, V |
| 99 | A, I, K, N, S, R, T |
| 100 | F, P, S, T, Y |
| 101 | D, G, I, K, N, S, T, Y |
| 102 | A, P, S, T |
| 103 | E, D, G, K, N, R, Y |
| 104 | D, K, N |

TABLE 6-continued

| Engineered HA residue index | AA Substitutions |
|---|---|
| 105 | G, W |
| 106 | A, I, M, T |
| 111 | E, D, G, H, N, V, Y |
| 113 | A, I, N, S, T, V |
| 114 | D, N |
| 116 | E, G, V |
| 119 | K, R, T |
| 120 | E, K |
| 121 | H, L, Q, R |
| 123 | G, N, S |
| 124 | S, T |
| 125 | A, I, M, L, V |
| 126 | L, S, T |
| 127 | L, S |
| 128 | F, L |
| 129 | E, K |
| 130 | K, R |
| 131 | F, Y |
| 132 | E, K |
| 133 | I, M, L, V |
| 134 | F, V |
| 135 | H, P, S |
| 136 | E, K, M, N, Q, R |
| 137 | A, E, D, G, I, S, T, V |
| 138 | G, I, N, S, R, T |
| 139 | A, S |
| 141 | L, P, S |
| 142 | D, K, N, S, Y |
| 143 | H, Y |
| 144 | E, D, N, S, T |
| 145 | A, I, L, P, S, T, V |
| 146 | D, L, N, S, T |
| 147 | I, K, N, R, — |
| 149 | A, E, I, T, V |
| 150 | S, T |
| 151 | A, I, M, S, T, V |
| 152 | A, S |
| 154 | A, H, L, P, S, T |
| 155 | H, N, Q, S, R, Y |
| 156 | A, E, D, G, K, N, S, R, T, V |
| 157 | E, G, K, R |
| 158 | A, E, K, M, S, T, V |
| 159 | K, L, N, S, R |
| 160 | G, N, S |
| 163 | E, K, N, Q, R |
| 164 | N, S |
| 166 | I, M, L, V |
| 168 | I, L |
| 169 | A, I, T, V |
| 170 | E, G, K, Q, R, V |
| 171 | A, E, K, N, R, T |
| 172 | E, D, G, K, N |
| 173 | D, G, I, K, N, S, T |
| 174 | L, S, T |
| 176 | P, S |
| 177 | E, K, M, N, S, R, T |
| 178 | F, I, L, V |
| 179 | G, I, K, N, S, R, T |
| 180 | E, I, K, M, N, Q, S, R, T |
| 181 | F, P, S, T |
| 182 | F, Y |
| 183 | A, E, F, I, K, L, S, T, V |
| 185 | D, K, N, S |
| 186 | K, Q, R |
| 187 | E, D, G, K, R |
| 188 | E, K, N, R |
| 189 | E, D, G, K, V |
| 190 | I, V |
| 192 | I, M, L, V |
| 193 | I, L |
| 195 | A, G |
| 196 | I, V |
| 198 | H, N |
| 199 | Q, P, S |
| 200 | A, P, S |
| 201 | A, D, N, S, T |
| 202 | A, D, I, M, N, P, S, T, Y |

TABLE 6-continued

| Engineered HA residue index | AA Substitutions |
|---|---|
| 203 | A, E, D, G, I, K, N, S, R, T, V |
| 204 | A, B, E, D, G, N, V, Y |
| 205 | Q, R |
| 206 | K, M, L, N, Q, S, R |
| 207 | A, G, I, N, S, R, T |
| 208 | I, J, L |
| 210 | H, K, N, Q, S, R |
| 211 | K, N, S, T |
| 212 | A, E, D, G, I, N, T, V |
| 213 | E, D, H, N, Y |
| 214 | A, S, T |
| 215 | H, Y |
| 216 | A, I, V |
| 217 | F, L, S |
| 218 | I, V |
| 219 | E, G, M, S, W, V |
| 220 | S, T |
| 221 | P, S, T |
| 222 | H, K, N, R, T |
| 224 | N, S, Y |
| 225 | G, K, Q, R |
| 226 | E, I, K, M, N, R |
| 227 | F, L, S |
| 228 | E, I, K, N, R, T |
| 231 | I, V |
| 232 | A, E, G, T, V |
| 233 | A, E, I, K, M, R, T, V |
| 234 | R |
| 235 | L, P |
| 236 | K, R |
| 237 | I, M, V |
| 238 | K, R |
| 239 | E, D, G, K, N |
| 240 | Q, R |
| 241 | A, E, G, H, K, P, S, T |
| 242 | A, G, R |
| 244 | I, M |
| 245 | D, K, N, S |
| 247 | H, Y |
| 249 | A, I, T |
| 250 | I, M, L, V |
| 251 | I, L, V |
| 252 | A, E, D, G, K, N, V |
| 253 | Q, P, S |
| 254 | E, G, R |
| 255 | E, D, G, N |
| 256 | K, R, T |
| 257 | I, V |
| 258 | I, M, T |
| 259 | F, L |
| 261 | A, T |
| 262 | N, S, T |
| 266 | A, I, M, L, V |
| 267 | A, I, V |
| 269 | I, K, M, S, R, W |
| 270 | F, H, Y |
| 273 | A, E, T, V |
| 274 | I, M, L, V |
| 275 | E, D, G, K, N, S, R, V |
| 276 | G, K, R |
| 277 | D, G, K, N, S, T |
| 278 | A, D, F, L, P, S, T, V, Y |
| 279 | E, D, G, N, S, R |
| 280 | A, F, P, S, Y |
| 281 | D, G, S |
| 282 | F, I, V |
| 283 | F, I, M, V |
| 284 | I, K, M, L, N, S, R, T, V |
| 285 | S, T |
| 286 | E, D, G, N |
| 287 | A, I, K, S, T, V |
| 288 | H, L, Q, P, S, T |
| 289 | A, F, I, M, L, V |
| 290 | D, G, H, N, Q, R, Y |
| 291 | E, D, G, K, N |

TABLE 7

| Engineered HA residue index | AA Substitutions |
| --- | --- |
| 137 | A, E, D, G, I, S, T, V |
| 138 | G, I, N, S, R, T |
| 139 | A, S |
| 141 | L, P, S |
| 142 | D, K, N, S, Y |
| 143 | H, Y |
| 144 | E, D, N, S, T |
| 145 | A, I, L, P, S, T, V |
| 146 | D, L, N, S, T |
| 147 | I, K, N, R, — |
| 149 | A, E, I, T, V |
| 150 | S, T |
| 151 | A, I, M, S, T, V |
| 152 | A, S |
| 154 | A, H, L, P, S, T |
| 155 | H, N, Q, S, R, Y |
| 156 | A, E, D, G, K, N, S, R, T, V |
| 157 | E, G, K, R |
| 158 | A, E, K, M, S, T, V |
| 159 | K, L, N, S, R |
| 160 | G, N, S |
| 163 | E, K, N, Q, R |
| 164 | N, S |
| 166 | I, M, L, V |
| 168 | I, L |
| 169 | A, I, T, V |
| 170 | E, G, K, Q, R, V |
| 171 | A, E, K, N, R, T |
| 172 | E, D, G, K, N |
| 173 | D, G, I, K, N, S, T |
| 174 | L, S, T |
| 176 | P, S |
| 177 | E, K, M, N, S, R, T |
| 178 | F, I, L, V |
| 179 | G, I, K, N, S, R, T |
| 180 | E, I, K, M, N, Q, S, R, T |
| 181 | F, P, S, T |
| 182 | F, Y |
| 183 | A, E, F, I, K,L, S, T, V |
| 185 | D, K, N, S |
| 186 | K, Q, R |
| 187 | E, D, G, K, R |
| 188 | E, K, N, R |
| 189 | E, D, G, K, V |
| 190 | I, V |
| 192 | I, M, L, V |
| 193 | I, L |
| 195 | A, G |
| 196 | I, V |
| 198 | H, N |
| 199 | Q, P, S |
| 200 | A, P, S |
| 201 | A, D, N, S, T |
| 202 | A, D, I, M, N,P, S, T, Y |
| 203 | A, E, D, G, I, K, N, S, R, T, V |
| 204 | A, B, E, D, G, N, V, Y |
| 205 | Q, R |
| 206 | K, M, L, N, Q, S, R |
| 207 | A, G, I, N, S, R, T |
| 208 | I, J, L |
| 210 | H, K, N, Q, S,R |
| 211 | K, N, S, T |
| 212 | A, E, D, G, I, N, T, V |
| 213 | E, D, H, N, Y |
| 214 | A, S, T |
| 215 | H, Y |
| 216 | A, I, V |
| 217 | F, L, S |
| 218 | I, V |
| 219 | E, G, M, S, W, V |
| 220 | S, T |
| 221 | P, S, T |
| 222 | H, K, N, R, T |
| 224 | N, S, Y |
| 225 | G, K, Q, R |
| 226 | E, I, K, M, N,R |
| 227 | F, L, S |

TABLE 7-continued

| Engineered HA residue index | AA Substitutions |
| --- | --- |
| 228 | E, I, K, N, R,T |
| 231 | I, V |
| 232 | A, E, G, T, V |
| 233 | A, E, I, K, M, R, T, V |
| 234 | R |
| 235 | L, P |
| 236 | K, R |
| 237 | I, M, V |
| 238 | K, R |
| 239 | E, D, G, K, N |
| 240 | Q, R |
| 241 | A, E, G, H, K, P, S, T |
| 242 | A, G, R |
| 244 | I, M |
| 245 | D, K, N, S |
| 247 | H, Y |
| 249 | A, I, T |
| 250 | I, M, L, V |
| 251 | I, L, V |
| 252 | A, E, D, G, K, N, V |
| 253 | Q, P, S |
| 254 | E, G, R |
| 255 | E, D, G, N |
| 256 | K, R, T |
| 257 | I, V |
| 258 | I, M, T |
| 259 | F, L |
| 261 | A, T |
| 262 | N, S, T |

TABLE 8

| Engineered HA residue index | AA Substitutions |
| --- | --- |
| 90 | A, E, I, K, N, S, R, T, V |
| 91 | E, D, G, I, K, N, S, R |
| 92 | S, T |
| 125 | A, I, M, L, V |
| 126 | L, S, T |
| 127 | L, S |
| 128 | F, L |
| 129 | E, K |
| 130 | K, R |
| 131 | F, Y |
| 132 | E, K |
| 133 | I, M, L, V |
| 134 | F, V |
| 135 | H, P, S |
| 136 | E, K, M, N, Q, R |
| 137 | A, E, D, G, I, S, T, V |
| 138 | G, I, N, S, R, T |
| 139 | A, S |
| 141 | L, P, S |
| 142 | D, K, N, S, Y |
| 143 | H, Y |
| 144 | E, D, N, S, T |
| 145 | A, I, L, P, S, T, V |
| 146 | D, L, N, S, T |
| 147 | I, K, N, R, — |
| 149 | A, E, I, T, V |
| 150 | S, T |
| 151 | A, I, M, S, T, V |
| 152 | A, S |
| 154 | A, H, L, P, S, T |
| 155 | H, N, Q, S, R, Y |
| 156 | A, E, D, G, K, N, S, R, T, V |
| 157 | E, G, K, R |
| 158 | A, E, K, M, S, T, V |
| 159 | K, L, N, S, R |
| 177 | E, K, M, N, S, R, T |
| 178 | F, I, L, V |
| 179 | G, I, K, N, S, R, T |
| 180 | E, I, K, M, N, Q, S, R, T |

TABLE 8-continued

| Engineered HA residue index | AA Substitutions |
|---|---|
| 181 | F, P, S, T |
| 182 | F, Y |
| 183 | A, E, F, I, K, L, S, T, V |
| 185 | D, K, N, S |
| 186 | K, Q, R |
| 187 | E, D, G, K, R |
| 188 | E, K, N, R |
| 189 | E, D, G, K, V |
| 190 | I, V |
| 192 | I, M, L, V |
| 193 | I, L |
| 195 | A, G |
| 210 | H, K, N, Q, S, R |
| 211 | K, N, S, T |
| 212 | A, E, D, G, I,N, T, V |
| 213 | E, D, H, N, Y |
| 214 | A, S, T |
| 215 | H, Y |
| 216 | A, I, V |
| 217 | F, L, S |
| 218 | I, V |
| 219 | E, G, M, S,W, V |
| 220 | S, T |
| 221 | P, S, T |
| 222 | H, K, N, R, T |
| 224 | N, S, Y | glycosylation profile modifications (e.g., ablation of glycosylation sites) described above. These modifications resulted in a recombinant HA polypeptide that was properly folded and surface expressed (FIG. 7). Once again, it was observed that modifications in the head region induced a modest increase in binding to anti-stem mAbs; demonstrating that substitutions at one place may exert long-range allosteric effects on a distant location. The reengineered recombinant HAs were recognized by both pandemic and seasonal specific antibodies (FIG. 8). Interestingly, the RBS modifications alone improved the seasonal immune profile (FIG. 8, DO2a_m4-m5; "Modified CH65"), but had little effect on the pandemic profile. However, combining the RBS region modifications with the glycosylation modifications significantly improved both the seasonal and pandemic immune profiles. (FIG. 8, DO2a_m7-m9; "Δglycosyl+mCH65"). This data indicated that the modifications improved the seasonal immune profile ("Increased mAb binding") and imparted a more pandemic immune profile ("Increased breadth"), thereby making an overall more balanced immune profile capable of addressing antigenic drift and antigenic shift in an exemplary engineered HA polypeptide (e.g., SMARt_DO2a).

TABLE 9

| construct | Modification | Residue indices (CA09 numbering) | Original sequence of engineered HA (SMARt_DO2a) | Modified sequences |
|---|---|---|---|---|
| 1 | E137T (charge change) | 137 | E | T |
|   | antigenic site Ca | 154-159 | SHNGKS | PHAGAK |
|   | antigenic site Sa | 210-214 | HTEN | QNAD |
|   | N262T | 262 | N | T |
| 2 | antigenic site Ca | 154-159 | SHNGKS | PHAGAK |
| 3 | antigenic site Sa | 210-214 | HTEN | QNAD |
| 4 | E137T (charge change) | 137 | E | T |
|   | Ngly142 | 144-145 | TV | NT |
|   | antigenic site Ca | 154-159 | SHNGKS | PHAGAK |
|   | Ngly177 | 177 | N | T |
|   | antigenic site Sa | 210-214 | HTEN | QNAD |
|   | N262T | 262 | N | T |
| 5 | Ngly142 | 144-145 | TV | NT |
|   | antigenic site Ca | 154-159 | SHNGKS | PHAGAK |
|   | Ngly177 | 177 | N | T |
| 6 | Ngly142 | 144-145 | TV | NT |
|   | Ngly177 | 177 | N | T |
|   | antigenic site Sa | 210-214 | HTEN | QNAD |

TABLE 8-continued

| Engineered HA residue index | AA Substitutions |
|---|---|
| 225 | G, K, Q, R |
| 226 | E, I, K, M, N, R |
| 245 | D, K, N, S |
| 247 | H, Y |
| 249 | A, I, T |

Modifications of residues in an engineered HA polypeptide with a seasonal immune profile that were tested as proof of principle are described in Table 9. These modifications included combining the RBS region modifications with the Example 4. In Vivo Efficacy of Engineered HA Polypeptides This Example illustrates that engineered HA polypeptides modified in accordance with methods described herein elicit immune responses in the form of broad antibody responses against several influenza strains.

Preparation of Virus-Like Particles (VLPs) Containing Engineered Mosaic Hemagglutinins (HAs)

Influenza VLPs are prepared by three-plasmid transient transfection of HEK293T cells in serum-free Freestyle293 medium. Plasmids encoding engineered HA polypeptide sequence as well as those for NA, and HIVgag are mixed at 1:1:1 ratio and used to transiently transfect the HEK293T cells. Culture supernatants are harvested 120 hours post-transfection and VLPs in the supernatant are pelleted by ultracentrifugation over a 20% sucrose cushion and resuspended in PBS.

Immunization of Mice with VLPs Expressing Engineered HAs

To assess immunogenicity of engineered mosaic HA designs, groups of 6-8 week old female BALB/c mice are immunized with 5 µg of influenza VLPs or vehicle alone (PBS). All immunizations are formulated as emulsions with an oil-in-water adjuvant, and are delivered subcutaneously in a total volume of 100 µl. Each group receives an identical booster dose 21 days after the initial immunization. Pre-immune and post-immune serum is collected from each animal on days 0 and 35, respectively. Serum pools used for analysis are prepared by mixing equal volumes of serum from each animal within a group.

Hemagglutination Inhibition (HAI) Assay

Replicate serial dilutions of pooled serum from each group are mixed with 4 hemagglutination units of the indicated virus and incubated at room temperature for 30 minutes in a round bottom plate. Each serum/virus mixture is then mixed with an equal volume of 0.5% turkey erythrocytes in saline. The plates are scored when control wells lacking serum demonstrate complete hemagglutination (~30 min). The HAI titer is defined as the maximum serum dilution resulting in complete inhibition of hemagglutination in 50% of the wells tested.

Microneutralization (MN) Assay

Replicate serial dilutions of pooled serum from each group are mixed with 100 50% tissue culture infectious doses (TCID50) of a virus and incubated at 37° C. for one hour. Each serum/virus mixture is then added to confluent monolayers of madin darby canine kidney (MDCK) cells and incubated at 37° C. for 24 hrs. The monolayers are then fixed and infected wells are identified based on ELISA detection of influenza nucleoprotein. The MN titer is defined as the highest dilution of serum resulting in complete neutralization of virus infection in 50% of the wells tested.

Immunogenicity Assays

HAI assays are conducted using modified recombinant HA polypeptides with RBS regions grafted on to recipient stem regions, modifications to remove or engineer putative N-linked glycosylation sites, and/or targeted modifications to residues in the RBS region. These modified recombinant HA polypeptides elicit a broader immune response.

Example 5. Exemplary Modified Recombinant HA Polypeptides

This example illustrates examples of modified recombinant HA polypeptides generated using various methods described herein.

DO2aRBStrunc00_resG63_G278_graftedontDo1a
(SEQ ID NO: 7)
MKAKLLVLLCTFTATYADTICIGYHANNSTDTVDTVLEKNVTVTHSVNLLE

DSHNGKLCKLKGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSDTPVHDCNTTCQTPQGAINSSL

PFQNVHPVTIGECPKYVRSAKLRMATGLRNIPSIQSRGLFGAIAGFIEGGW

TGMVDGWYGYHHQNEQGSGYAADLKSTQNAIDGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNNTCMESVKNGTYDYPKYSEESK

LNREKIDGVKLESMGVYQILAIYSTVASSLVLLVSLGAISFWMCSNGSLQC

RICI

DO2aRBStrunc00_resG63_G277_graftedontoCal2009
(SEQ ID NO: 8)
MKAKLLVLLCTFTATYADTLCIGYHANNSTDTVDTVLEKNVTVTHSVNLLE

DKHNGKLCKLRGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGAGSGIIISDTPVHDCNTTCQTPKGAINTSL

PFQNIHPITIGKCPKYVKSTKLRLATGLRNIPSIQSRGLFGAIAGFIEGGW

TGMVDGWYGYHHQNEQGSGYAADLKSTQNAIDEITNKVNSVIEKMNTQFTA

VGKEFNHLEKRIENLNKKVDDGFLDIWTYNAELLVLLENERTLDYHDSNVK

NLYEKVRSQLKNNAKEIGNGCFEFYHKCDNTCMESVKNGTYDYPKYSEEAK

LNREEIDGVKLESTRIYQILAIYSTVASSLVLVVSLGAISFWMCSNGSLQC

RICI

DO2aRBStrunc00_resG63_G277_graftedontoSC1918
(SEQ ID NO: 9)
MKAKLLVLLCTFTATYADTICIGYHANNSTDTVDTVLEKNVTVTHSVNLLE

DSHNGKLCKLKGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGSGSGIITSDAPVHDCNTKCQTPHGAINSSL

PFQNIHPVTIGECPKYVRSTKLRMATGLRNIPSIQSRGLFGAIAGFIEGGW

TGMIDGWYGYHHQNEQGSGYAADQKSTQNAIDGITNKVNSVIEKMNTQFTA

VGKEFNNLERRIENLNKKVDDGFLDIWTYNAELLVLLENERTLDFHDSNVR

NLYEKVKSQLKNNAKEIGNGCFEFYHKCDDACMESVRNGTYDYPKYSEESK

LNREEIDGVKLESMGVYQILAIYSTVASSLVLLVSLGAISFWMCSNGSLQC

RICI

DO2aRBStrunc00_resG63_G277_graftedontoNJ1976
(SEQ ID NO: 10)
MKAKLLVLLCTFTATYADTLCIGYHANNSTDTVDTVLEKNVTVTHSVNLLE

DRHNGKLCKLGGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGSGSGIIISDAPVHDCNTKCQTPKGAINTSL

PFQNIHPVTIGECPKYVKSTKLRMATGLRNIPSIQSRGLFGAIAGFIEGGW

-continued

TGMIDGWYGYHHQNEQGSGYAADQRSTQNAIDGITNKVNSVIEKMNTQFTA

VGKEFNHLEKRIENLNKKVDDGFLDIWTYNAELLVLLENERTLDFHDSNVK

NLYEKVRSQLRNNAKEIGNGCFEFYHKCDDTCMESVKNGTYDYPKYSEESK

LNREEIDGVKLESTRIYQILAIYSTVASSLVLLVSLGAISFWMCSNGSLQC

RICI

DO2aRBStrunc01_resV125_G277_graftedontoDo1a
(SEQ ID NO: 11)

MKAKLLVLLCTFTATYADTICIGYHANNSTDTVDTVLEKNVTVTHSVNLLE

DSHNGKLCKLKGIAPLQLGKCSVAGWILGNPECESLSTASSWSYIVETSSP

DNGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSDTPVHDCNTTCQTPQGAINSSL

PFQNVHPVTIGECPKYVRSAKLRMATGLRNIPSIQSRGLFGAIAGFIEGGW

TGMVDGWYGYHHQNEQGSGYAADLKSTQNAIDGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNNTCMESVKNGTYDYPKYSEESK

LNREKIDGVKLESMGVYQILAIYSTVASSLVLLVSLGAISFWMCSNGSLQC

RICI

DO2aRBStrunc01_resV125_G277_graftedontoCal2009
(SEQ ID NO: 12)

MKAKLLVLLCTFTATYADTLCIGYHANNSTDTVDTVLEKNVTVTHSVNLLE

DKHNGKLCKLRGVAPLHLGKCNIAGWILGNPECESLSTASSWSYIVETPSS

DNGTCYPGDFIDYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGAGSGIIISDTPVHDCNTTCQTPKGAINTSL

PFQNIHPITIGKCPKYVKSTKLRLATGLRNIPSIQSRGLFGAIAGFIEGGW

TGMVDGWYGYHHQNEQGSGYAADLKSTQNAIDEITNKVNSVIEKMNTQFTA

VGKEFNHLEKRIENLNKKVDDGFLDIWTYNAELLVLLENERTLDYHDSNVK

NLYEKVRSQLKNNAKEIGNGCFEFYHKCDNTCMESVKNGTYDYPKYSEEAK

LNREEIDGVKLESTRIYQILAIYSTVASSLVLVVSLGAISFWMCSNGSLQC

RICI

DO2aRBStrunc01_resV125_G277_graftedontoSC1918
(SEQ ID NO: 13)

MKAKLLVLLCTFTATYADTICIGYHANNSTDTVDTVLEKNVTVTHSVNLLE

DSHNGKLCKLKGIAPLQLGKCNIAGWLLGNPECDLLLTASSWSYIVETSNS

ENGTCYPGDFIDYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGSGSGIITSDAPVHDCNTKCQTPHGAINSSL

PFQNIHPVTIGECPKYVRSTKLRMATGLRNIPSIQSRGLFGAIAGFIEGGW

TGMIDGWYGYHHQNEQGSGYAADQKSTQNAIDGITNKVNSVIEKMNTQFTA

VGKEFNNLERRIENLNKKVDDGFLDIWTYNAELLVLLENERTLDFHDSNVR

-continued

NLYEKVKSQLKNNAKEIGNGCFEFYHKCDDACMESVRNGTYDYPKYSEESK

LNREEIDGVKLESMGVYQILAIYSTVASSLVLLVSLGAISFWMCSNGSLQC

RICI

DO2aRBStrunc01_resV125_G277_graftedontoNJ1976
(SEQ ID NO: 14)

MKAKLLVLLCTFTATYADTLCIGYHANNSTDTVDTVLEKNVTVTHSVNLLE

DRHNGKLCKLGGIAPLHLGKCNIAGWLLGNPECELLLTVSSWSYIVETSNS

DNGTCYPGDFINYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGSGSGIIISDAPVHDCNTKCQTPKGAINTSL

PFQNIHPVTIGECPKYVKSTKLRMATGLRNIPSIQSRGLFGAIAGFIEGGW

TGMIDGWYGYHHQNEQGSGYAADQRSTQNAIDGITNKVNSVIEKMNTQFTA

VGKEFNHLEKRIENLNKKVDDGFLDIWTYNAELLVLLENERTLDFHDSNVK

NLYEKVRSQLRNNAKEIGNGCFEFYHKCDDTCMESVKNGTYDYPKYSEESK

LNREEIDGVKLESTRIYQILAIYSTVASSLVLLVSLGAISFWMCSNGSLQC

RICI

DO2aRBStrunc02_resP135_P269_graftedontoDo1a
(SEQ ID NO: 15)

MKAKLLVLLCTFTATYADTICIGYHANNSTDTVDTVLEKNVTVTHSVNLLE

DSHNGKLCKLKGIAPLQLGKCSVAGWILGNPECESLSTASSWSYIVETSSP

DNGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSDTPVHDCNTTCQTPQGAINSSL

PFQNVHPVTIGECPKYVRSAKLRMATGLRNIPSIQSRGLFGAIAGFIEGGW

TGMVDGWYGYHHQNEQGSGYAADLKSTQNAIDGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNNTCMESVKNGTYDYPKYSEESK

LNREKIDGVKLESMGVYQILAIYSTVASSLVLLVSLGAISFWMCSNGSLQC

RICI

DO2aRBStrunc02_resP135_P269_graftedontoCal2009
(SEQ ID NO: 16)

MKAKLLVLLCTFTATYADTLCIGYHANNSTDTVDTVLEKNVTVTHSVNLLE

DKHNGKLCKLRGVAPLHLGKCNIAGWILGNPECESLSTASSWSYIVETPSS

DNGTCYPGDFIDYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPRYAFAMERNAGSGIIISDTPVHDCNTTCQTPKGAINTSL

PFQNIHPITIGKCPKYVKSTKLRLATGLRNIPSIQSRGLFGAIAGFIEGGW

TGMVDGWYGYHHQNEQGSGYAADLKSTQNAIDEITNKVNSVIEKMNTQFTA

VGKEFNHLEKRIENLNKKVDDGFLDIWTYNAELLVLLENERTLDYHDSNVK

NLYEKVRSQLKNNAKEIGNGCFEFYHKCDNTCMESVKNGTYDYPKYSEEAK
LNREEIDGVKLESTRIYQILAIYSTVASSLVLVVSLGAISFWMCSNGSLQC
RICI

DO2aRBStrunc02_resP135_P269_graftedontoSc1918
(SEQ ID NO: 17)
MKAKLLVLLCTFTATYADTICIGYHANNSTDTVDTVLEKNVTVTHSVNLLE

DSHNGKLCKLKGIAPLQLGKCNIAGWLLGNPECDLLLTASSWSYIVETSNS

ENGTCYPGDFIDYEELREQLSSVSSFEKFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALNRGSGSGIITSDAPVHDCNTKCQTPHGAINSSL

PFQNIHPVTIGECPKYVRSTKLRMATGLRNIPSIQSRGLFGAIAGFIEGGW

TGMIDGWYGYHHQNEQGSGYAADQKSTQNAIDGITNKVNSVIEKMNTQFTA

VGKEFNNLERRIENLNKKVDDGFLDIWTYNAELLVLLENERTLDFHDSNVR

NLYEKVKSQLKNNAKEIGNGCFEFYHKCDDACMESVRNGTYDYPKYSEESK

LNREEIDGVKLESMGVYQILAIYSTVASSLVLLVSLGAISFWMCSNGSLQC

RICI

DO2aRBStrunc02_resP135_P269_graftedontoNj1976
(SEQ ID NO: 18)

MKAKLLVLLCTFTATYADTLCIGYHANNSTDTVDTVLEKNVTVTHSVNLLE

DRHNGKLCKLGGIAPLHLGKCNIAGWLLGNPECELLLTVSSWSYIVETSNS

DNGTCYPGDFINYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPRYAFAMNRGSGSGIIISDAPVHDCNTKCQTPKGAINTSL

PFQNIHPVTIGECPKYVKSTKLRMATGLRNIPSIQSRGLFGAIAGFIEGGW

TGMIDGWYGYHHQNEQGSGYAADQRSTQNAIDGITNKVNSVIEKMNTQFTA

VGKEFNHLEKRIENLNKKVDDGFLDIWTYNAELLVLLENERTLDFHDSNVK

NLYEKVRSQLRNNAKEIGNGCFEFYHKCDDTCMESVKNGTYDYPKYSEESK

LNREEIDGVKLESTRIYQILAIYSTVASSLVLLVSLGAISFWMCSNGSLQC

RICI

SMARt_NC_DO2a_NGlyMod
(SEQ ID NO: 19)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHDSNGVSASCS

HNGKSSFYRNLLWLTGKNGLYPKLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGEIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

-continued

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_NGlyMod + loopInsertion(CA09)
(SEQ ID NO: 20)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHDSNKGVSASC

SHNGKSSFYRNLLWLTGKNGLYPKLSKSYANNKEKEVLVLWGVHHPPNIGD

QRALYHTENAYVSVVSSHYSRRFTPEIAKRPKVRDQEGRINYYWTLLEPGD

TIIFEANGNLIAPWYAFALSRGFGSGIITSNAPMDKCDAKCQTPQGAINSS

LPFQNVHPVTIGECPKYVRSAKLRMVTGLRNIPFIQSRGLFGAIAGFIEGG

WTGMVDGWYGYHHQNEQGSGYAADQKSTQNAINGITNKVNSVIEKMNTQFT

AVGKEFNKLERRMENLNKKVDDGFLDIWTYNAELLVLLENERTLDFHDSNV

KNLYEKVKSQLKNNAKEIGNGCFEFYHKCNDECMESVKNGTYDYPKYSEES

KLNREKIDGVKLESMGVYQILAIYSTVASSLVLLVSLGAISFWMCSNGSLQ

CRICI

SMART_NC_DO2A_NGLYMOD + LOOPINSERTION(SC18)
(SEQ ID NO: 21)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHETTKGVSASC

SHNGKSSFYRNLLWLTGKNGLYPKLSKSYANNKEKEVLVLWGVHHPPNIGD

QRALYHTENAYVSVVSSHYSRRFTPEIAKRPKVRDQEGRINYYWTLLEPGD

TIIFEANGNLIAPWYAFALSRGFGSGIITSNAPMDKCDAKCQTPQGAINSS

LPFQNVHPVTIGECPKYVRSAKLRMVTGLRNIPFIQSRGLFGAIAGFIEGG

WTGMVDGWYGYHHQNEQGSGYAADQKSTQNAINGITNKVNSVIEKMNTQFT

AVGKEFNKLERRMENLNKKVDDGFLDIWTYNAELLVLLENERTLDFHDSNV

KNLYEKVKSQLKNNAKEIGNGCFEFYHKCNDECMESVKNGTYDYPKYSEES

KLNREKIDGVKLESMGVYQILAIYSTVASSLVLLVSLGAISFWMCSNGSLQ

CRICI

SMARt_NC_DO2a_mods_outstide_ch65_eptiope1
(SEQ ID NO: 22)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKTSSWPNHTVTGVSASCP

HAGAKSFYRNLLWLTGKNGLYPNLSKSYANNKEKEVLVLWGVHHPPNIGDQ

RALYQNADAYVSVVSSHYSRRFTPEIAKRPKVRDQEGRINYYWTLLEPGDT

IIFEATGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_mods_outstide_ch65_eptiope2

(SEQ ID NO: 23)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHTVTGVSASCP

HAGAKSFYRNLLWLTGKNGLYPNLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_mods_outside_ch65_eptiope3

(SEQ ID NO: 24)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHTVTGVSASCS

HNGKSSFYRNLLWLTGKNGLYPNLSKSYANNKEKEVLVLWGVHHPPNIGDQ

RALYQNADAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_mods_outside_ch65_eptiope1-noGly (SEQ ID NO: 25)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKTSSWPNHNTTGVSASCP

HAGAKSFYRNLLWLTGKNGLYPKLSKSYANNKEKEVLVLWGVHHPPNIGDQ

RALYQNADAYVSVVSSHYSRRFTPEIAKRPKVRDQEGRINYYWTLLEPGDT

IIFEATGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_mods_outstide_ch65_eptiope2-noGly (SEQ ID NO: 26)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHNTTGVSASCP

HAGAKSFYRNLLWLTGKNGLYPKLSKSYANNKEKEVLVLWGVHHPPNIGDQ

RALYHTENAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

SMARt_NC_DO2a_mods_outstide_ch65_eptiope3-noGly (SEQ ID NO: 27)

MKAKLLVLLCTFTATYADTICIGYHANNSTDTVDTVLEKNVTVTHSVNILE

DSHNGKLCLLKGIAPLQLGNCSVAGWILGNPECELLISKESWSYIVEKPNP

ENGTCYPGYFADYEELREQLSSVSSFERFEIFPKESSWPNHNTTGVSASCS

HNGKSSFYRNLLWLTGKNGLYPKLSKSYANNKEKEVLVLWGVHHPPNIGDQ

RALYQNADAYVSVVSSHYSRRFTPEIAKRPKVRDQEGRINYYWTLLEPGDT

IIFEANGNLIAPWYAFALSRGFGSGIITSNAPMDKCDAKCQTPQGAINSSL

PFQNVHPVTIGECPKYVRSAKLRMVTGLRNIPFIQSRGLFGAIAGFIEGGW

TGMVDGWYGYHHQNEQGSGYAADQKSTQNAINGITNKVNSVIEKMNTQFTA

VGKEFNKLERRMENLNKKVDDGFLDIWTYNAELLVLLENERTLDFHDSNVK

NLYEKVKSQLKNNAKEIGNGCFEFYHKCNDECMESVKNGTYDYPKYSEESK

LNREKIDGVKLESMGVYQILAIYSTVASSLVLLVSLGAISFWMCSNGSLQC

RICI

The present application also encompasses modified recombinant HA polypeptides that have an amino acid sequence at least 70%, 75%, 80%, 85%, 90%, 92%, 94%, 95%, 96%, 97%, 98%, or 99% identical to any one of the sequences described herein.

Figures 9, 10:
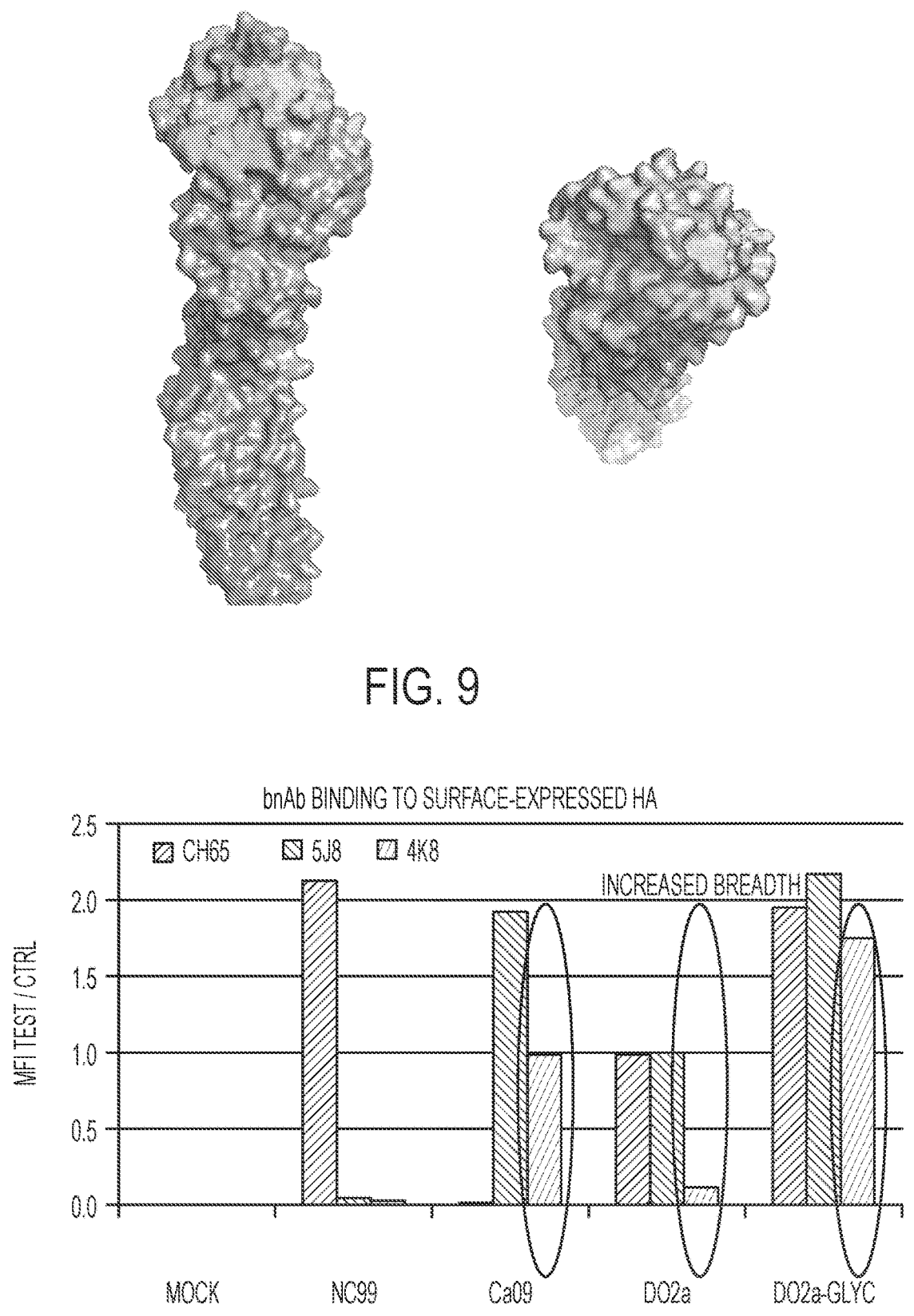

Example 6. Modifications of Recombinant HA Polypeptides to Increase Pandemic Features Further designs were selected to test the effect of DO2a de-glycosylation/RBS modification on breadth of Ab responses and protection against pandemic A/California/09 challenge. Re-engineering of SMARtDO2a RBS improved recognition by broadly neutralizing antibodies as demonstrated by a gain of 4K8 binding to de-glycosylated constructs in an MFI assay (FIG. 10). The original SMARt_DO2a design was seasonal-biased based on in vivo evaluations; we modified the design to expand breadth to pandemic strains. In vitro assays using a panel of mAbs indicated binding of pandemic mAbs to some of the modified designs. A subset of designs was evaluated in a murine challenge model against A/California/07/2009. The results demonstrate the modifications do improve the immune profile against pandemic influenza A.

Immunization of Mice with VLPs Expressing Re-Engineered HAs

Figure 11:
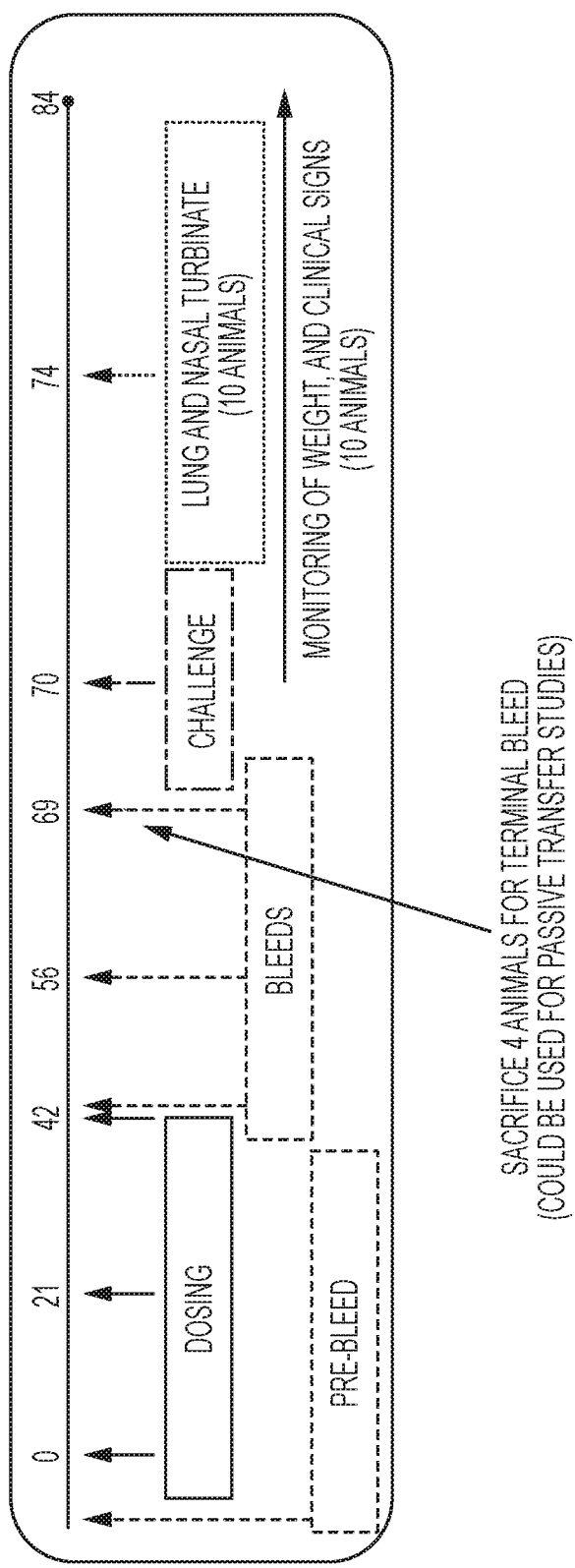
FIG. 11 shows an exemplary timeline for immunizations and subsequent in vivo evaluation.
Figure 15:
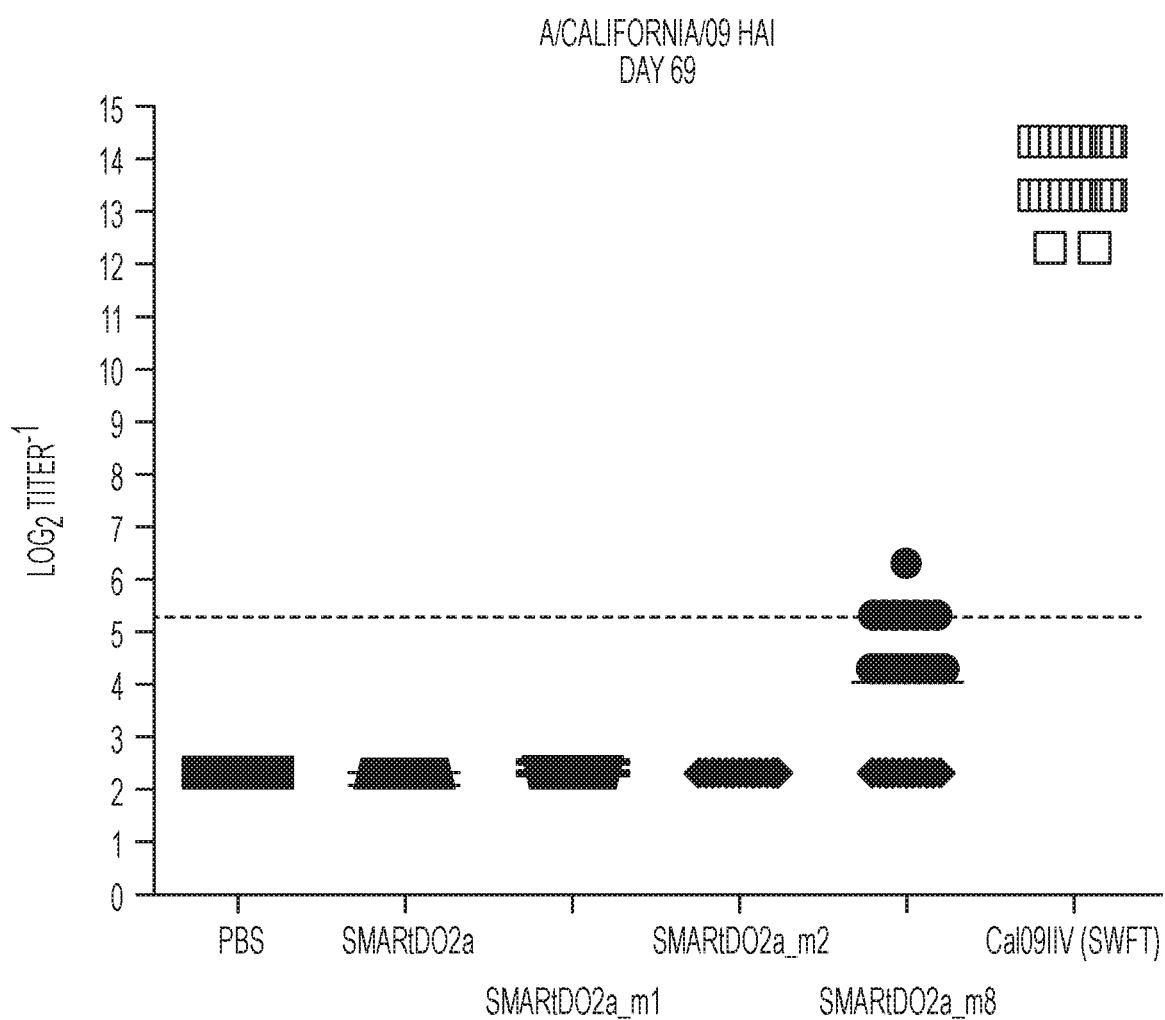
FIG. 15 shows a representative hemagglutination inhibition (HAI) assay results of serum from animals immunized with SMARtDO2a constructs.

To assess immunogenicity of re-engineered mosaic HA designs, groups of 6-8 week old female BALB/c mice are immunized with 3 µg of influenza VLPs or vehicle alone (PBS). All immunizations are formulated as emulsions with an oil-in-water adjuvant, and are delivered intramuscularly in a total volume of 100 µl as shown in Table 10. Each group receives two identical booster doses 21 days and 42 days after the initial immunization. Pre-immune serum is collected from each animal on day 0. Post-immune serum is collected from each animal on days 42, 56, and 69. FIG. 11, demonstrates the timeline for immunizations and subsequent in vivo evaluation. Serum pools used for analysis are prepared by mixing equal volumes of serum from each animal within a group.

indicated virus and incubated at room temperature for 30 minutes in a round bottom plate. Each serum/virus mixture is then mixed with an equal volume of 0.5% turkey erythrocytes in saline. The plates are scored when control wells lacking serum demonstrate complete hemagglutination (~30 min). The HAI titer is defined as the maximum serum dilution resulting in complete inhibition of hemagglutination in 50% of the wells tested. A/California/09 HAI responses in SMARtDO2a_m8 mice were significantly different to PBS (P<0.001), however only 6/24 mice had HAI titer equal or higher than 1:40 (FIG. 15). The mechanism of protection for all other DO2a constructs is unclear.

All next generation modified DO2a constructs were able to partially protect against mortality upon A/California/09 challenge. SMARtDO2a_m8 showed the best reduction in mortality, weight loss and viral lung titer. SMARtDO2a_m8 was also the only DO2a construct to elicit HAI responses against A/Cal/09 strain, suggesting that improved protection might have been associated to head responses. As demon-

TABLE 10

| Group | n[1] | Antigen (day 0) | Antigen (day 21) | Antigen (day 42) | Dose (µg) | Adjuvant | Injection Route | Challenge (day 70) |
|---|---|---|---|---|---|---|---|---|
| 1 | 24 | PBS | PBS | PBS | NA | AF03 | IM | A/Cal/2009 |
| 2 | 24 | VLP-SMARtDO2a | VLP-SMARtDO2a | VLP-SMARtDO2a | 3 | AF03 | IM | A/Cal/2009 |
| 3 | 24 | VLP-SMARtDO2a_m1 | VLP-SMARtDO2a_m1 | VLP-SMARtDO2a_m1 | 3 | AF03 | IM | A/Cal/2009 |
| 4 | 24 | VLP-SMARtDO2a_m2 | VLP-SMARtDO2a_m2 | VLP-SMARtDO2a_m2 | 3 | AF03 | IM | A/Cal/2009 |
| 5 | 24 | VLP-SMARtDO2a_m8 | VLP-SMARtDO2a_m8 | VLP-SMARtDO2a_m8 | 3 | AF03 | IM | A/Cal/2009 |
| 6 | 24 | Cal09 IIV (SWFT) | Cal09 IIV (SWFT) | Cal09 IIV (SWFT) | 1.5 | AF03 | IM | A/Cal/2009 |

Figure 12:
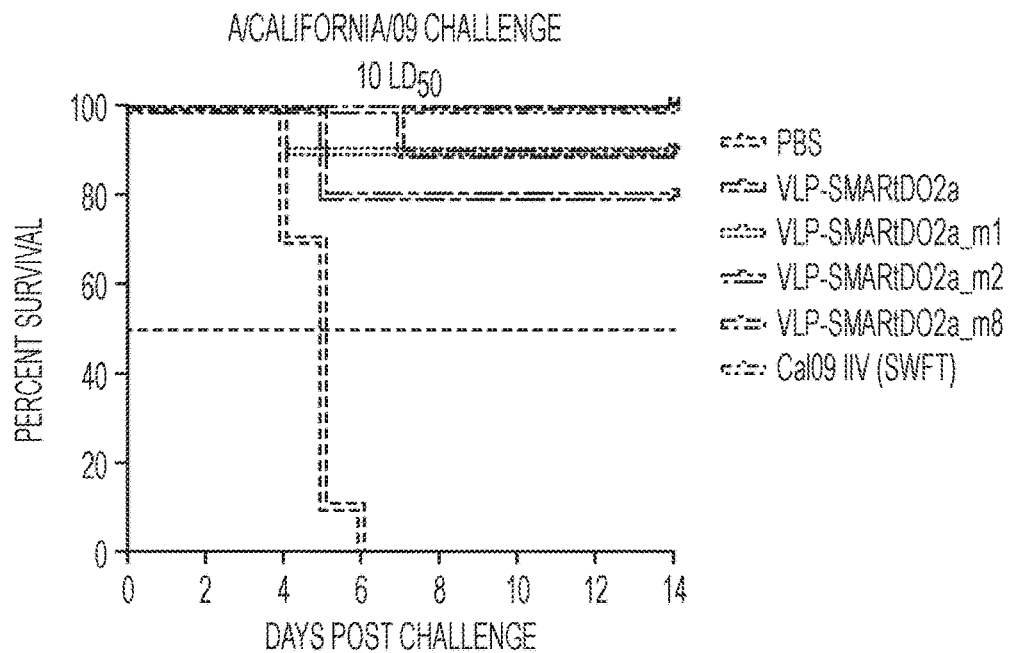

Survival and Body Weight of Mice Immunized with VLPs Expressing Re-Engineered HAs Animals were challenged with ten times the $LD_{50}$ of pandemic A/California/2009 on day 70 and mortality was monitored post challenge. Immunization with original SMARtDO2a was protective against A/California/09 challenge in which 80% of the animals survived 14 days post challenge compared to the animals immunized with vehicle alone resulting in 100% mortality by day 6 post challenge. Next generation DO2a modifications improved survival in comparison to original SMARtDO2a in which immunization with SMARtDO2a_m8 was effective in protection of 100% of the animals tested (FIG. 12).

Figure 13:
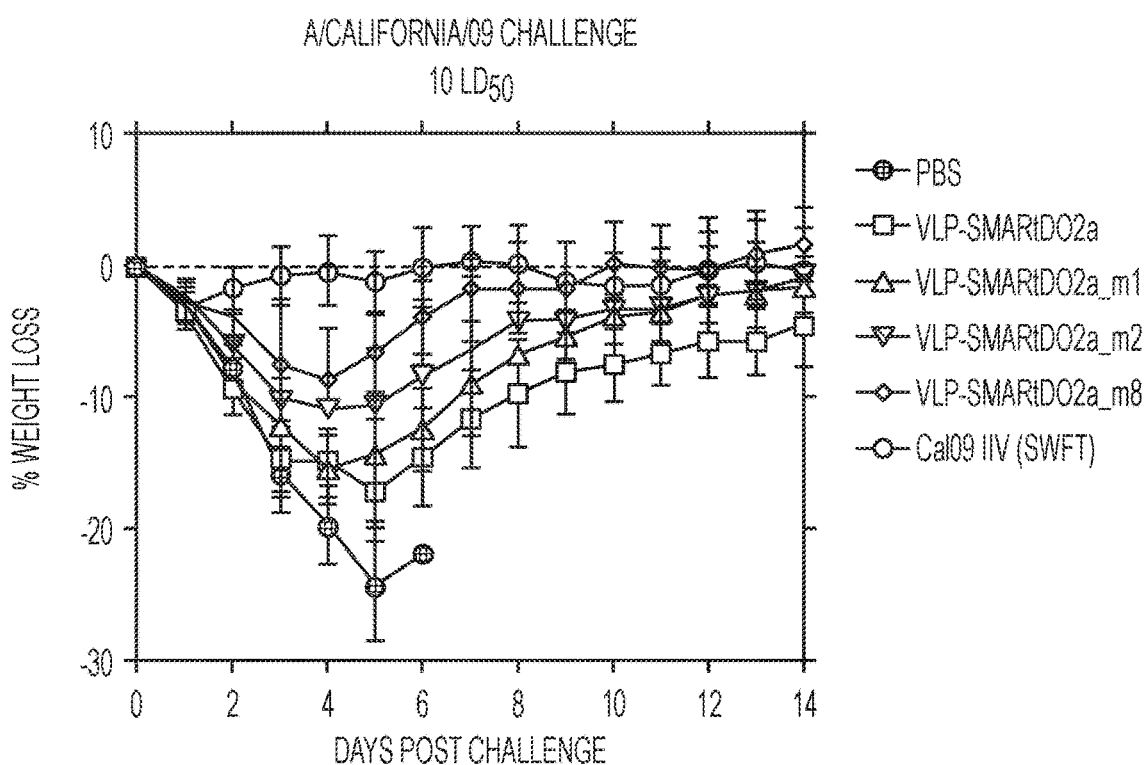

Animals were monitored for the percentage of body weight loss post viral challenge. Next generation DO2a modifications improved body weight maintenance in comparison to original SMARtDO2a. SMARtDO2a_m8 offered the best protection against viral challenge induced weight loss (FIG. 13).

Viral Lung Titers of Mice Immunized with VLPs Expressing Re-Engineered HAs

Figure 14:
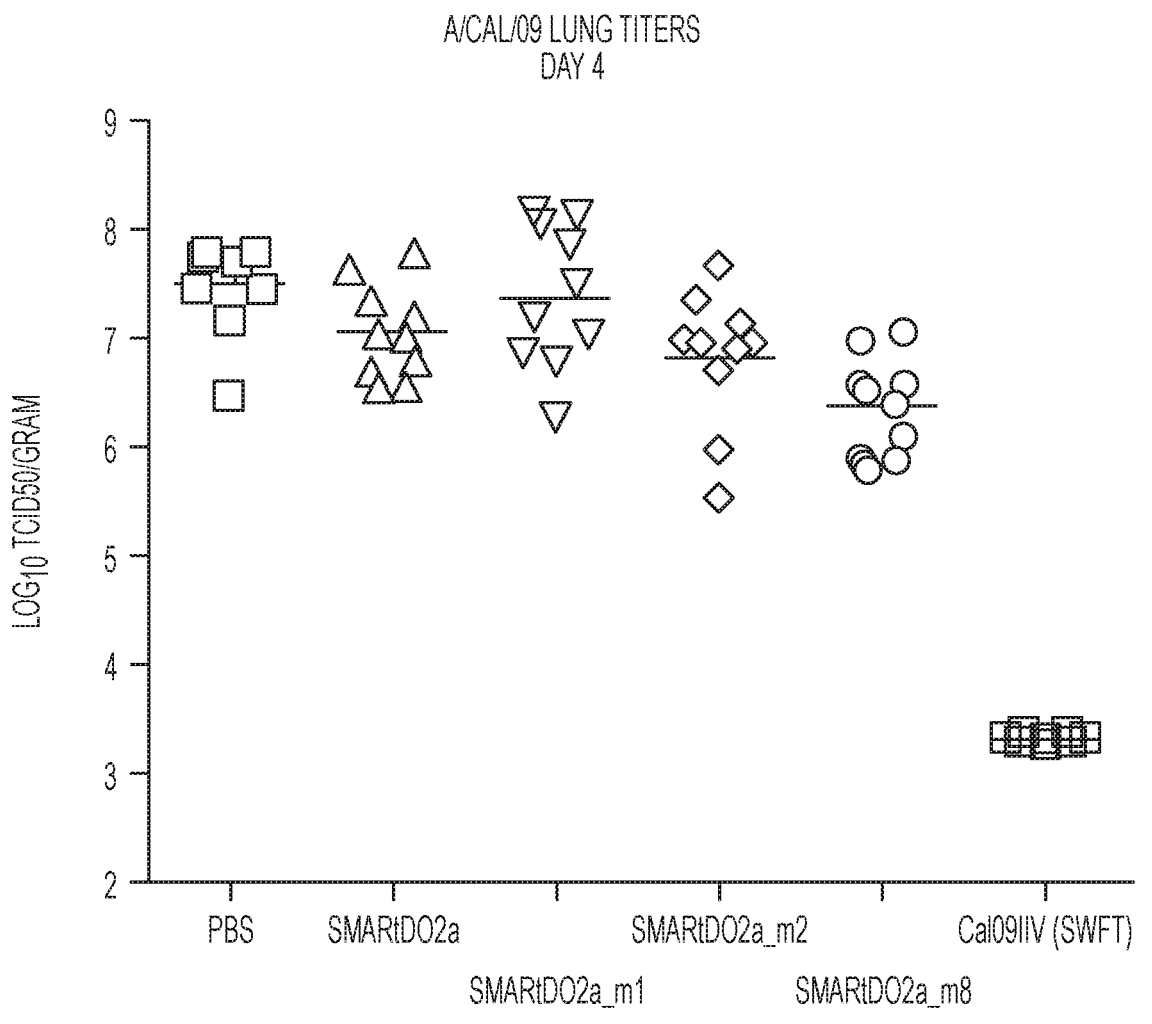

Mice were further monitored for viral lung titers on day 4 post challenge. Immunization with SMARtDO2a constructs resulted in lower viral lung titers compared to PBS. The SMARtDO2a_m8 construct resulted in 10-fold reduction of lung titers compared to PBS and significantly lower viral lung titers than all other DO2a constructs (FIG. 14).

Hemagglutination Inhibition (HAI) Assay

Replicate serial dilutions of pooled serum from each group are mixed with 4 hemagglutination units of the strated herein, next generation DO2a modifications were successful in increasing protection against pandemic influenza A challenge.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

---

We claim:

1. A method of altering the immunogenic profile of an engineered hemagglutinin (HA) polypeptide, comprising
obtaining an engineered HA polypeptide engineered by a mosaic technology, deletion and/or rearrangement of structural domains, domain swapping, or combinations of neutralizing or cross-reactive epitopes among multiple influenza strains,
identifying the presence or absence of one or more putative N-linked glycosylation sites in a head region of the engineered HA polypeptide, wherein the head region corresponds to residues 63-278, 125-277 or 135-269 of SEQ ID NO: 1 according to California 09 Numbering (CA09 Numbering);
introducing into the head region of the engineered HA polypeptide one or more amino acid substitutions, deletions or insertions to disrupt the one or more putative N-linked glycosylation sites or insert additional N-linked glycosylation sites,
introducing one or more amino acid substitutions in the region of or adjacent to the Receptor Binding Site (RBS) region
thereby generating a re-engineered HA polypeptide with altered immunogenic profile.

2. The method of claim 1, wherein the RBS comprises all amino acids residues within 15 angstroms of a position corresponding to W167 (CA09 Numbering) in a three-dimensional (3-D) structure.

3. The method of claim 1, wherein the RBS comprises the epitope bound by the paratope of monoclonal antibody CH65.

4. The method of claim 1, wherein the one or more putative or additional N-linked glycosylation sites are defined by a consensus sequence of NxS/Ty, wherein x and y are not P.

5. The method of claim 1, wherein the immunogenic profile of the engineered HA polypeptide is more seasonal and the immunogenic profile of the re-engineered HA polypeptide is more pandemic.

6. The method of claim 1, wherein the immunogenic profile of the engineered HA polypeptide is more pandemic and the immunogenic profile of the re-engineered HA polypeptide is more seasonal.

7. The method of claim 1, wherein the one or more modifications occur at positions corresponding to 137, 144, 145, 154, 155, 156, 157, 158, 159, 177, 210, 211, 212, 213, 214, 244, 245, and/or 262 according to CA09 Numbering.

8. The method of claim 1, wherein the one or more modifications occur at positions corresponding to 137, 144, 145, 154, 155, 156, 157, 158, 159, 177, 210, 211, 212, 213, and/or 214 according to CA09 Numbering.

9. The method of claim 1, further comprising assessing expression and conformation of the re-engineered HA polypeptide.

10. The method of claim 1, further comprising determining if the re-engineered HA polypeptide elicits neutralizing antibodies against both seasonal and pandemic strains of influenza virus.

11. The method of claim 1, wherein generating a re-engineered HA polypeptide with altered immunogenic profile comprises increasing the binding of one or more anti-head monoclonal antibodies against seasonal and/or pandemic influenza strains.

12. The method of claim 1, wherein generating a re-engineered HA polypeptide with altered immunogenic profile comprises increasing the breadth of binding of anti-head monoclonal antibodies against pandemic influenza strains.

13. The method of claim 11, wherein increases in binding are determined by flow cytometry detection of the monoclonal antibodies bound to re-engineered HA polypeptides expressed on the surface of mammalian cells.

14. The method of claim 13, further comprising quantitating the level of monoclonal antibody binding.

* * * * *

SEQUENCE LISTING

```
<160> NUMBER OF SEQ ID NOS: 37

<210> SEQ ID NO 1
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
```

```
                260                 265                 270
Leu Ser Arg Gly Phe Gly Ser Gly Ile Ile Thr Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
            325                 330                 335

Ile Pro Phe Ile Gln Ser Arg Gly Leu Phe Gly Ala Ile Ala Gly Phe
        340                 345                 350

Ile Glu Gly Gly Trp Thr Gly Met Val Asp Gly Trp Tyr Gly Tyr His
    355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 2
<211> LENGTH: 566
<212> TYPE: PRT
<213> ORGANISM: Influenza A virus
<220> FEATURE:
<221> NAME/KEY: MOD_RES
<222> LOCATION: (239)..(240)
<223> OTHER INFORMATION: Any amino acid

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

```
Leu Leu Glu Asp Lys His Asn Gly Lys Leu Cys Lys Leu Arg Gly Val
     50                  55                  60

Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
             100                 105                 110

Ile Asp Tyr Glu Glu Leu Arg Glu Gln Leu Ser Ser Val Ser Ser Phe
         115                 120                 125

Glu Arg Phe Glu Ile Phe Pro Lys Thr Ser Ser Trp Pro Asn His Asp
     130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                 165                 170                 175

Lys Leu Ser Lys Ser Tyr Ile Asn Asp Lys Gly Lys Glu Val Leu Val
             180                 185                 190

Leu Trp Gly Ile His His Pro Ser Thr Ser Ala Asp Gln Gln Ser Leu
         195                 200                 205

Tyr Gln Asn Ala Asp Ala Tyr Val Phe Val Gly Ser Ser Arg Tyr Ser
     210                 215                 220

Lys Lys Phe Lys Pro Glu Ile Ala Ile Arg Pro Lys Val Arg Xaa Xaa
225                 230                 235                 240

Glu Gly Arg Met Asn Tyr Tyr Trp Thr Leu Val Glu Pro Gly Asp Lys
                 245                 250                 255

Ile Thr Phe Glu Ala Thr Gly Asn Leu Val Val Pro Arg Tyr Ala Phe
             260                 265                 270

Ala Met Glu Arg Asn Ala Gly Ser Gly Ile Ile Ile Ser Asp Thr Pro
         275                 280                 285

Val His Asp Cys Asn Thr Thr Cys Gln Thr Pro Lys Gly Ala Ile Asn
     290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                 325                 330                 335

Asn Ile Pro Ser Ile Gln Ser Arg Gly Leu Phe Gly Ala Ile Ala Gly
             340                 345                 350

Phe Ile Glu Gly Gly Trp Thr Gly Met Val Asp Gly Trp Tyr Gly Tyr
         355                 360                 365

His His Gln Asn Glu Gln Gly Ser Gly Tyr Ala Ala Asp Leu Lys Ser
     370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                 405                 410                 415

Leu Glu Lys Arg Ile Glu Asn Leu Asn Lys Lys Val Asp Asp Gly Phe
             420                 425                 430

Leu Asp Ile Trp Thr Tyr Asn Ala Glu Leu Leu Val Leu Leu Glu Asn
         435                 440                 445

Glu Arg Thr Leu Asp Tyr His Asp Ser Asn Val Lys Asn Leu Tyr Glu
     450                 455                 460
```

-continued

```
Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Thr Arg Ile Tyr
    515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
            565
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
```

-continued

```
                130                 135                 140
Ser Asn Gly Val Thr Ala Ser Cys Pro His Ala Gly Ala Lys Ser Phe
145                 150                 155                 160

Tyr Arg Asn Leu Leu Trp Leu Val Lys Lys Gly Asn Ser Tyr Pro Lys
                165                 170                 175

Leu Ser Lys Ser Tyr Ile Asn Asp Lys Gly Lys Glu Val Leu Val Leu
                180                 185                 190

Trp Gly Val His His Pro Ser Thr Ser Ala Asp Gln Gln Ser Leu Tyr
                195                 200                 205

Gln Asn Ala Asn Ala Tyr Val Ser Val Val Thr Ser Arg Tyr Ser Arg
210                 215                 220

Arg Phe Thr Pro Glu Ile Ala Ile Arg Pro Lys Val Arg Asp Gln Glu
225                 230                 235                 240

Gly Arg Met Asn Tyr Tyr Trp Thr Leu Val Glu Pro Gly Asp Thr Ile
                245                 250                 255

Ile Phe Glu Ala Thr Gly Asn Leu Ile Ala Pro Trp Tyr Ala Phe Ala
                260                 265                 270

Leu Ser Arg Gly Phe Gly Ser Gly Ile Ile Thr Ser Asp Thr Pro Val
                275                 280                 285

His Asp Cys Asn Thr Thr Cys Gln Thr Pro Gln Gly Ala Ile Asn Ser
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Leu Lys Ser Thr
                370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
                435                 440                 445

Arg Thr Leu Asp Phe His Asp Ser Asn Val Lys Asn Leu Tyr Glu Lys
                450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560
```

Cys Arg Ile Cys Ile
              565

<210> SEQ ID NO 7
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

-continued

```
Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 8
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
```

```
            115                 120                 125
Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Arg Ala Leu Tyr
                195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Ala Gly Ser Gly Ile Ile Ile Ser Asp Thr Pro Val
                275                 280                 285

His Asp Cys Asn Thr Thr Cys Gln Thr Pro Lys Gly Ala Ile Asn Thr
290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Leu Lys Ser Thr
                370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
                435                 440                 445

Arg Thr Leu Asp Tyr His Asp Ser Asn Val Lys Asn Leu Tyr Glu Lys
                450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
                500                 505                 510

Arg Glu Glu Ile Asp Gly Val Lys Leu Glu Ser Thr Arg Ile Tyr Gln
                515                 520                 525

Ile Leu Ala Ile Tyr Ser Thr Val Ala Ser Ser Leu Val Leu Val Val
530                 535                 540
```

```
Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 9
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Ser Gly Ser Gly Ile Ile Thr Ser Asp Ala Pro Val
            275                 280                 285

His Asp Cys Asn Thr Lys Cys Gln Thr Pro His Gly Ala Ile Asn Ser
            290                 295                 300

Ser Leu Pro Phe Gln Asn Ile His Pro Val Thr Ile Gly Glu Cys Pro
305                 310                 315                 320
```

Lys Tyr Val Arg Ser Thr Lys Leu Arg Met Ala Thr Gly Leu Arg Asn
            325                 330                 335

Ile Pro Ser Ile Gln Ser Arg Gly Leu Phe Gly Ala Ile Ala Gly Phe
        340                 345                 350

Ile Glu Gly Gly Trp Thr Gly Met Ile Asp Gly Trp Tyr Gly Tyr His
    355                 360                 365

His Gln Asn Glu Gln Gly Ser Gly Tyr Ala Ala Asp Gln Lys Ser Thr
370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Arg Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asp Ala Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 10
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Arg His Asn Gly Lys Leu Cys Lys Leu Gly Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe

-continued

```
                100              105              110
Ala Asp Tyr Glu Glu Leu Arg Glu Gln Leu Ser Ser Val Ser Ser Phe
            115              120              125

Glu Arg Phe Glu Ile Phe Pro Lys Glu Ser Ser Trp Pro Asn His Thr
        130              135              140

Val Thr Gly Val Ser Ala Ser Cys Ser His Asn Gly Lys Ser Ser Phe
145              150              155              160

Tyr Arg Asn Leu Leu Trp Leu Thr Gly Lys Asn Gly Leu Tyr Pro Asn
                165              170              175

Leu Ser Lys Ser Tyr Ala Asn Asn Lys Glu Lys Glu Val Leu Val Leu
            180              185              190

Trp Gly Val His His Pro Pro Asn Ile Gly Asp Gln Arg Ala Leu Tyr
        195              200              205

His Thr Glu Asn Ala Tyr Val Ser Val Val Ser Ser His Tyr Ser Arg
    210              215              220

Arg Phe Thr Pro Glu Ile Ala Lys Arg Pro Lys Val Arg Asp Gln Glu
225              230              235              240

Gly Arg Ile Asn Tyr Tyr Trp Thr Leu Leu Glu Pro Gly Asp Thr Ile
                245              250              255

Ile Phe Glu Ala Asn Gly Asn Leu Ile Ala Pro Trp Tyr Ala Phe Ala
            260              265              270

Leu Ser Arg Gly Ser Gly Ser Gly Ile Ile Ser Asp Ala Pro Val
        275              280              285

His Asp Cys Asn Thr Lys Cys Gln Thr Pro Lys Gly Ala Ile Asn Thr
    290              295              300

Ser Leu Pro Phe Gln Asn Ile His Pro Val Thr Ile Gly Glu Cys Pro
305              310              315              320

Lys Tyr Val Lys Ser Thr Lys Leu Arg Met Ala Thr Gly Leu Arg Asn
                325              330              335

Ile Pro Ser Ile Gln Ser Arg Gly Leu Phe Gly Ala Ile Ala Gly Phe
            340              345              350

Ile Glu Gly Gly Trp Thr Gly Met Ile Asp Gly Trp Tyr Gly Tyr His
        355              360              365

His Gln Asn Glu Gln Gly Ser Gly Tyr Ala Ala Asp Gln Arg Ser Thr
    370              375              380

Gln Asn Ala Ile Asp Gly Ile Thr Asn Lys Val Asn Ser Val Ile Glu
385              390              395              400

Lys Met Asn Thr Gln Phe Thr Ala Val Gly Lys Glu Phe Asn His Leu
                405              410              415

Glu Lys Arg Ile Glu Asn Leu Asn Lys Lys Val Asp Asp Gly Phe Leu
            420              425              430

Asp Ile Trp Thr Tyr Asn Ala Glu Leu Leu Val Leu Leu Glu Asn Glu
        435              440              445

Arg Thr Leu Asp Phe His Asp Ser Asn Val Lys Asn Leu Tyr Glu Lys
    450              455              460

Val Arg Ser Gln Leu Arg Asn Asn Ala Lys Glu Ile Gly Asn Gly Cys
465              470              475              480

Phe Glu Phe Tyr His Lys Cys Asp Asp Thr Cys Met Glu Ser Val Lys
                485              490              495

Asn Gly Thr Tyr Asp Tyr Pro Lys Tyr Ser Glu Glu Ser Lys Leu Asn
            500              505              510

Arg Glu Glu Ile Asp Gly Val Lys Leu Glu Ser Thr Arg Ile Tyr Gln
        515              520              525
```

```
Ile Leu Ala Ile Tyr Ser Thr Val Ala Ser Ser Leu Val Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 11
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
    290                 295                 300
```

```
Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
            325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 12
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
```

```
                85                  90                  95
Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ala Gly Ser Gly Ile Ile Ser Asp Thr Pro Val
        275                 280                 285

His Asp Cys Asn Thr Thr Cys Gln Thr Pro Lys Gly Ala Ile Asn Thr
    290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510
```

-continued

Arg Glu Glu Ile Asp Gly Val Lys Leu Glu Ser Thr Arg Ile Tyr Gln
            515                 520                 525

Ile Leu Ala Ile Tyr Ser Thr Val Ala Ser Ser Leu Val Leu Val Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 13
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
            50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
            210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ser Gly Ser Gly Ile Ile Thr Ser Asp Ala Pro Val
            275                 280                 285

His Asp Cys Asn Thr Lys Cys Gln Thr Pro His Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Arg Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asp Ala Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 14
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Arg His Asn Gly Lys Leu Cys Lys Leu Gly Gly Ile
    50                  55                  60

Ala Pro Leu His Leu Gly Lys Cys Asn Ile Ala Gly Trp Leu Leu Gly

```
                65                  70                  75                  80
Asn Pro Glu Cys Glu Leu Leu Leu Thr Val Ser Ser Trp Ser Tyr Ile
                        85                  90                  95

Val Glu Thr Ser Asn Ser Asp Asn Gly Thr Cys Tyr Pro Gly Asp Phe
                    100                 105                 110

Ile Asn Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
        210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ser Gly Ser Gly Ile Ile Ile Ser Asp Ala Pro Val
        275                 280                 285

His Asp Cys Asn Thr Lys Cys Gln Thr Pro Lys Gly Ala Ile Asn Thr
        290                 295                 300

Ser Leu Pro Phe Gln Asn Ile His Pro Val Thr Ile Gly Glu Cys Pro
305                 310                 315                 320

Lys Tyr Val Lys Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Arg Ser Thr
        370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Arg Ser Gln Leu Arg Asn Asn Ala Lys Glu Ile Gly Asn Gly Cys
465                 470                 475                 480

Phe Glu Phe Tyr His Lys Cys Asp Asp Thr Cys Met Glu Ser Val Lys
                485                 490                 495
```

```
Asn Gly Thr Tyr Asp Tyr Pro Lys Tyr Ser Glu Ser Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 15
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270
```

```
Leu Ser Arg Gly Phe Gly Ser Gly Ile Ile Thr Ser Asp Thr Pro Val
            275                 280                 285

His Asp Cys Asn Thr Thr Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 16
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
```

```
                50                  55                  60
Ala Pro Leu His Leu Gly Lys Cys Asn Ile Ala Gly Trp Ile Leu Gly
 65                  70                  75                  80
Asn Pro Glu Cys Glu Ser Leu Ser Thr Ala Ser Ser Trp Ser Tyr Ile
                    85                  90                  95
Val Glu Thr Pro Ser Ser Asp Asn Gly Thr Cys Tyr Pro Gly Asp Phe
                100                 105                 110
Ile Asp Tyr Glu Glu Leu Arg Glu Gln Leu Ser Ser Val Ser Ser Phe
                115                 120                 125
Glu Arg Phe Glu Ile Phe Pro Lys Glu Ser Ser Trp Pro Asn His Thr
            130                 135                 140
Val Thr Gly Val Ser Ala Ser Cys Ser His Asn Gly Lys Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
                180                 185                 190
Trp Gly Val His His Pro Pro Asn Ile Gly Asp Gln Arg Ala Leu Tyr
            195                 200                 205
His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Met Glu Arg Asn Ala Gly Ser Gly Ile Ile Ile Ser Asp Thr Pro Val
            275                 280                 285
His Asp Cys Asn Thr Thr Cys Gln Thr Pro Lys Gly Ala Ile Asn Thr
    290                 295                 300
Ser Leu Pro Phe Gln Asn Ile His Pro Ile Thr Ile Gly Lys Cys Pro
305                 310                 315                 320
Lys Tyr Val Lys Ser Thr Lys Leu Arg Leu Ala Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Leu Lys Ser Thr
    370                 375                 380
Gln Asn Ala Ile Asp Glu Ile Thr Asn Lys Val Asn Ser Val Ile Glu
385                 390                 395                 400
Lys Met Asn Thr Gln Phe Thr Ala Val Gly Lys Glu Phe Asn His Leu
                405                 410                 415
Glu Lys Arg Ile Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Tyr His Asp Ser Asn Val Lys Asn Leu Tyr Glu Lys
    450                 455                 460
Val Arg Ser Gln Leu Lys Asn Asn Ala Lys Glu Ile Gly Asn Gly Cys
465                 470                 475                 480
```

```
Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 17
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255
```

```
Ile Phe Glu Ala Asn Gly Asn Leu Ile Ala Pro Trp Tyr Ala Phe Ala
            260                 265                 270

Leu Asn Arg Gly Ser Gly Ser Gly Ile Ile Thr Ser Asp Ala Pro Val
        275                 280                 285

His Asp Cys Asn Thr Lys Cys Gln Thr Pro His Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Arg Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asp Ala Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 18
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
            35                  40                  45
Leu Leu Glu Asp Arg His Asn Gly Lys Leu Cys Lys Leu Gly Gly Ile
 50                  55                  60
Ala Pro Leu His Leu Gly Lys Cys Asn Ile Ala Gly Trp Leu Leu Gly
 65                  70                  75                  80
Asn Pro Glu Cys Glu Leu Leu Leu Thr Val Ser Ser Trp Ser Tyr Ile
                 85                  90                  95
Val Glu Thr Ser Asn Ser Asp Asn Gly Thr Cys Tyr Pro Gly Asp Phe
                100                 105                 110
Ile Asn Tyr Glu Glu Leu Arg Glu Gln Leu Ser Ser Val Ser Ser Phe
                115                 120                 125
Glu Arg Phe Glu Ile Phe Pro Lys Glu Ser Ser Trp Pro Asn His Thr
                130                 135                 140
Val Thr Gly Val Ser Ala Ser Cys Ser His Asn Gly Lys Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
                180                 185                 190
Trp Gly Val His His Pro Pro Asn Ile Gly Asp Gln Arg Ala Leu Tyr
                195                 200                 205
His Thr Glu Asn Ala Tyr Val Ser Val Val Ser Ser His Tyr Ser Arg
210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
                260                 265                 270
Met Asn Arg Gly Ser Gly Ser Gly Ile Ile Ser Asp Ala Pro Val
                275                 280                 285
His Asp Cys Asn Thr Lys Cys Gln Thr Pro Lys Gly Ala Ile Asn Thr
                290                 295                 300
Ser Leu Pro Phe Gln Asn Ile His Pro Val Thr Ile Gly Glu Cys Pro
305                 310                 315                 320
Lys Tyr Val Lys Ser Thr Lys Leu Arg Met Ala Thr Gly Leu Arg Asn
                325                 330                 335
Ile Pro Ser Ile Gln Ser Arg Gly Leu Phe Gly Ala Ile Ala Gly Phe
                340                 345                 350
Ile Glu Gly Gly Trp Thr Gly Met Ile Asp Gly Trp Tyr Gly Tyr His
                355                 360                 365
His Gln Asn Glu Gln Gly Ser Gly Tyr Ala Ala Asp Gln Arg Ser Thr
                370                 375                 380
Gln Asn Ala Ile Asp Gly Ile Thr Asn Lys Val Asn Ser Val Ile Glu
385                 390                 395                 400
Lys Met Asn Thr Gln Phe Thr Ala Val Gly Lys Glu Phe Asn His Leu
                405                 410                 415
Glu Lys Arg Ile Glu Asn Leu Asn Lys Lys Val Asp Asp Gly Phe Leu
                420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
                450                 455                 460
```

```
Val Arg Ser Gln Leu Arg Asn Asn Ala Lys Glu Ile Gly Asn Gly Cys
465                 470                 475                 480

Phe Glu Phe Tyr His Lys Cys Asp Asp Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 19
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asp
130                 135                 140

Ser Asn Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Lys
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240
```

Gly Arg Ile Asn Tyr Tyr Trp Thr Leu Leu Glu Pro Gly Asp Thr Ile
            245                 250                 255

Ile Phe Glu Ala Asn Gly Asn Leu Ile Ala Pro Trp Tyr Ala Phe Ala
        260                 265                 270

Leu Ser Arg Gly Phe Gly Ser Gly Ile Ile Thr Ser Asn Ala Pro Met
    275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 20
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr

```
            20                  25                  30
Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
            50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                    85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asp
            130                 135                 140

Ser Asn Lys Gly Val Ser Ala Ser Cys Ser His Asn Gly Lys Ser Ser
145                 150                 155                 160

Phe Tyr Arg Asn Leu Leu Trp Leu Thr Gly Lys Asn Gly Leu Tyr Pro
                    165                 170                 175

Lys Leu Ser Lys Ser Tyr Ala Asn Asn Lys Glu Lys Glu Val Leu Val
            180                 185                 190

Leu Trp Gly Val His His Pro Pro Asn Ile Gly Asp Gln Arg Ala Leu
            195                 200                 205

Tyr His Thr Glu Asn Ala Tyr Val Ser Val Val Ser Ser His Tyr Ser
            210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                    245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Pro
            275                 280                 285

Met Asp Lys Cys Asp Ala Lys Cys Gln Thr Pro Gln Gly Ala Ile Asn
            290                 295                 300

Ser Ser Leu Pro Phe Gln Asn Val His Pro Val Thr Ile Gly Glu Cys
305                 310                 315                 320

Pro Lys Tyr Val Arg Ser Ala Lys Leu Arg Met Val Thr Gly Leu Arg
                    325                 330                 335

Asn Ile Pro Phe Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                    405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445
```

```
Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
                485                 490                 495

Lys Asn Gly Thr Tyr Asp Tyr Pro Lys Tyr Ser Glu Ser Lys Leu
                500                 505                 510

Asn Arg Glu Lys Ile Asp Gly Val Lys Leu Glu Ser Met Gly Val Tyr
                515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 21
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Glu
    130                 135                 140

Thr Thr Lys Gly Val Ser Ala Ser Cys Ser His Asn Gly Lys Ser Ser
145                 150                 155                 160

Phe Tyr Arg Asn Leu Leu Trp Leu Thr Gly Lys Asn Gly Leu Tyr Pro
                165                 170                 175

Lys Leu Ser Lys Ser Tyr Ala Asn Asn Lys Glu Lys Glu Val Leu Val
                180                 185                 190

Leu Trp Gly Val His His Pro Pro Asn Ile Gly Asp Gln Arg Ala Leu
                195                 200                 205

Tyr His Thr Glu Asn Ala Tyr Val Ser Val Val Ser Ser His Tyr Ser
    210                 215                 220
```

```
Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
            245                 250                 255

Ile Ile Phe Glu Ala Asn Gly Asn Leu Ile Ala Pro Trp Tyr Ala Phe
        260                 265                 270

Ala Leu Ser Arg Gly Phe Gly Ser Gly Ile Ile Thr Ser Asn Ala Pro
    275                 280                 285

Met Asp Lys Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Ala Lys Leu Arg Met Val Thr Gly Leu Arg
            325                 330                 335

Asn Ile Pro Phe Ile Gln Ser Arg Gly Leu Phe Gly Ala Ile Ala Gly
        340                 345                 350

Phe Ile Glu Gly Gly Trp Thr Gly Met Val Asp Gly Trp Tyr Gly Tyr
    355                 360                 365

His His Gln Asn Glu Gln Gly Ser Gly Tyr Ala Ala Asp Gln Lys Ser
370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
            405                 410                 415

Leu Glu Arg Arg Met Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
    435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
            485                 490                 495

Lys Asn Gly Thr Tyr Asp Tyr Pro Lys Tyr Ser Glu Glu Ser Lys Leu
        500                 505                 510

Asn Arg Glu Lys Ile Asp Gly Val Lys Leu Glu Ser Met Gly Val Tyr
    515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 22
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Lys Ala Lys Leu Leu Val Leu Leu Cys Thr Phe Thr Ala Thr Tyr
```

-continued

```
1               5                   10                  15
Ala Asp Thr Ile Cys Ile Gly Tyr His Ala Asn Asn Ser Thr Asp Thr
                20                  25                  30
Val Asp Thr Val Leu Glu Lys Asn Val Thr Val Thr His Ser Val Asn
                35                  40                  45
Ile Leu Glu Asp Ser His Asn Gly Lys Leu Cys Leu Leu Lys Gly Ile
    50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
Val Glu Lys Pro Asn Pro Glu Asn Gly Thr Cys Tyr Pro Gly Tyr Phe
                100                 105                 110
Ala Asp Tyr Glu Glu Leu Arg Glu Gln Leu Ser Ser Val Ser Ser Phe
                115                 120                 125
Glu Arg Phe Glu Ile Phe Pro Lys Thr Ser Ser Trp Pro Asn His Thr
                130                 135                 140
Val Thr Gly Val Ser Ala Ser Cys Pro His Ala Gly Ala Lys Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
                180                 185                 190
Trp Gly Val His His Pro Pro Asn Ile Gly Asp Gln Arg Ala Leu Tyr
                195                 200                 205
Gln Asn Ala Asp Ala Tyr Val Ser Val Val Ser Ser His Tyr Ser Arg
                210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Thr Gly Asn Leu Ile Ala Pro Trp Tyr Ala Phe Ala
                260                 265                 270
Leu Ser Arg Gly Phe Gly Ser Gly Ile Ile Thr Ser Asn Ala Pro Met
                275                 280                 285
Asp Lys Cys Asp Ala Lys Cys Gln Thr Pro Gln Gly Ala Ile Asn Ser
                290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Phe Ile Gln Ser Arg Gly Leu Phe Gly Ala Ile Ala Gly Phe
                340                 345                 350
Ile Glu Gly Gly Trp Thr Gly Met Val Asp Gly Trp Tyr Gly Tyr His
                355                 360                 365
His Gln Asn Glu Gln Gly Ser Gly Tyr Ala Ala Asp Gln Lys Ser Thr
                370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
                420                 425                 430
```

```
Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 23
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205
```

His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Trp Tyr Ala Phe Ala
            260                 265                 270
Leu Ser Arg Gly Phe Gly Ser Gly Ile Ile Thr Ser Asn Ala Pro Met
        275                 280                 285
Asp Lys Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Phe Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
    530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 24
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

Gln Asn Ala Asp Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415
```

Glu Arg Arg Met Glu Asn Leu Asn Lys Lys Val Asp Gly Phe Leu
            420                 425                 430

Asp Ile Trp Thr Tyr Asn Ala Glu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 25
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asn
    130                 135                 140

Thr Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Lys
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

Gln Asn Ala Asp Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 26
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Lys
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Ser Ser His Tyr Ser Arg Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400
```

```
Lys Met Asn Thr Gln Phe Thr Ala Val Gly Lys Glu Phe Asn Lys Leu
            405                 410                 415

Glu Arg Arg Met Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 27
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Lys
                165                 170                 175
```

-continued

```
Leu Ser Lys Ser Tyr Ala Asn Asn Lys Glu Lys Glu Val Leu Val Leu
            180                 185                 190

Trp Gly Val His His Pro Asn Ile Gly Asp Gln Arg Ala Leu Tyr
        195                 200                 205

Gln Asn Ala Asp Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 28
<211> LENGTH: 6
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser His Asn Gly Lys Ser
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Pro His Ala Gly Ala Lys
1               5

<210> SEQ ID NO 30
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

His Thr Glu Asn
1

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Asn Ala Asp
1

<210> SEQ ID NO 32
<211> LENGTH: 6
<212> TYPE: PRT
<213> ORGANISM: Influenza A virus

<400> SEQUENCE: 32

Ser Trp Pro Asn His Asp
1               5

<210> SEQ ID NO 33
<211> LENGTH: 7
<212> TYPE: PRT
<213> ORGANISM: Influenza A virus

<400> SEQUENCE: 33

Tyr Pro Lys Leu Ser Lys Ser
1               5
```

```
<210> SEQ ID NO 34
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Trp Pro Asn His Thr
1               5

<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Tyr Pro Asn Leu Ser Lys Ser
1               5

<210> SEQ ID NO 36
<211> LENGTH: 6
<212> TYPE: PRT
<213> ORGANISM: Influenza A virus

<400> SEQUENCE: 36

Asp Ser Asn Lys Gly Val
1               5

<210> SEQ ID NO 37
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Val Thr Gly Val
1               5
```

UNITED STATES PATENT AND TRADEMARK OFFICE
CERTIFICATE OF CORRECTION

PATENT NO. : 11,116,832 B2
APPLICATION NO. : 16/306325
DATED : September 14, 2021
INVENTOR(S) : Strugnell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 232 days.

Signed and Sealed this
Twenty-seventh Day of December, 2022

*Katherine Kelly Vidal*

Katherine Kelly Vidal
*Director of the United States Patent and Trademark Office*